United States Patent
Holcombe et al.

(10) Patent No.: US 9,697,956 B2
(45) Date of Patent: Jul. 4, 2017

(54) DIKETOPYRROLOPYROLE (DPP)-BASED SENSITIZERS FOR ELECTROCHEMICAL OR OPTOELECTRONIC DEVICES

(71) Applicant: Ecole Polytechnique Federale de Lausanne (EPFL), Lausanne (CH)

(72) Inventors: Thomas Wesley Holcombe, Böhl-Iggelheim (DE); Jun Ho Yum, Yverdon-les-Bains (CH); Mohammad Khaja Nazeeruddin, Ecublens (CH); Michael Graetzel, St-Sulpice (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 74 days.

(21) Appl. No.: 14/425,239

(22) PCT Filed: Aug. 14, 2013

(86) PCT No.: PCT/IB2013/056648
§ 371 (c)(1),
(2) Date: Mar. 2, 2015

(87) PCT Pub. No.: WO2014/033582
PCT Pub. Date: Mar. 6, 2014

(65) Prior Publication Data
US 2015/0213966 A1    Jul. 30, 2015

(30) Foreign Application Priority Data
Sep. 3, 2012  (EP) .................................... 12182817

(51) Int. Cl.
*H01G 9/20* (2006.01)
*C09K 11/06* (2006.01)
*H05B 33/14* (2006.01)
*H01L 51/00* (2006.01)
*C07D 487/04* (2006.01)
*C09B 23/01* (2006.01)
*C09B 23/10* (2006.01)
*C09B 57/00* (2006.01)

(52) U.S. Cl.
CPC ......... *H01G 9/2059* (2013.01); *C07D 487/04* (2013.01); *C09B 23/005* (2013.01); *C09B 23/0058* (2013.01); *C09B 23/105* (2013.01); *C09B 57/004* (2013.01); *C09K 11/06* (2013.01); *H01L 51/0061* (2013.01); *H01L 51/0064* (2013.01); *H01L 51/0065* (2013.01); *H01L 51/0068* (2013.01); *H01L 51/0072* (2013.01); *H05B 33/14* (2013.01); *C09K 2211/1003* (2013.01); *C09K 2211/1011* (2013.01); *C09K 2211/1029* (2013.01); *C09K 2211/1033* (2013.01); *C09K 2211/1037* (2013.01); *C09K 2211/1044* (2013.01); *C09K 2211/1088* (2013.01); *C09K 2211/1092* (2013.01); *H01L 51/0067* (2013.01); *Y02E 10/542* (2013.01); *Y02E 10/549* (2013.01)

(58) Field of Classification Search
None
See application file for complete search history.

(56) References Cited

U.S. PATENT DOCUMENTS

| | | | | |
|---|---|---|---|---|
| 2008/0217581 A1* | 9/2008 | Yamamoto | ............. | C09K 11/06 252/301.16 |
| 2012/0071617 A1* | 3/2012 | Dueggeli | ............. | C08G 61/124 526/239 |

FOREIGN PATENT DOCUMENTS

| | | |
|---|---|---|
| CN | 101393970 B | 11/2010 |
| EP | 1253151 A1 | 10/2002 |
| EP | 1452574 A2 | 1/2004 |
| JP | 1142654 | 6/1989 |
| JP | 9003448 | 1/1997 |
| JP | 2007266285 A | 10/2007 |
| WO | 2011144566 A2 | 11/2011 |
| WO | 2011144566 A3 | 11/2011 |

OTHER PUBLICATIONS

Qu et al. New diketo-pyrrolo-pyrrole (DPP) sensitizer containing a furan moiety for efficient and stable dye sensitized solar cells. Dyes and Pigments 92 (2012) 1384-1393.*
Qu et al. New Diketopyrrolopyrrole (DPP) Dyes for Efficient Dye-Sensitized Solar Cells. J Phys Chem 2010, 114, 1343-1349.*
Qu et al. A novel D-A-pi-A organic sensitizer containing a diketopyrrolopyrrole unit with a branched alkyl chain for high efficient and stable dye sensitized solar cells. Chem Comm 2012, 48, 697206974.*
Qu, Sanyin et al. "New diketo-pyrrolo-pyrrole (DPP) sensitizer containing a furan moiety for efficient and stable dye-sensitized solar cells" Dyes and Pigements 92 (2012) 1384-1393.
Yum, JH et al. "Effect of coadsorbent on the photovoltaic performance of squaraine sensitized nanocrystalline solar cells" Nanotechnology 19 (2008) 424005 (6pp).

(Continued)

*Primary Examiner* — Tanisha Diggs
(74) *Attorney, Agent, or Firm* — Taft Stettinius & Hollister LLP

(57) ABSTRACT

The present invention relates to compounds of formula (I) based on DPP moiety being useful as metal-free organic sensitizers or dyes of type D-π-A in electrochemical or optoelectronic devices, their use as sensitizer or dye and an electrochemical or optoelectronic device comprising a compound of the invention.

(I)

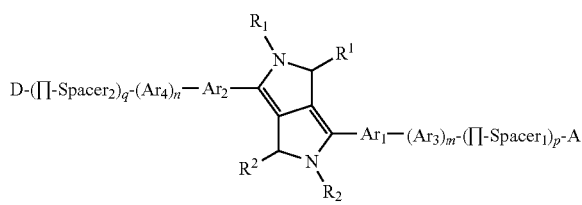

17 Claims, 9 Drawing Sheets

(56) References Cited

OTHER PUBLICATIONS

Qu, Sanyin et al. "New Diketopyrrolopyrrole (DPP) Dyes for Efficient Dye-Senstized Solar Cells" J. Phys, Chem. C, vol. 114, No. 2, 2010.
Qu, Sanyin et al. "New D-π-A dyes for efficient dye-sensitive solar cells" Science China, Chemistry, May 2012 vol. 55 No. 5: 677-697.
Qu, Sanyin et al. "Diketopyrrolopyrrole (DPP)-based materials for organic photovoltaics" Chem. Commun., 2012, 48, 3039-3051.
Warnan, Julien et al. "A compact diketopyrrolopyrrole dye as efficient sensitizer in titanium dioxide dye-sensitized solar cells" Journal of Photochemistry and Photobiology A: Chemistry 226 (2011) 9-15.

* cited by examiner

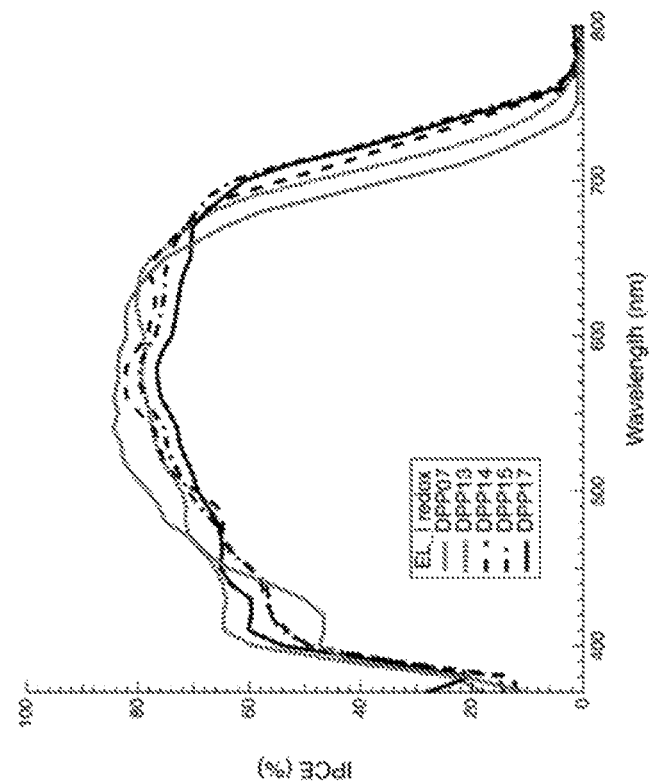
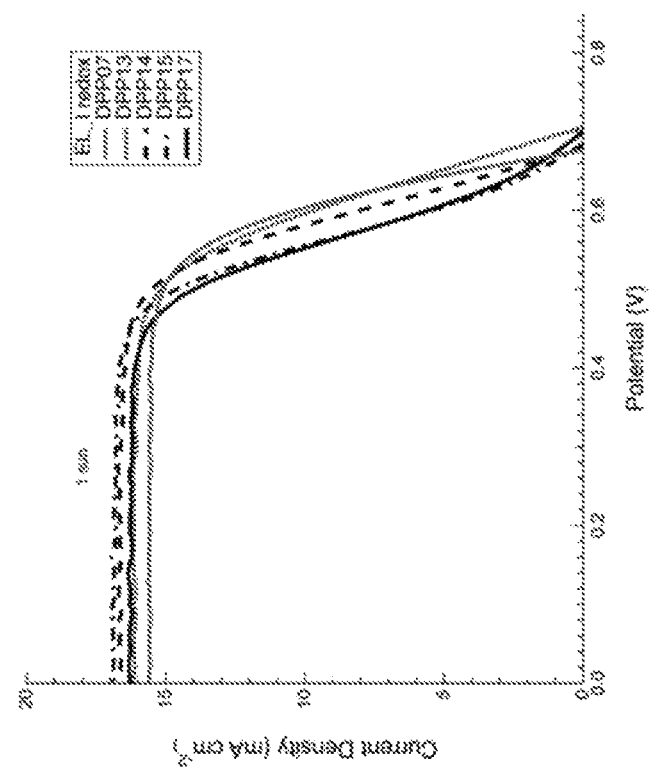
Fig. 15a
Fig. 15b

DIKETOPYRROLOPYROLE (DPP)-BASED SENSITIZERS FOR ELECTROCHEMICAL OR OPTOELECTRONIC DEVICES

The present application is a U.S. National Phase of International PCT Application No. PCT/IB2013/056648, filed on Aug. 14, 2013, which claims priority to European Patent Application No. 12182817.2, filed on Sep. 3, 2012, the contents of each application hereby incorporated by reference in its entirety.

TECHNICAL FIELD

The present invention relates to DPP-based sensitizers having asymmetric DPP bridge/core, to said DPP-based sensitizers for use in electrochemical and/or optoelectronic devices, an electrochemical or optoelectronic device, in particular, a dye-sensitized solar cell (DSSC) comprising such DPP-based sensitizers.

PRIOR ART AND THE PROBLEM UNDERLYING THE INVENTION

The dye-sensitized solar cell (DSC) is attracting widespread attention as a promising new generation of photovoltaic technology. Mimicking the principle of natural photosynthesis, its ecological and economical fabrication processes make it an attractive and credible alternative to conventional photovoltaic systems. Power conversion efficiencies (PCE) of over 10% make DSC technology a leader in the field of non-conventional photovoltaic. Such a device becomes ideal for integration with consumer electronics such as wireless keyboards, remote controls, and other battery powered devices. Optimizing components such as the appropriate nanostructured metal oxide, sensitizer, and redox shuttle offers control over aesthetic properties such as transparency and color, as well as performance parameters such as current density and output voltage.

The sensitizer is one of the most important components, determining both light harvesting efficiency and color of the DSC device. Metal-free organic sensitizers, such as diketopyrrolopyrrole (DPP)-based sensitizers, have many advantages such as lower cost, easier processing, and higher molar extinction coefficient than comparable metal complexes such as N719 and N3 (Hagfeldt et al., (2010), Chem. Rev., 110:6595-6663). The DPP moiety has the potential to harvest photons up to 900 nm in wavelength and is well known as an industrial colorant. DPP derivatives represent excellent stability and photoelectric properties and have been used in many other aspects of materials technology, from car-paint pigments to small molecule and polymeric organic photovoltaic (WO 2008/101570, WO 2011/144566). Polymers comprising DPP have been used as both sensitizer and hole-transport materials (HTM) for solid state DSC devices (Kanimozhi, et al., (2010), J. Phys. Chem C, 114:3287-3291) and a limited class of DPP structures have been utilized as molecular/dye-based D-π-A and Donor-Acceptor-Donor (D-A-D) sensitizers.

The standard metal-free DPP-based sensitizer consists of a donor-π-bridge-acceptor motif, where the DPP unit here is the π-bridge serving primarily to extend π-conjugation, while effectively relaying electron density from the donor to the acceptor. Alternatively, the acceptor of electron density, and anchor for binding the sensitizer to the rest of the DSC device, can be of the structure D-A-D, where the anchor and acceptor reside between two donor moieties. A DSC comprising a sensitizer based on the symmetrical DPP unit 3,6-diphenylpyrrolo[3,4-c]pyrrole-1,4(2H,5H)-dione, referring to the acceptor/anchor component of the dye, with triphenylamine or N,N-bis(4-methoxyphenyl)benzenamine moieties as donor moiety and carboxylic acid group as anchor moiety shows an overall conversion efficiency of only 2.68% (Guo et al., (2010), Synthetic Metals, 160:1767-1773). The more classical D-π-A approach towards DPP-based sensitizer development has led to an ultimate efficiency of 7.43% (Qu et al., (2012), Chem. Comm., 48:6972-6974) with the symmetrical DPP bridge/core 2,5-bis(2-ethylhexyl)-3,6-diphenylpyrrolo[3,4-c]pyrrole-1,4(2H,5H)-dione. Before this, the symmetrical DPP bridge/core 2,5-dibutyl-3,6-diphenylpyrrolo[3,4-c]pyrrole-1,4(2H,5H)-dione was utilized to yield an efficiency of 6.03%, by appropriate choice of acceptor/anchor (Qu et al., (2012), Dyes and Pigments, 92:1384-1393). The advance between the first and second report by Qu et al. is the choice of donor and N-alkyl solubilizing group on the DPP moiety. Before the development of appropriate donor, acceptor/anchor, and N-alkyl moiety choice for the 3,6-diphenylpyrrolo[3,4-c]pyrrole-1,4(2H,5H)-dione bridge/core, a comparison study between the two symmetrical cores 2,5-dibutyl-3,6-diphenylpyrrolo[3,4-c]pyrrole-1,4(2H,5H)-dione and 2,5-dibutyl-3,6-di(thiophen-2-yl)pyrrolo[3,4-c]pyrrole-1,4(2H,5H)-dione was performed: from this basic study it was determined that the symmetrical, thienyl-based, 2,5-dibutyl-3,6-di(thiophen-2-yl)pyrrolo[3,4-c]pyrrole-1,4(2H,5H)-dione core yielded only 1.45% PCE (Qu et al., (2010), J. Phys. Chem. C, 114:1343-1349). The PCE of DSCs comprising such sensitizers may still be improved by tuning the co-adsorption of such a sensitizer with chenodeoxycholic acid (CDCA) by hindering the formation of dye aggregates (Qu et al., (2010), J. Phys. Chem. C, 114:1343-1349). Also to reduce the π-π stacking of large π-conjugated systems of DPP units on a $TiO_2$ film or in solution, and to aid in loading the dye onto the $TiO_2$ from a loading solution, the DPP core of the sensitizers is substituted and could be further substituted with larger alkyl chains to also increase the solubility in loading solvents. All these previously reported DPP-based sensitizers have a symmetric DPP core, substituted by two identical aryl moieties thiophene or benzene. Improvements of these two DPP-based sensitizer cores/bridges, to increase the PCE of DSCs, have been provided by optimizing the donor and acceptor moiety combination, as well as the N-alkyl solubilizing moiety and device processing conditions such as co-adsorption with CDCA.

In view of the above mentioned prior art, the present invention addresses the problem to improve the performance of optoelectronic devices, in particular DSCs, by providing DPP-based dyes/sensitizers, wherein the absorbance spectrum is balanced with processability and aggregation.

It is also an objective of the invention to provide more stable optoelectronic and/or photoelectrochemical devices, in particular DSC, having improved or higher conversion efficiency (PCE), which may be obtained by increasing $V_{OC}$, IPCE or in other ways and having also indicator properties of their absorbance spectrum provided by the colour of the dye of the invention, such a blue color being very rare among DSC sensitizers.

The present invention addresses the problems depicted above, which are part of the invention.

SUMMARY OF INVENTION

Therefore, the inventors surprisingly found that DPP-based sensitizers comprising an asymmetric $Aryl_1$-DPP-$Aryl_2$ ($Ar_1$-DPP-$Ar_2$) core/bridge, wherein both aryl moieties are not identical, provided a gain in colour over the strictly symmetric 3,6-diphenylpyrrolo[3,4-c]pyrrole-1,4 (2H,5H)-dione core/bridge, wherein both aryl moieties are phenyl, while reducing aggregation phenomenon compared to the strictly symmetric 3,6-di(thiophen-2-yl)pyrrolo[3,4-c]pyrrole-1,4(2H,5H)-dione, wherein both aryl moieties are thienyl. The aryl-DPP core serves as an inherently coloured π-bridge, where the thienyl-DPP core possesses a broader spectral response compared to the phenyl-DPP core, particularly when both N-atoms are alkylated. The asymmetry leads to a balance between the spectral response/colour and charge injection/IPCE (incident photon-to-electron conversion efficiency) performance. The asymmetric $Ar_1$-DPP-$Ar_2$ core/bridge-based sensitizers are dyes with facile electronic communication between the donor and the core/bridge/chromophore to promote low-energy electronic absorbance transitions with low propensity for dye aggregation. The colour of the dye is an indicator of the absorption across all the visible and obtaining a blue color means that the invention provides a sensitizer which reaches the IR/NIR in spectral absorbance while allowing relative transparency in the high-energy blue photon region: with this asymmetric DPP core/bridge structure, access to a very rare class of DSC sensitizer colour has been achieved.

In an aspect, the invention provides a compound of formula (I) below

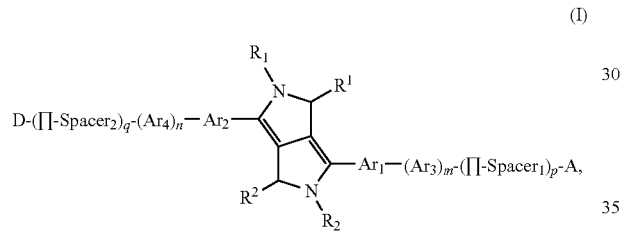

(I)

wherein:
m, n, p and q are independently selected from an integer from 0 to 3;
$R_1$ and $R_2$ are substituents independently selected from H, C1-C35 alkyl, C4-C35 aryl, C1-C35 arylalkyl, C4-C35 heteroaryl, wherein heteroatoms are selected from O, S or N;
$R^1$ and $R^2$ are substituents independently selected from H, OH, S, =O (keto group), C1-C35 alkyl, C1-C35 thioalkyl, C1-C35 alkoxy, C4-C35 aryl, C1-C35 arylalkyl, C4-C35 heteroaryl, wherein heteroatoms are selected from O, S or N;
$Ar_1$ and $Ar_2$ are different from each other and $Ar_1$ and $Ar_2$ are aromatic aryl groups independently selected from a moiety according to any one of formula (1) to (18):

(1)

(2)

(3)

-continued (4)

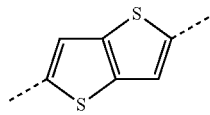

(5)

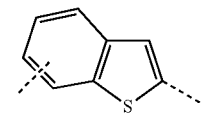

(6)

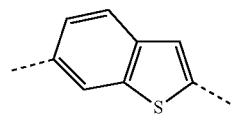

(7)

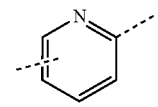

(8)

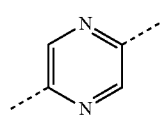

(9)

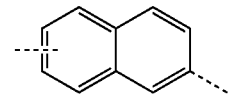

(10)

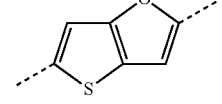

(11)

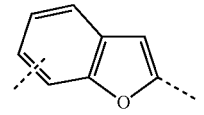

(12)

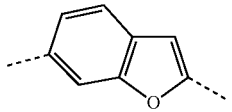

(13)

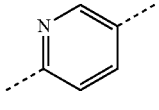

(14)

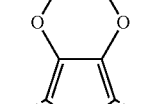

(15)

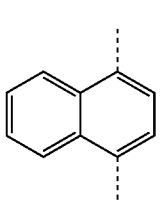

-continued

(16)
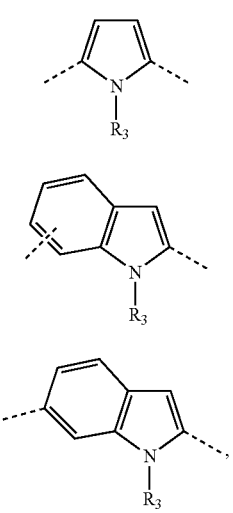

(17)

(18)

wherein R₃ is selected from H, C1-C35 alkyl, C4-C35 aryl, C1-C35 arylalkyl, or C4-C35 heteroaryl, wherein the heteroatoms are selected from O, S, or N;

Π-Spacer₁ and Π-Spacer₂ are independently selected from a moiety according to any one of formula (19) to (33):

(19)

(20)

(21)

(22)

(23)

(24)

(25)

-continued

(26)
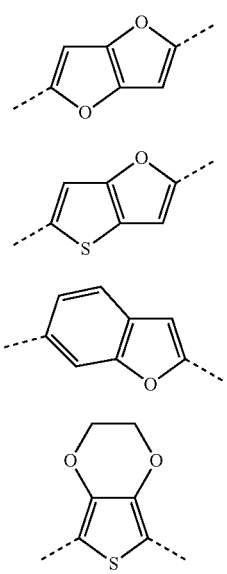

(27)

(28)

(29)

(30)

(31)

(32)

(33)

wherein R₄ is selected from H, C1-C35 alkyl, C1-C35 alkoxy, C1-C35 thioalkyl, C4-C35 aryl, C1-C35 arylalkyl or C4-C35 heteroaryl, wherein heteroatoms are selected from O, S, or N;

A is a substituent comprising an anchoring group "Anch" and an acceptor group and being selected from a moiety according to any one of formula (78) to (87):

(78)
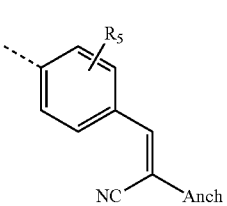

-continued

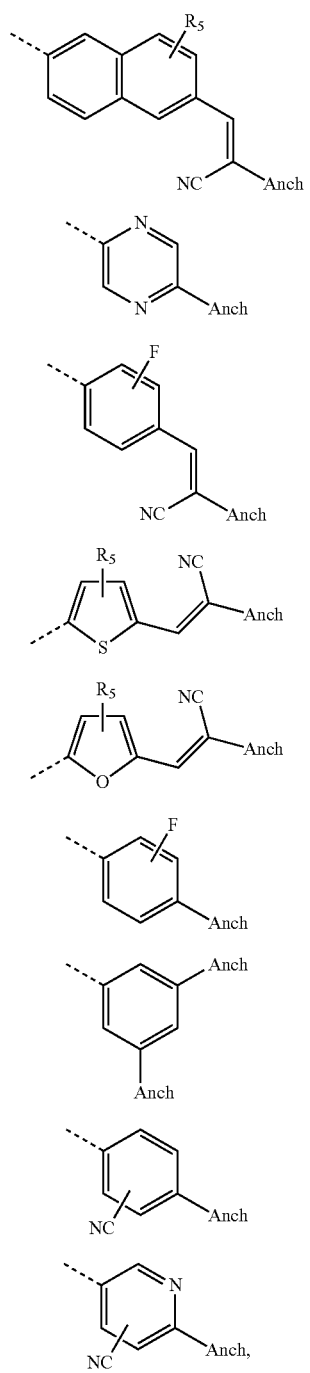

wherein $R_5$ is selected from H, C1-C35 alkyl, C1-C35 alkoxy, C1-C35 thioalkyl, C4-C35 aryl, C1-C35 arylalkyl or C4-C35 heteroaryl, wherein heteroatoms are selected from O, S, or N, and Anch is an anchoring group independently selected from —COOH, PO$_3$H$_2$, —PO$_4$H$_2$, —P(R$_8$)O$_2$H, —SO$_3$H$_2$, —SO$_4$H$_2$, —CONHOH$^-$, 1,2-hydroxybenzene, 1-hydroxy-2-carboxybenzene, acetylacetonate, deprotonated forms of the aforementioned, organic and/or inorganic salts of said deprotonated forms, and chelating groups with π-conducting character, wherein $R_8$ is a hydrocarbon comprising from 1 to 50 carbons and 0-25 heteroatoms selected from O, N, or S, said hydrocarbon being covalently bound to the P atom of said phosphinic acid group by a carbon atom;

D is a donor group selected from a moiety according to any one of formula (44) to (55):

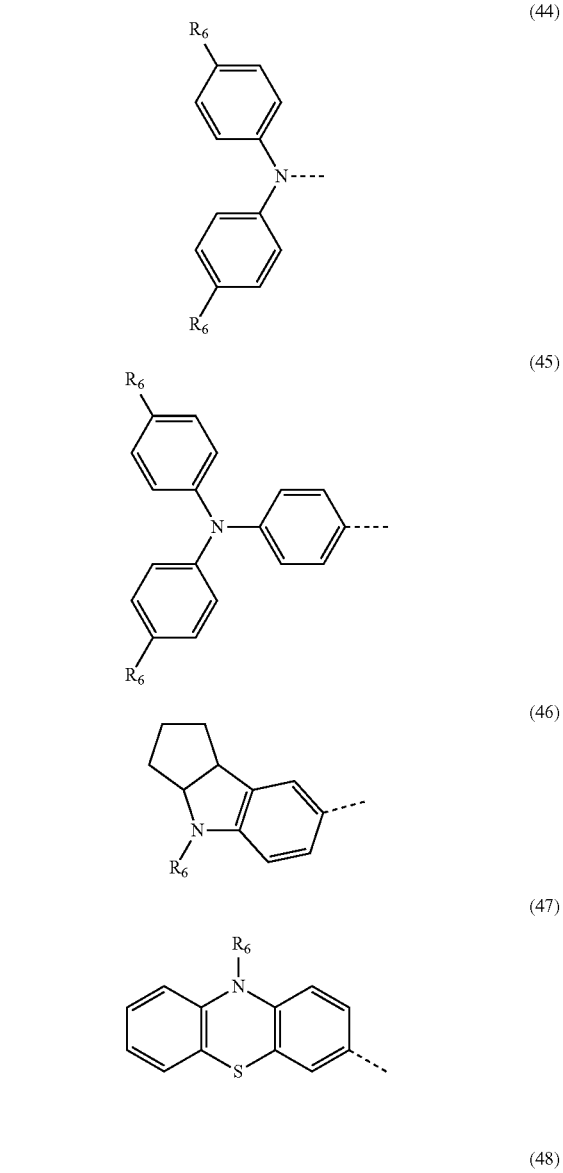

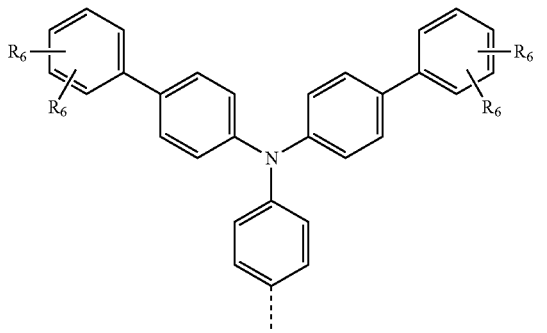

-continued
(49)
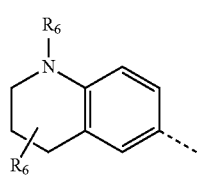
(50)
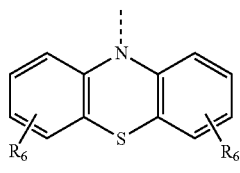
(51)
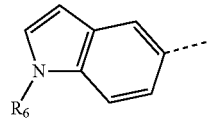
(52)
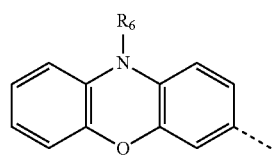
(53)
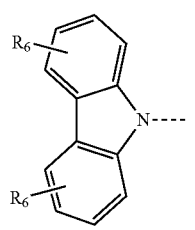
(54)
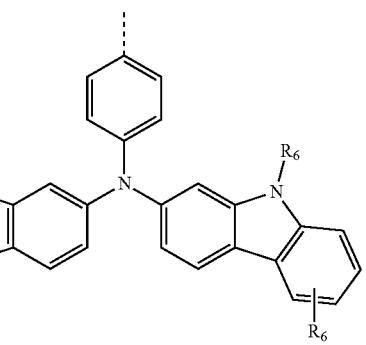
(55)
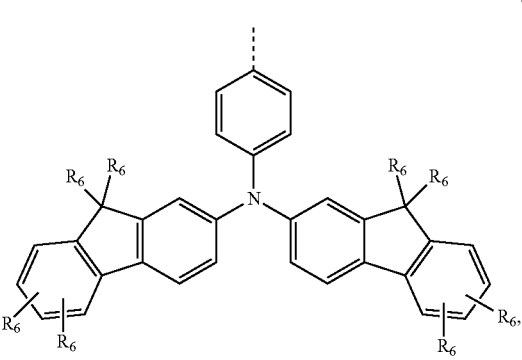
wherein $R_6$ is selected from H, C1-C35 alkyl, C1-C35 alkoxy, C1-C35 thioalkyl, C4-C35 aryl, C1-C60 arylalkyl or C4-C35 heteroaryl, wherein heteroatoms are selected from 0, S, or N and wherein aryl is optionally substituted by C4-C35 arylalkyl or by C4-C35 arylalkoxy groups;
$Ar_3$ and $Ar_4$ are aromatic aryl groups independently selected from a moiety according to any one of formula (56) to (70):
(56)
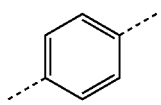
(57)
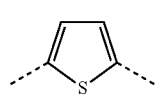
(58)
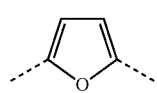
(59)
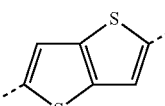
(60)
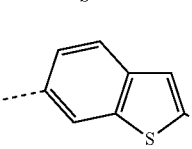
(61)
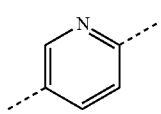
(62)
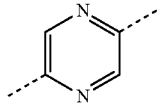
(63)
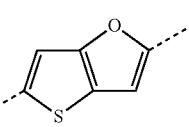
(64)
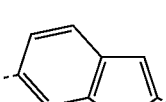
(65)
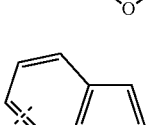
(66)
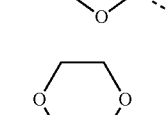

-continued

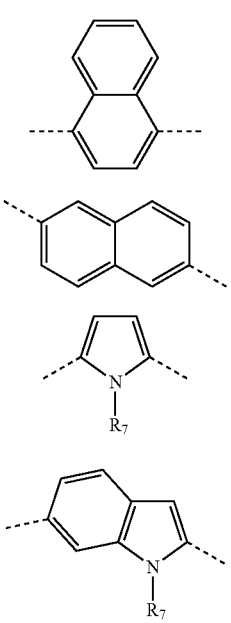

(67)

(68)

(69)

(70)

wherein R$_7$ is selected from H, C1-C35 alkyl, C4-C35 aryl, C1-C35 arylalkyl, or C4-C35 heteroaryl, wherein the heteroatoms are selected from O, S, or N;

and wherein said C1-C35 alkyl, C1-C35 alkoxy, C1-C35 thioalkyl, C4-C35 aryl, C1-C35 arylalkyl or C4-C35 heteroaryl may be further substituted or unsubstituted by a C1-C11 hydrocarbon comprising 0 to 15 heteroatoms selected from O, N, S or halogen.

Furthermore, the invention provides the use of said compound of formula (I) as dye or D-π-A sensitizer in an electrochemical or optoelectronic device. Said use increases both IPCE and spectral response compared to the use of 3,6-diphenylpyrrolo[3,4-c]pyrrole-1,4(2H,5H)-dione bridge/core/chromophore and an increased IPCE compared to the use of the 3,6-diphenylpyrrolo[3,4-c]pyrrole-1,4(2H, 5H)-dione bridge/core/choromophore.

In an aspect, the present invention provides a dye or a sensitizer comprising the compound of formula (I).

In another aspect, the present invention provides an electrochemical, preferably photoelectrochemical, or optoelectronic device comprising a dye, wherein said dye is a compound of formula (I).

In a further aspect, the present invention provides a method of preparing an electrochemical or optoelectronic device, preferably a DSC, providing a first and a second electrode, wherein the first electrode is the anode covered by a mesoporous oxide film of TiO$_2$, providing a compound of formula (I) as sensitizer to said mesoporous oxide film of TiO$_2$ and providing an intermediate layer comprising an electrolyte and a redox couple.

Further aspects and preferred embodiments of the invention are defined herein below and in the appended claims. Further features and advantages of the invention will become apparent to the skilled person from the description of the preferred embodiments given below.

DETAILED DESCRIPTION

Figure 1:
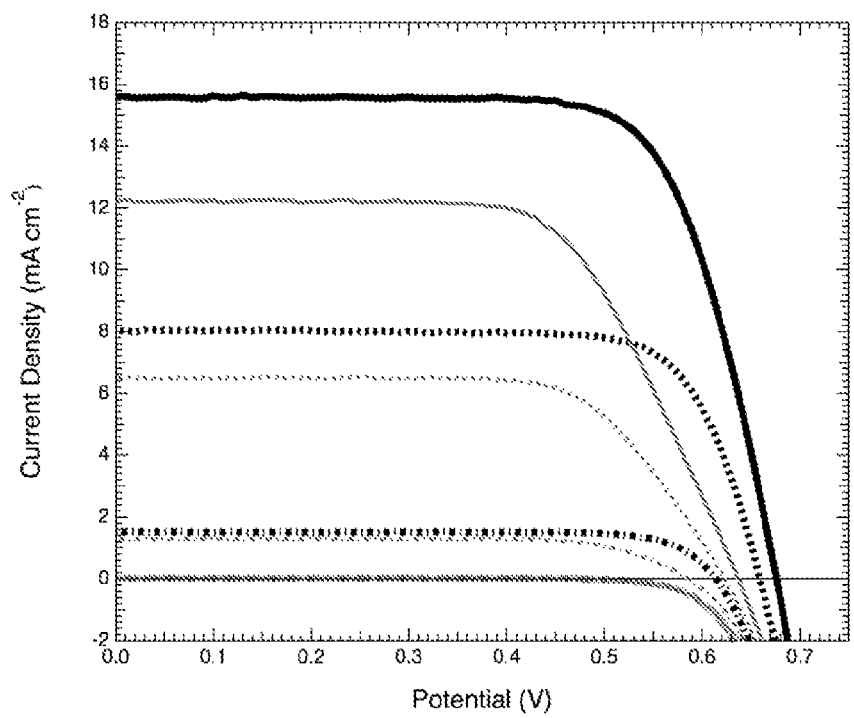
FIG. 1 shows Photovoltaic characteristics of solar cells comprising either DPP03, a compound of formula (I) based on a symmetric substituted DPP core as illustrated in FIG. 10 or DPP07, referred as compound of formula (72) base on an asymmetric substituted DPP core, in presence of CDCA under 9.5% (dash-dotted lines), 51% (dotted lines) and 100% (solid line) sun light intensities. Curves for solar cells comprising DPP03 are in grey and curves for solar cells comprising DPP07 are in black. The hatched curve indicates dark current of the devices.

The present invention provides compounds based on DPP moiety useful as metal-free organic sensitizers or dyes of type D-π-A in electrochemical or optoelectronic devices, their use as sensitizer or dye and an electrochemical or optoelectronic devices comprising a compound of the invention.

In particular, the compounds of invention are of formula (I) as described below:

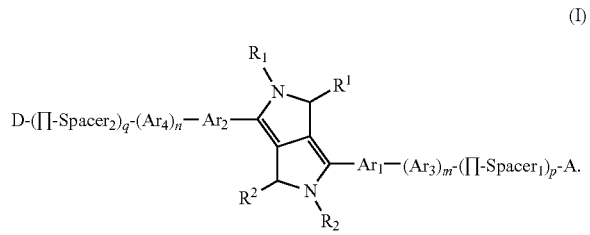

m, n, p and q in the compound of formula (I) are independently selected from an integer from 0 to 3. m, n, p and q are integer selected from 0, 1, 2 and 3. Preferably m and n are 0. Preferably p and q are 0 or 1, or p is 0 and q is 1, or p is 1 and q is 0. Preferably m and n are 0 and p and q are 0 or 1, or p is 1 and q is 0, or p is 0 and q is 1. Preferably p is 0 and q is 1.

The DPP (diketopyrrole) core is tuned to provide the better expected PCE as sensitizers for electrochemical, photoelectrochemical or optoelectronic device, in particular for dye sensitized solar cells (DSC) by adding aromatic groups ($Ar_1$, $Ar_2$, $Ar_3$ and $Ar_4$) and inserting a Π-spacer group ($Π-spacer_1$, $Π-spacer_2$) between said aromatic groups and the donor or the acceptor moiety (D or A, respectively).

$R_1$ and $R_2$ in the compound of formula (I) are substituents, which may be aromatic, and are independently selected from H, C1-C35 alkyl, C4-C35 aryl, C1-C35 arylalkyl, C4-C35 heteroaryl, wherein heteroatoms are selected from O, S or N. If alkyl, aryl, arylalkyl and heteroaryl groups comprise 3 or more carbons, they may be linear, branched or cyclic. $R_1$ and $R_2$ may be also selected from H, C1-C35 alkyl, C1-C35 alkenyl, C1-C35 alkynyl, C1-C35 heteroalkyl, aryl, C1-C35 arylalkyl, C4-C35 heteroaryl, wherein heteroatoms are selected from O, S or N. Preferably alkyl, alkynyl, arylalkyl are selected from hydrocarbon containing from 1 to 26 carbons, 1 to 15 carbons or 1 to 8 carbons. $R_1$ and $R_2$ may be identical or different. More preferably, $R_1$ and $R_2$ are 2-ethylhexyl or 2-octyldodecyl.

$R^1$ and $R^2$ in the compound of formula (I) are substituents independently selected from H, O, S, C1-C35 alkyl, C1-C35 thioalkyl, C1-C35 alkoxy, C4-C35 aryl, C1-C35 arylalkyl, C4-C35 heteroaryl, wherein heteroatoms are selected from O, S or N. If alkyl, thioalkyl, alkoxy groups comprise 3 or more carbons, they may be linear, branched or cyclic. Preferably alkyl, thioalkyl, alkoxy, arylalkyl are selected from hydrocarbon containing from 1 to 26 carbons, 1 to 15 carbons or 1 to 8 carbons. Preferably, $R^1$ and $R^2$ are selected from OH, =O (keto group), S, N C1-C35 alkoxy, or C1-C35 thioalkyl. $R^1$ and $R^2$ may be identical or different.

In another embodiment, $R^1$ and $R^2$ in the compound of formula (I) are substituents independently selected from H, OH, =O (keto group) S, C1-C35 alkyl, C1-C35 thioalkyl, C1-C35 alkoxy, C4-C35 aryl, C1-C35 arylalkyl, C4-C35 heteroaryl, wherein heteroatoms are selected from O, S or N. If alkyl, thioalkyl, alkoxy groups comprise 3 or more carbons, they may be linear, branched or cyclic. Preferably alkyl, thioalkyl, alkoxy, arylalkyl are selected from hydrocarbon containing from 1 to 26 carbons, 1 to 15 carbons or 1 to 8 carbons. Preferably, $R^1$ and $R^2$ are selected from OH, =O (keto group), S, N C1-C35 alkoxy, or C1-C35 thioalkyl. $R^1$ and $R^2$ may be identical or different. In a further preferred embodiment $R^1$ and $R^2$ are identical and are =O (keto group).

In a further embodiment, $R^1$ and $R^2$ in the compound of formula (I) are substituents independently selected from H, OH, =O (keto group), —OR, S, C1-C35 alkyl, C1-C35 thioalkyl, C1-C35 alkoxy, C4-C35 aryl, C1-C35 arylalkyl, C4-C35 heteroaryl, wherein R is selected from C1-C35 alkyl, C1-C35 thioalkyl, C1-C35 alkoxy, C4-C35 aryl, C1-C35 arylalkyl, C4-C35 heteroaryl and wherein heteroatoms are selected from O, S or N. If alkyl, thioalkyl, alkoxy groups comprise 3 or more carbons, they may be linear, branched or cyclic. Preferably alkyl, thioalkyl, alkoxy, arylalkyl are selected from hydrocarbon containing from 1 to 26 carbons, 1 to 15 carbons or 1 to 8 carbons.

In the compound of formula (I), $Ar_1$ and $Ar_2$ may be identical or different aromatic aryl groups.

In one embodiment, $Ar_1$ and $Ar_2$ are different from each other and $Ar_1$ and $Ar_2$ are aromatic aryl groups independently selected from a moiety according to any one of formula (1) to (18):

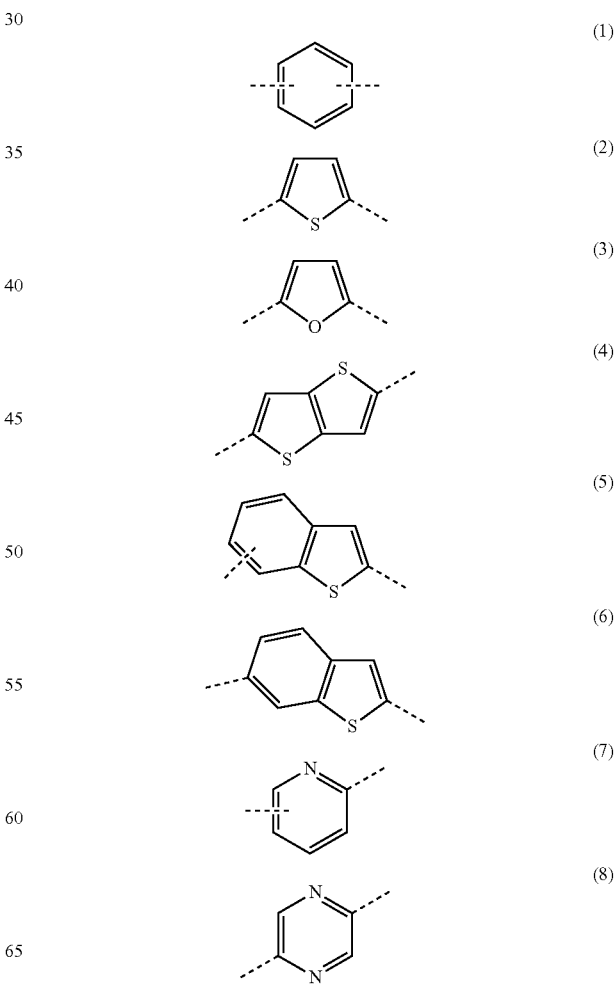

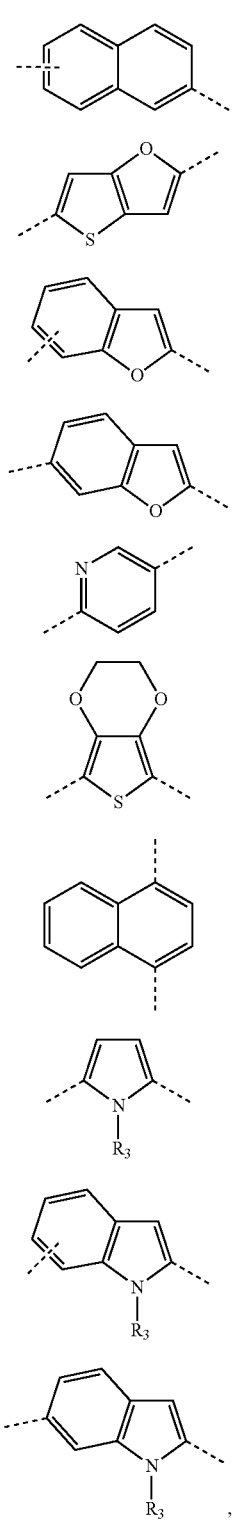

wherein R₃ is selected from H, C1-C35 alkyl, C4-C35 aryl, C1-C35 arylalkyl, or C4-C35 heteroaryl, wherein the heteroatoms are selected from O, S, or N. If alkyl, arylalkyl groups comprise 3 or more carbons, they may be linear, branched or cyclic. Preferably alkyl, arylalkyl are selected from hydrocarbon containing from 1 to 26 carbons, 1 to 15 carbons or 1 to 8 carbons.

In another embodiment, $Ar_1$ and $Ar_2$ are independently selected from a moiety of any one of formula (1), (2), (3), (7) and (13).

In a further embodiment $Ar_1$ is a moiety of formula (1), (7) or (13) and $Ar_2$ is a moiety of formula (2) or (3).

Figure 6:
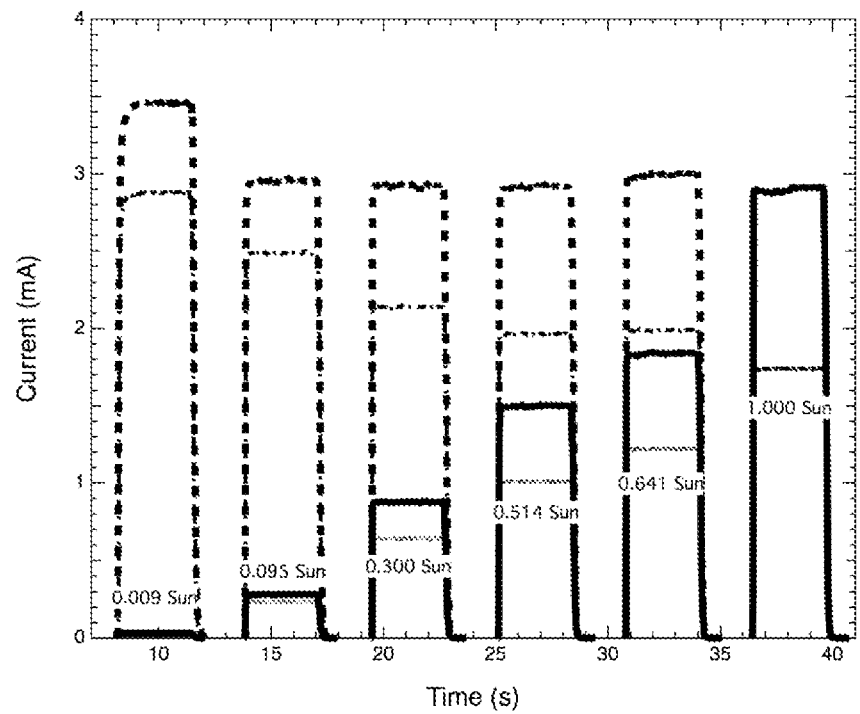
FIG. 6 shows current dynamics of solar cells comprising either DPP03 (hatched line, and dash-dotted line of measured current normalized with respect to 1 sun) or DPP07 (solid line, and dashed line for measured current normalized with respect to 1 sun) without CDCA as a function of light intensities.

Without wishing to be bound by theory, a surprising increase of the PCE of an electrochemical, photoelectrochemical or optoelectronic device, in particular a DSC, comprising a compound of the invention as a sensitizer is observed, if $Ar_1$ and $Ar_2$, being the two aryl groups substituting the DPP core of the compound of the invention, are not selected in the same groups of aromatic aryl groups and are different from each other. The compounds of invention comprise an asymmetric substituted DPP core compared to the previous sensitizers based on DPP cores having a DPP core symmetrically substituted by the same aryl groups. This asymmetric substitution of the DPP core provides an increase of the performance of a device comprising at least one compound of the invention as sensitizer or dye. This increase is explained by the generation of a linear current with light intensity in a DSC comprising a compound of the invention as sensitizer (FIG. 6).

Figure 2:
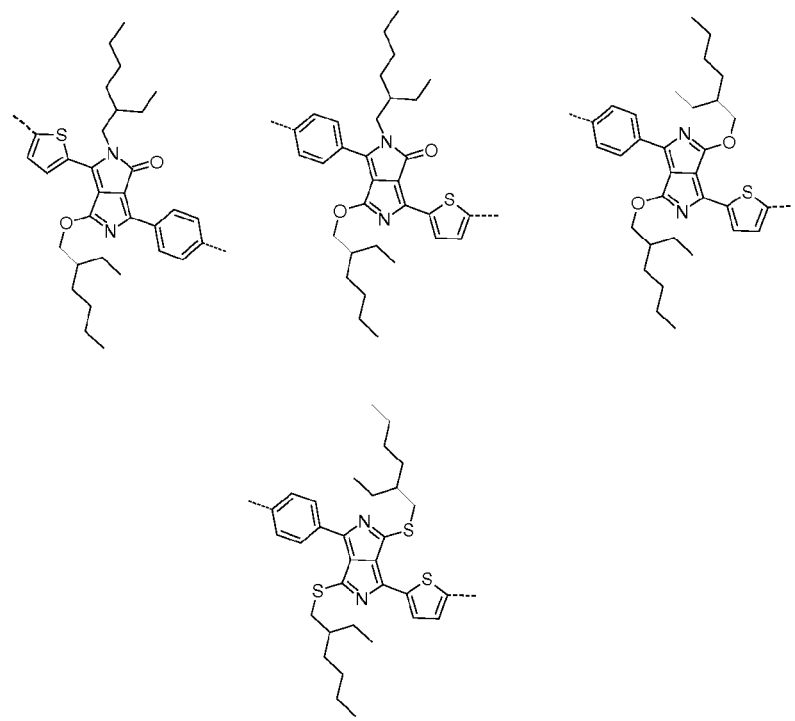
FIG. 2 shows asymmetric DPP cores of compounds of the invention, which are substituted in R$_1$, R$_2$, R$^1$ and R$^2$ and may be further substituted by Ar3, Ar4, Π-Spacer$_1$, Π-Spacer$_2$, A and D as described and defined in the compound of the invention of formula (I).

Some preferred asymmetric DPP cores of compounds of the invention substituted by different $Ar_1$ and $Ar_2$ selected from different moieties and which are further substituted in $R_1$, $R_2$, $R^1$ and $R^2$ are described in FIG. 2. Said DPP core may be further substituted by $Ar_3$, $An_4$, $\Pi$-$Spacer_1$, $\Pi$-$Spacer_2$, A and D as described and defined in the compound of the invention of formula (I).

In said asymmetric DPP cores of FIG. 2, the connection of the asymetric DPP core substituted in $Ar_1$ and $Ar_2$ to a following moiety according to any one of moieties of $Ar_3$, $Ar_4$, $\Pi$-$Spacer_1$, $\Pi$-$Spacer_2$, A or D, if present, is illustrated by way of a dashed line representing a covalent bond.

In another embodiment, $Ar_1$ and $Ar_2$ are identical aromatic aryl groups and are selected from a moiety according to any one of formula (3) to (18). Preferably they are moieties of formula (3).

In the compound of formula (I), $\Pi$-$Spacer_1$ and $\Pi$-$Spacer_2$ are selected from aromatic moieties. They are independently selected from a moiety according to any one of formula (19) to (33):

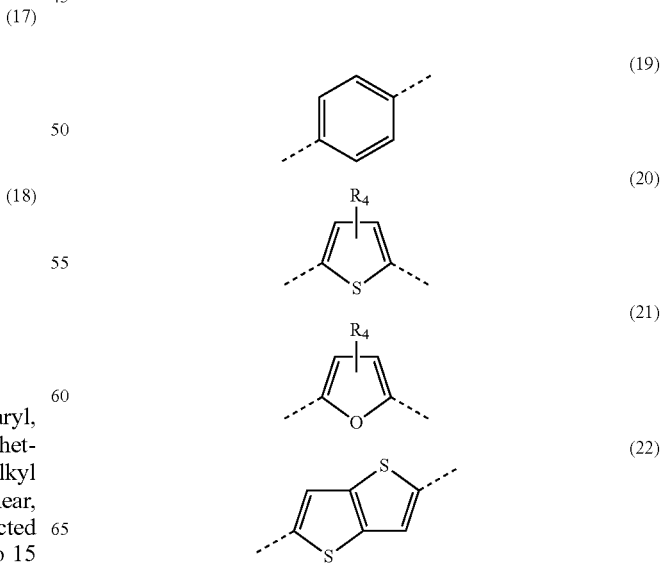

-continued

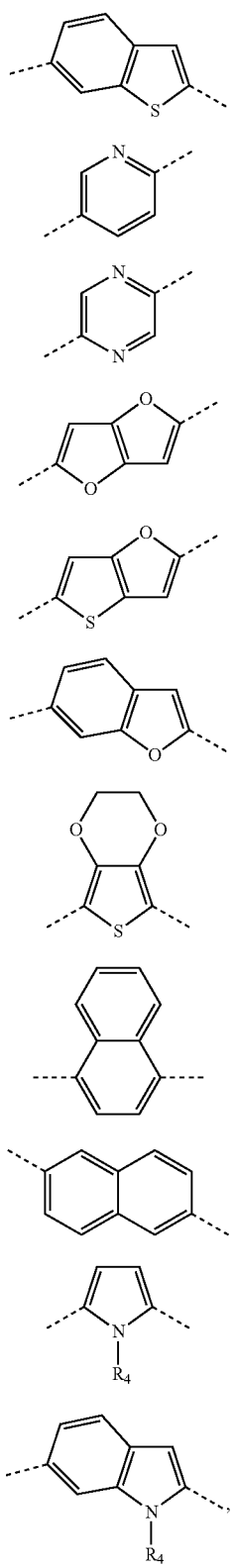

(23)
(24)
(25)
(26)
(27)
(28)
(29)
(30)
(31)
(32)
(33)

wherein $R_4$ is selected from H, C1-C35 alkyl, C1-C35 alkoxy, C1-C35 thioalkyl, C4-C35 aryl, C1-C35 arylalkyl or C4-C35 heteroaryl, wherein heteroatoms are selected from O, S, or N. If alkyl, alkoxy, thioalkyl arylalkyl groups comprise 3 or more carbons, they may be linear, branched or cyclic. Preferably alkyl, arylalkyl are groups selected from groups containing from 1 to 26 carbons, 1 to 15 carbons or 1 to 8 carbons.

The connection of the compound of the invention onto the semiconductor surface is effected by way of an anchoring group of the compound of the invention. Said connection can be by way of electrostatic interaction and/or of covalent connection and/or coordinate covalent, which is stable for at least 10 hours, preferably at least 10 weeks, mote preferably at least 10 months and ideally up to an more that 1-3 years. The anchoring group is suitable to anchor said compound of formula (I) onto the surface of a semiconductor. In particular, the compound having the core structure is preferably in any way adsorbed or attached on a surface of said semiconductor, in particular by way of said anchoring group.

In the compound of formula (I), A is a substituent comprising an anchoring group "Anch" and an acceptor group and being selected from a moiety according to any one of formula (78) to (87):

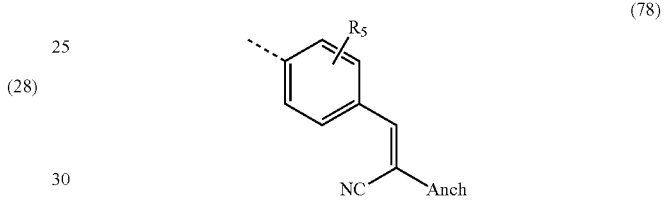
(78)

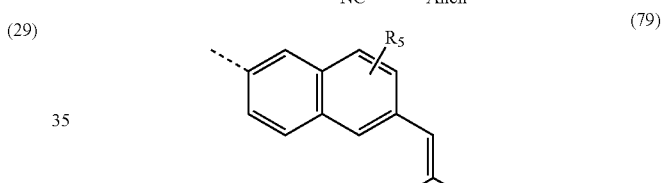
(79)

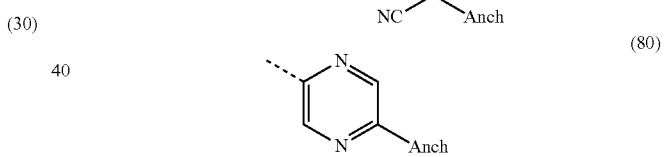
(80)

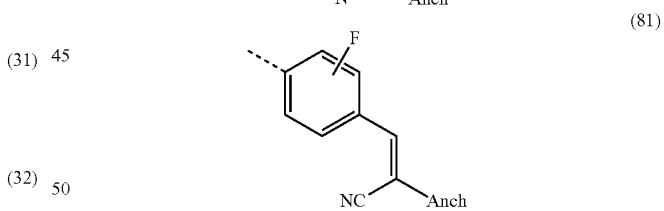
(81)

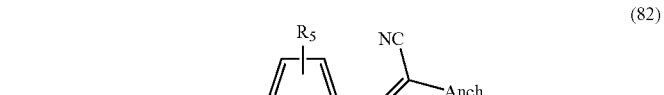
(82)

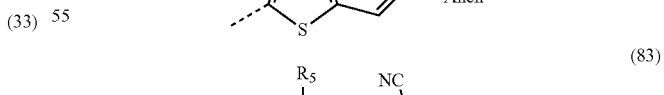
(83)

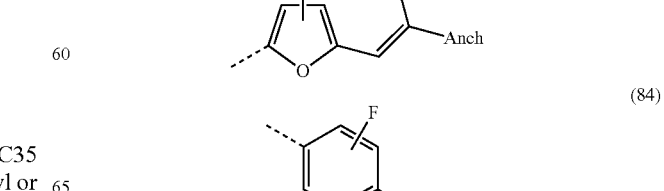
(84)

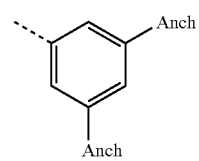
(85)

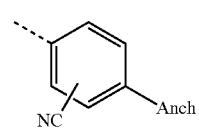
(86)

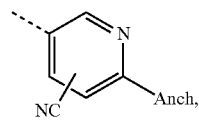
(87)

wherein R₅ is selected from H, C1-C35 alkyl, C1-C35 alkoxy, C1-C35 thioalkyl, C4-C35 aryl, C1-C35 arylalkyl or C4-C35 heteroaryl, wherein heteroatoms are selected from O, S, or N. If alkyl, alkoxy, thioalkyl, arylalkyl groups comprise 3 or more carbons, they may be linear, branched or cyclic. Preferably alkyl chain is linear or branched and contains from 1 to 35 C. Preferably C₃ of the aryl moiety of formulae (81) and (84) is substituted by the halogen F. A is preferably selected from a moiety according any one of formula (78), (80), (82), (83) or (84).

Anch is an anchoring group independently selected from —COOH, PO₃H₂, —PO₄H₂, —P(R₈)O₂H, —SO₃H₂, —SO₄H₂, —CONHOH⁻, 1,2-hydroxybenzene, 1-hydroxy-2-carboxybenzene, acetylacetonate, deprotonated forms of the aforementioned, organic and/or inorganic salts of said deprotonated forms, and chelating groups with π-conducting character. R₈ may be a hydrocarbon comprising from 1 to 50 carbons and 0-25 heteroatoms selected from O, N, or S, said hydrocarbon being covalently bound to the P atom of said phosphinic acid group by a carbon atom. R₈ may a substituted or unsubstituted, linear, branched or cyclic C1-C20 alkyl, C2-C20 alkenyl, C2-C20 alkynyl, and C4-C20 aryl.

According to an embodiment, in the compound of formula (I), A is preferably a substituent comprising an anchoring group and/or an acceptor group and being selected from a moiety according to any one of formula (34) to (43):

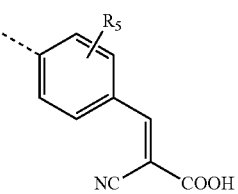
(34)

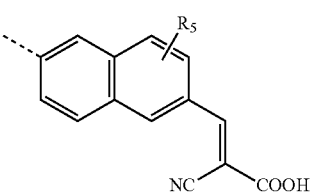
(35)

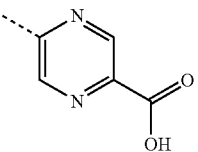
(36)

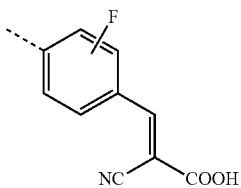
(37)

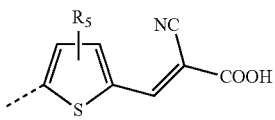
(38)

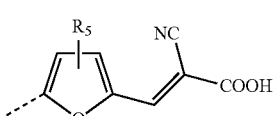
(39)

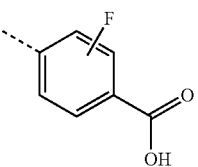
(40)

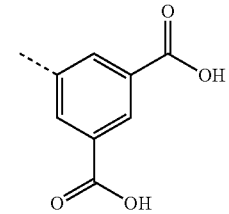
(41)

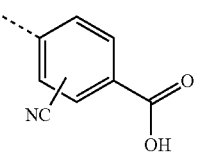
(42)

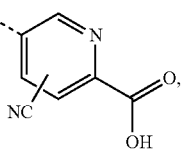
(43)

wherein R₅ is selected from H, C1-C35 alkyl, C1-C35 alkoxy, C1-C35 thioalkyl, C4-C35 aryl, C1-C35 arylalkyl or C4-C35 heteroaryl, wherein heteroatoms are selected from O, S, or N. If alkyl, alkoxy, thioalkyl, arylalkyl groups comprise 3 or more carbons, they may be linear, branched or cyclic. Preferably alkyl chain is linear or branched and contains from 1 to 35 C. Preferably C₃ of the aryl moiety of formulae (37) and (40) is substituted by the halogen F. Preferably A is selected from a moiety according any one of formula (34), (36), (38), (39) or (40).

D in the compound of formula (I) is preferably a donor group selected from a moiety according to any one of formula (44) to (55):

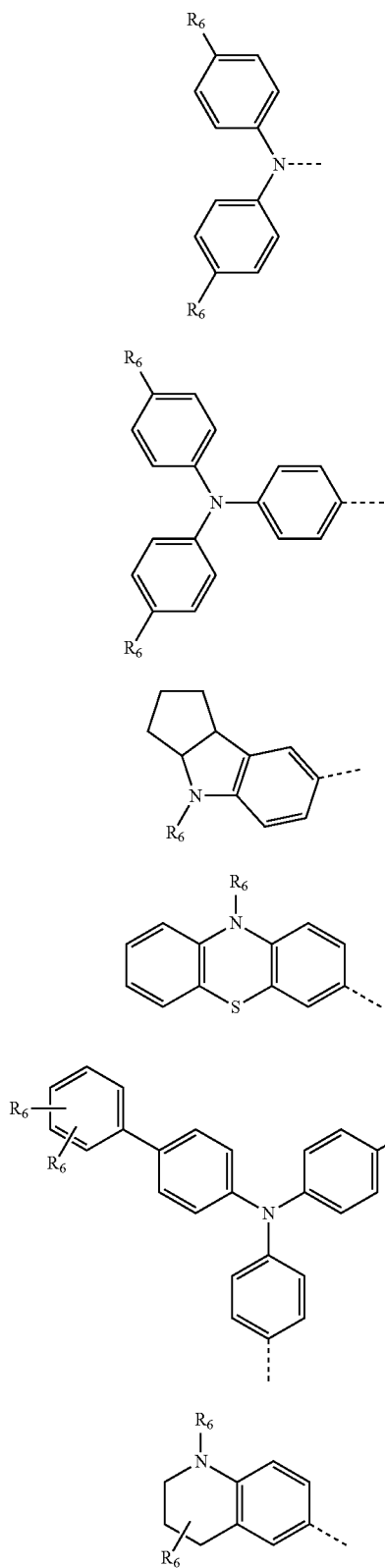

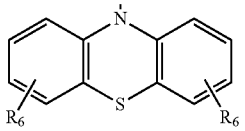

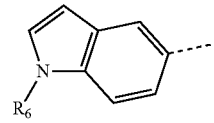

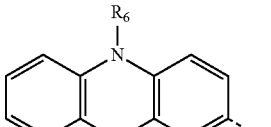

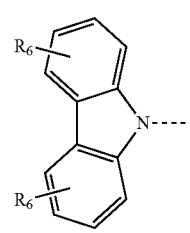

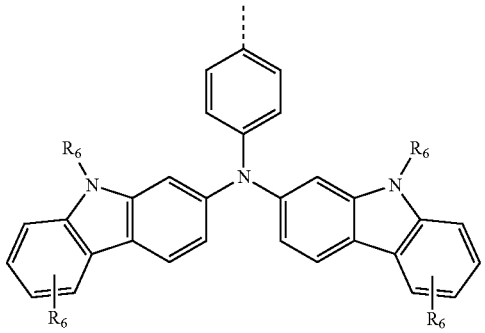

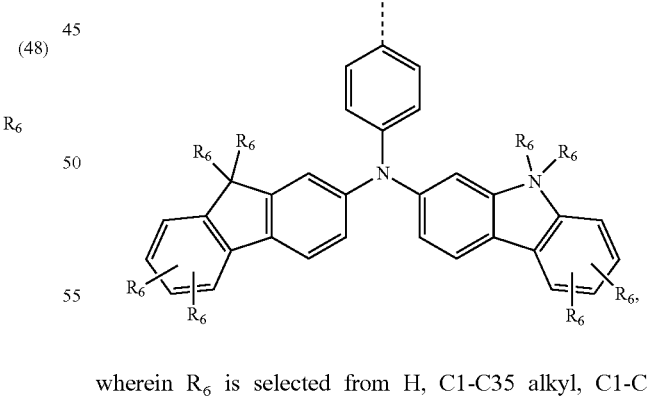

wherein $R_6$ is selected from H, C1-C35 alkyl, C1-C35 alkoxy, C1-C35 thioalkyl, C4-C35 aryl, C1-C60 arylalkyl or C4-C35 heteroaryl, wherein heteroatoms are selected from O, S, or N and wherein aryl is optionally substituted by C4-C35 arylalkyl or by C4-C35 arylalkoxy groups. If alkyl, alkoxy, thioalkyl arylalkyl groups comprise 3 or more carbons, they may be linear, branched or cyclic. Preferably alkyl chain is linear or branched and contains from 1 to 35 C. Preferably, D is selected from a moiety according to any one of formula (45), (46), (48) and (54).

The acceptor and/or anchoring group ("Anch") of substituent A and the donor group D are not limited to the moieties of formula 34 to 43, 78 to 87 and of formula 44 to 55, respectively. Said acceptor and/or anchor group and the donor group D may be also selected from moieties disclosed as acceptor or anchor groups and as donor groups of sensitizers commonly used for DSC as disclosed in Hagfeldt et al. ((2010), Chem. Rev., 110:6595-6663) and in PCT/IB2011/054628, which is entirely incorporated herein by reference.

In the compound of formula (I), $Ar_3$ and $Ar_4$ are aromatic aryl groups independently selected from a moiety according to any one of formula (56) to (70):

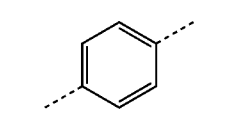
(56)

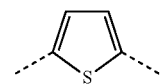
(57)

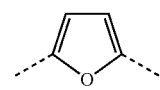
(58)

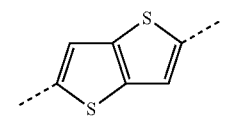
(59)

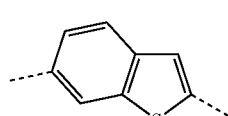
(60)

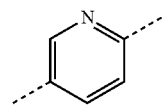
(61)

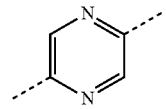
(62)

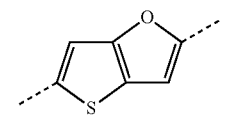
(63)

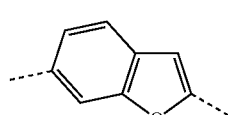
(64)

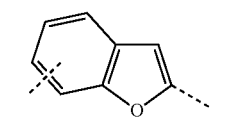
(65)

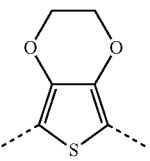
(66)

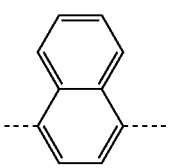
(67)

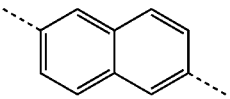
(68)

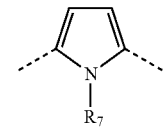
(69)

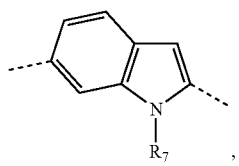
(70)

wherein $R_7$ is selected from H, C1-C35 alkyl, C4-C35 aryl, C1-C35 arylalkyl, or C4-C35 heteroaryl, wherein the heteroatoms are selected from O, S, or N. If alkyl, arylalkyl groups comprise 3 or more carbons, they may be linear, branched or cyclic. Preferably alkyl, arylalkyl are groups selected from groups containing from 1 to 26 carbons, 1 to 15 carbons or 1 to 8 carbons.

In the compound of formula (I), said C1-C35 alkyl, C1-C35 alkoxy, C1-C35 thioalkyl, C4-C35 aryl, C1-C35 arylalkyl or C4-C35 heteroaryl may be further substituted or unsubstituted by a C1-C11 hydrocarbon comprising 0 to 15 heteroatoms selected from O, N, S or halogen. Halogen are selected from F, Cl, Br, or I.

According to an embodiment, the alkyl chains of groups of C1-C35 alkyl and C1-C35 arylalkyl of the compounds of invention are branched C1-C35 alkyl chains.

In the moieties of formula (1) to (70), the connection of any moiety to the basic structure DPP-core or to a preceding moiety (for example, if one or the other of the integer m, n, p or q is different from 0) is illustrated by way of a dashed line representing the bond indicating the connection of the moiety to either the DPP-core and to the following moiety, or to the preceding moiety and the following moiety.

According to an embodiment, the compounds of formula (I) are selected from anyone of compounds of formula (72) to (77) and (88):

(72)
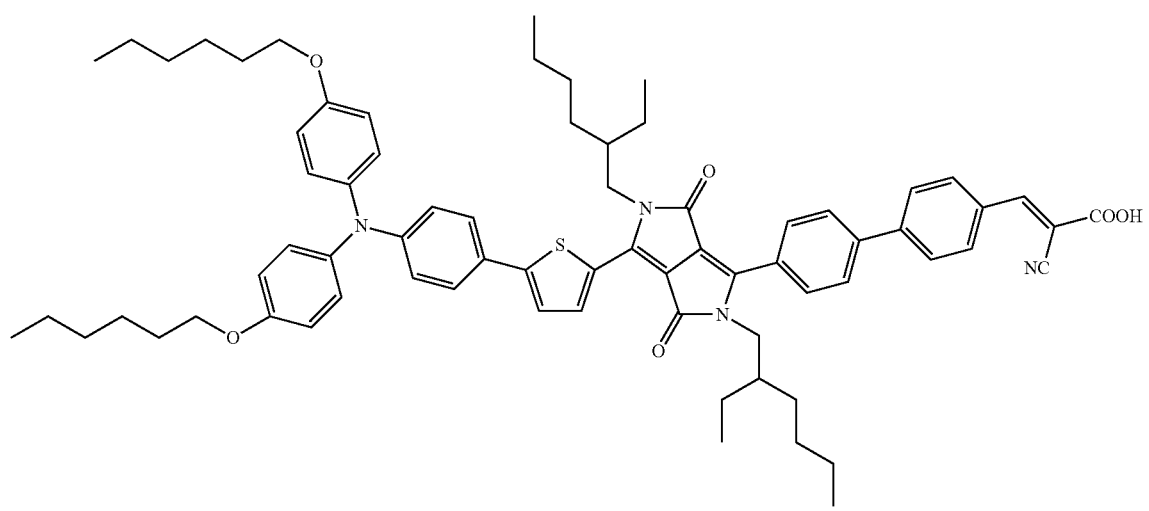
(73)
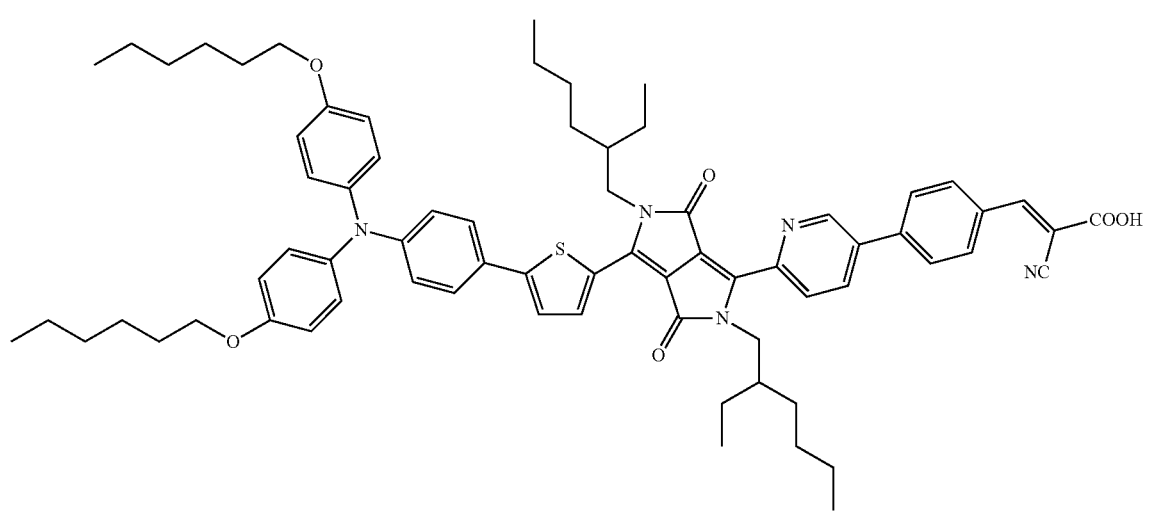

(74)
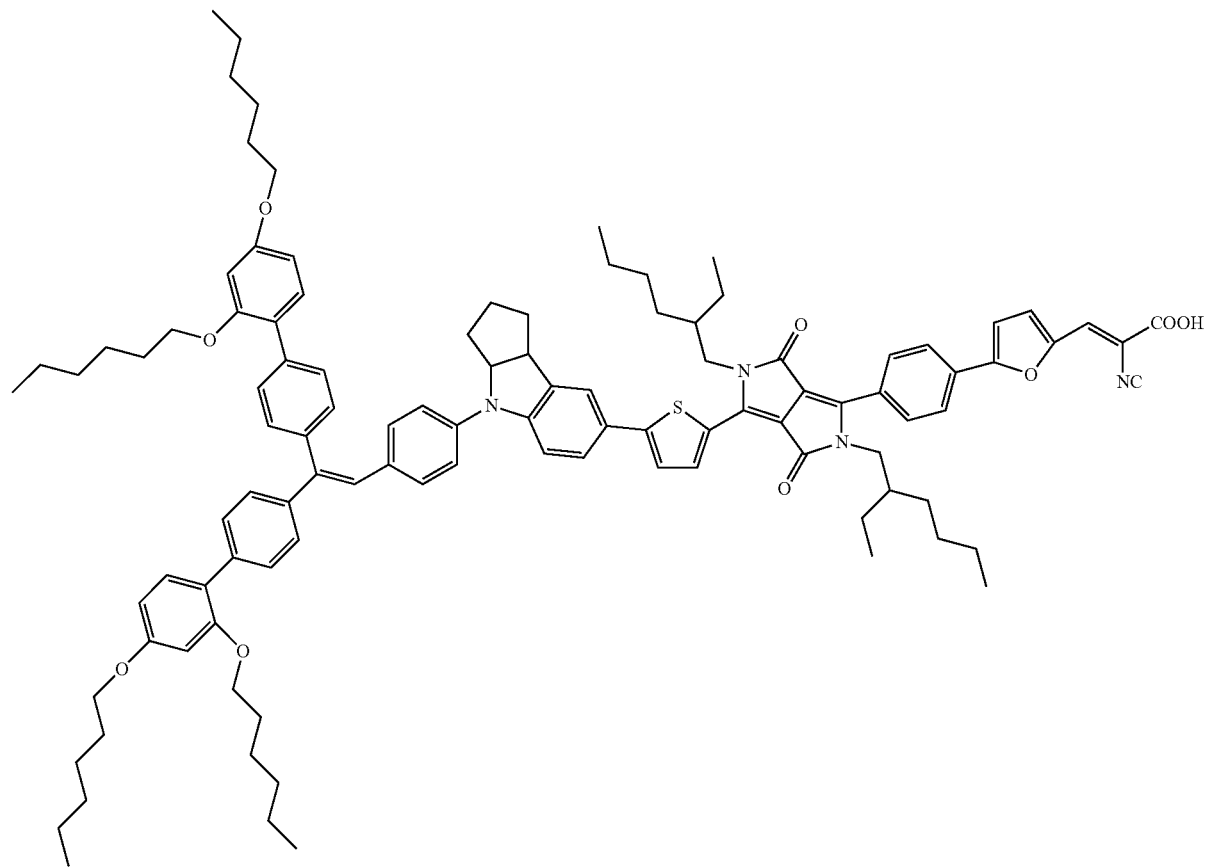
(75)
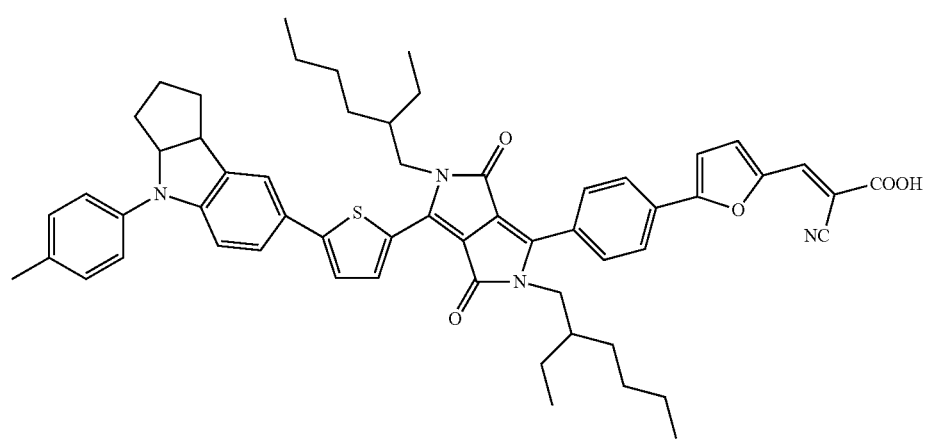

-continued
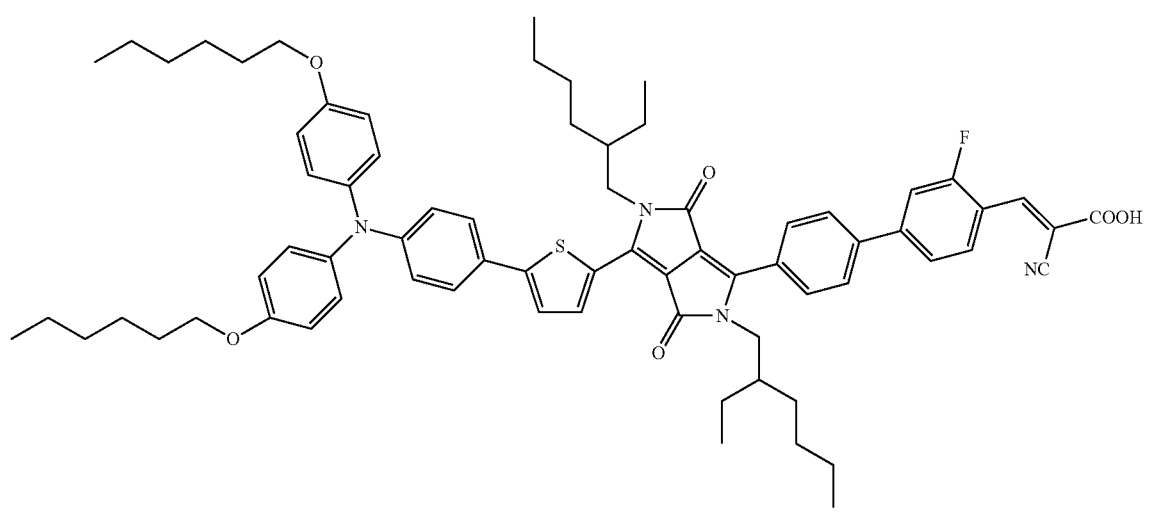
(76)
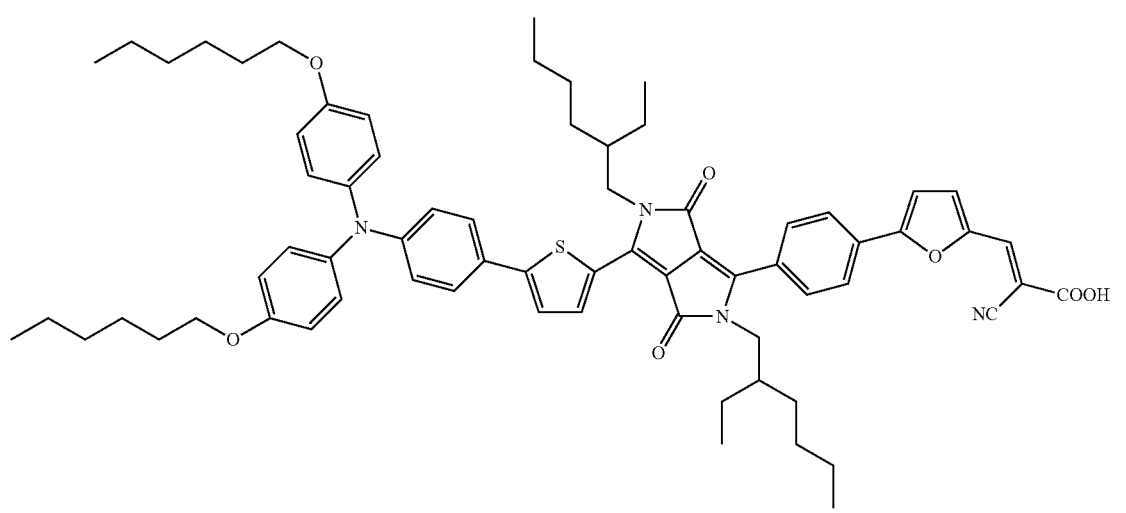
(77)
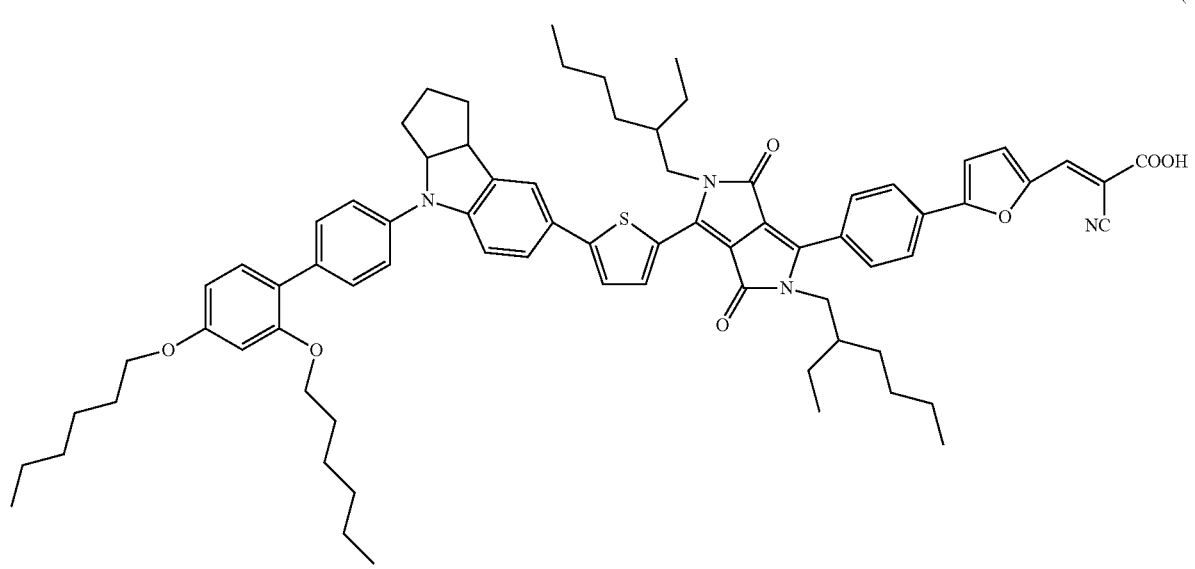
(88)

The invention also provides a use of a compound of formula (I) as dye or D-π-A sensitizer in an electrochemical or optoelectronic device.

In another aspect, the present invention provides a dye or a sensitizer comprising a compound of formula (I). Said dye may be co-adsorbed with CDCA and/or with further co-sensitizer. Said co-sensitizer, if present, is preferably selected among wide-bandgap sensitizers. Preferably, the co-sensitizer is the compound of formula (71)

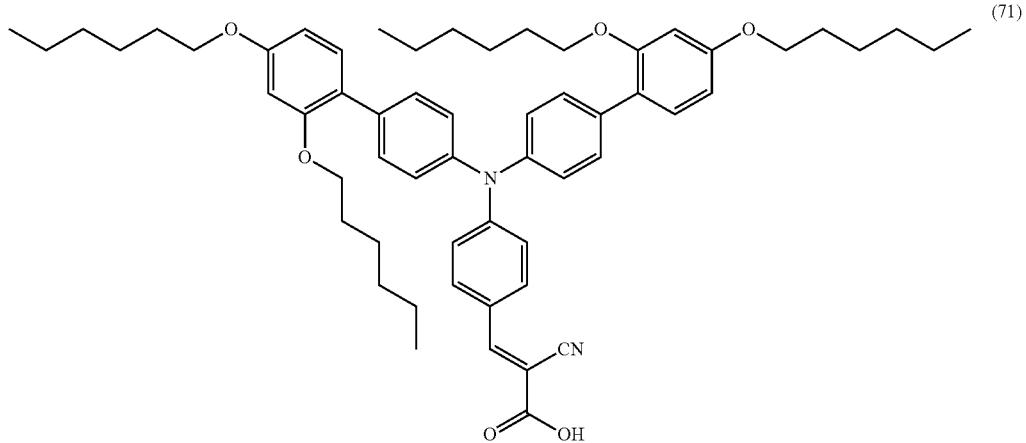 [SMILES: CCCCCCOc1ccc(-c2ccc(N(c3ccc(/C=C(\C#N)C(=O)O)cc3)c3ccc(-c4ccc(OCCCCCC)cc4OCCCCCC)cc3)cc2)c(OCCCCCC)c1]

(71)

The invention further provides, in one aspect, an electrochemical or optoelectronic device comprising a dye, wherein said dye is a compound of formula (I) of the invention.

In another embodiment, the device of the invention comprises a semiconductor surface on which the compound of the invention is adsorbed.

According to an embodiment, the device of the invention is selected from an electrochemical device, a photo-electrochemical device, an optoelectronic device, a light emitting device, an electrochromic or photo-electrochromic device, an electrochemical sensor, a biosensor, an electrochemical display and an electrochemical capacitor, or a dye sensitized solar cell.

According to a preferred embodiment, the electrochemical device is a photoelectrical conversion device selected from a solar cell, a dye-sensitized solar cell (DSC), a regenerative dye-sensitized solar cell, a photovoltaic device or a photovoltaic cell. The device of the invention is the most preferably a dye-sensitized solar cell (DSC). In said device, the semiconductor is sensitized by the compound of the invention of formula (I), which may be connected onto the semiconductor surface by way of its anchoring group comprised in the substituent "A" of formula (I).

In a preferred embodiment, the device of the invention is a dye sensitized solar cell, wherein the dye comprising a compound of formula (I) is co-adsorbed with CDCA (chenodeoxycholic acid). Preferably said dye is co-adsorbed with CDCA and/or the compound of formula (71).

In a further aspect, the present invention provides a method of preparing an electrochemical or optoelectronic device, preferably a DSC, providing a first and a second electrode, wherein the first electrode is the anode covered by a mesoporous oxide film of $TiO_2$, providing a compound of formula (I) as sensitizer to said mesoporous oxide film of $TiO_2$ and providing an intermediate layer comprising an electrolyte and a redox couple, or a hole transporting material for solid state devices.

The present invention will now be illustrated by way of examples. These examples do not limit the scope of this invention, which is defined by the appended claims.

EXAMPLE

Example 1

Synthesis of Compound of Formula (72)
Corresponding to DPP07

Figure 12:
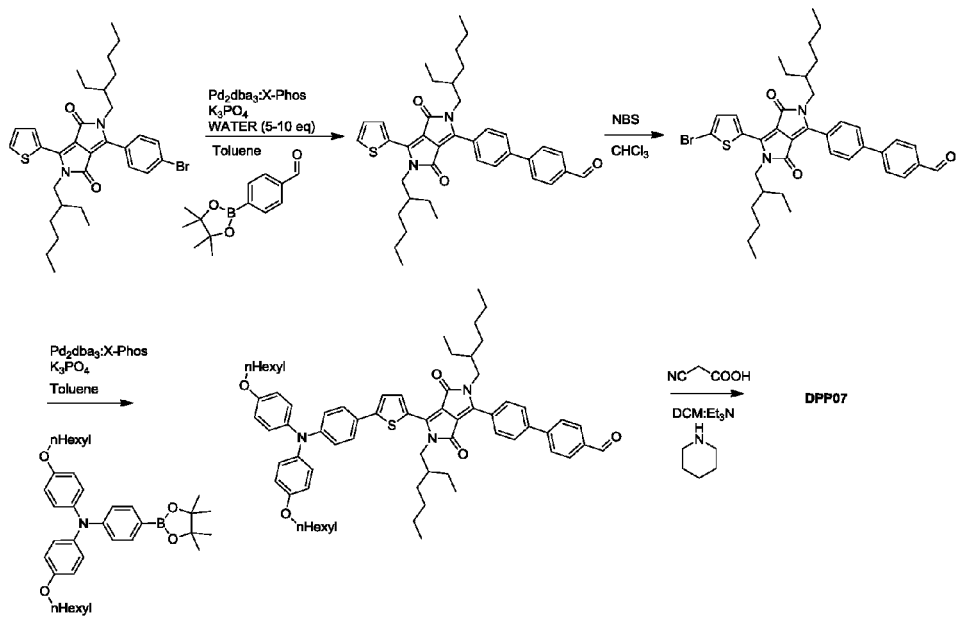
FIG. 12 shows the general scheme of the synthesis of compound of formula (72) referred also as DPP07.

3-(4-bromophenyl)-2,5-bis(2-ethylhexyl)-6-(thiophen-2-yl)pyrrolo[3,4-c]pyrrole-1,4(2H,5H)-dione was synthesized in an analogous method to what was reported in WO 2011/144566 and WO 2010/144566. The general scheme of the synthesis is shown in FIG. 12.

$^1$H NMR (400 MHz, Methylene Chloride-d2) δ 8.90 (dd, J=3.9, 1.1 Hz, 1H), 7.71 (dd, J=5.0, 1.2 Hz, 1H), 7.67 (s, 4H), 7.30 (dd, J=5.1, 3.9 Hz, 1H), 3.99-3.86 (m, 2H), 3.86-3.70 (m, 2H), 1.85-1.75 (m, 1H), 1.49-1.40 (m, 1H), 1.40-0.99 (m, 16H), 0.89-0.68 (m, 12H). $^{13}$C NMR (100 MHz, Methylene Chloride-d2) δ 162.03, 161.79, 144.98, 135.49, 131.97, 131.26, 130.15, 129.76, 128.92, 128.28, 128.11, 127.69, 124.85, 45.44, 44.84, 39.06, 38.66, 30.22, 30.13, 30.11, 28.35, 28.23, 23.64, 23.45, 23.02, 22.81, 13.77, 13.70, 10.15

Th-DPP_EtHex-Ph-Benzaldehyde

In a 50 mL single-neck round-bottom flask, 1.1 grams of Th-DPP_EtHex-Ph-Br (1.84 mmol), 0.854 gram of 4-(4,4,5,5-Tetramethyl-1,3,2-dioxaborolan-2-yl)-benzaldehyde (3.68 mmol), and 0.976 gram of potassium phosphate tribasic (4.59 mmol) were dissolved in 20 mL of toluene, 0.2 mL tAmylOH, and 0.1 mL water. This solution was degassed for 20 minutes with a stream of $N_2$, after which time 10 mg of $Pd_2dba_3$ and 20 mg of X-Phos were added simultaneously, in one batch. The reaction was then brought to 80° C. for 6 hours, and then diluted with DCM and loaded directly onto a large column loaded with 500 mL of silica. A gradient eluent of 40:60 Toluene:DCM to 100% DCM was used to purify the compound. 668 mg (58% yield) of a pure red solid was obtained.

$^1$H NMR (400 MHz, Methylene Chloride-d2) δ 10.10 (s, 1H), 8.94 (dd, J=3.9, 1.1 Hz, 1H), 8.07-7.98 (m, 2H), 7.98-7.92 (m, 2H), 7.92-7.83 (m, 4H), 7.74 (dd, J=5.0, 1.2 Hz, 1H), 7.33 (dd, J=5.0, 3.9 Hz, 1H), 4.04-3.93 (m, 2H), 3.93-3.81 (m, 2H), 1.84 (p, J=6.6 Hz, 1H), 1.55-1.48 (m, 1H), 1.44-1.04 (m, 16H), 0.96-0.85 (m, 6H), 0.85-0.69 (m, 6H). $^{13}$C NMR (100 MHz, Methylene Chloride-d2) δ 191.63, 162.12, 161.94, 145.70, 142.05, 141.64, 135.76, 135.42, 131.17, 130.17, 129.32, 128.92, 128.27, 128.11, 127.69, 127.56, 125.19, 45.46, 44.94, 39.09, 38.69, 30.25, 30.16, 28.37, 28.24, 23.70, 23.46, 23.03, 22.80, 21.11, 13.77, 13.72, 10.19

BrTh-DPP_EthHex-Ph-Benzaldehyde

In a 50 mL single-neck round-bottom flask, 0.658 gram of Th-DPP_EthHex-Ph-Benzaldehyde (1.06 mmol) was dissolved in 20 mL of chloroform, and 0.198 gram NBS (1.11 mmol) was added in one batch at room temperature. This reaction was stirred for 2 hour at which point the solution was loaded directly onto a short silica column and eluted with 20:80 Tol:DCM. 211 mg (28% yield) of redish/purple solid was obtained.

$^1$H NMR (400 MHz, Methylene Chloride-d2) δ 10.07 (s, 1H), 8.66 (d, J=4.2 Hz, 1H), 8.03-7.97 (m, 2H), 7.91 (d, J=8.4 Hz, 2H), 7.89-7.79 (m, 4H), 7.28 (d, J=4.1 Hz, 1H), 3.95-3.78 (m, 4H), 1.80 (p, J=6.6 Hz, 1H), 1.52-1.45 (m, 1H), 1.43-1.00 (m, 16H), 0.87 (td, J=7.4, 1.9 Hz, 6H), 0.75 (dt, J=17.5, 7.0 Hz, 6H). $^{13}$C NMR (100 MHz, Methylene Chloride-d2) δ 191.63, 162.69, 161.86, 145.70, 141.77, 140.60, 135.32, 134.07, 131.41, 130.17, 129.31, 128.62, 127.69, 127.58, 127.69, 127.56, 125.19, 45.54, 44.99, 39.10, 38.67, 30.70, 30.23, 28.32, 28.22, 23.69, 23.47, 23.00, 22.79, 21.11, 13.77, 13.71, 10.18

HexOTPA-Th-DPP_EthHex-Ph-Benzaldehyde

The reaction and purification was performed in the same manner as for Th-DPP_EthHex-Ph-Benzaldehyde. 200 mg (62% yield) of a purple-ish solid was obtained.

$^1$H NMR (400 MHz, Methylene Chloride-d2) δ 10.07 (s, 1H), 9.06 (d, J=4.1 Hz, 1H), 8.01-7.96 (m, 2H), 7.91 (d, J=8.4 Hz, 2H), 7.89-7.79 (m, 4H), 7.52-7.47 (m, 2H), 7.38 (d, J=4.2 Hz, 1H), 7.11-7.03 (m, 4H), 6.93-6.82 (m, 6H), 4.04-3.91 (m, 6H), 3.87 (td, J=6.9, 3.8 Hz, 2H), 1.92 (p, J=6.6 Hz, 1H), 1.77 (dt, J=14.6, 6.7 Hz, 4H), 1.53-1.42 (m, 4H), 1.42-1.04 (m, 22H), 0.99-0.82 (m, 12H), 0.82-0.69 (m, 6H). $^{13}$C NMR (100 MHz, Methylene Chloride-d2) δ 191.63, 162.32, 161.75, 156.24, 151.41, 149.79, 145.76, 144.21, 142.37, 141.33, 139.63, 137.85, 135.71, 130.16, 129.29, 128.97, 127.66, 127.51, 127.24, 126.89, 126.75, 124.05, 122.66, 119.06, 115.31, 110.23, 107.32, 68.29, 45.53, 44.98, 39.21, 38.71, 31.58, 30.26, 29.26, 28.51, 28.26, 28.25, 25.69, 23.71, 23.58, 23.07, 22.81, 22.61, 13.82, 13.79, 13.73, 10.26, 10.22, 10.21

DPP07,
HexOTPA-Th-DPP_EthHex-Ph-PhenylCAA

In a 25 mL single-neck round-bottom flask, 186 mg of HexOTPA-Th-DPP_EthHex-Ph-Benzaldehyde (0.17 mmol) and 120 mg cyanoacetic acid (1.41 mmol) was dissolved in 3 mL DCM, 1.5 mL triethylamine, and 1 drop piperidine. A spatula of MgSO$_4$ was added to this reaction and then heated to 40° C. overnight. In the morning, the reaction was diluted with DCM and extracted with a water and acetic acid solution, and then pure water. Crude product was rotovapped and then loaded onto a silica column and eluted with 2:3:95 acetic acid:methanol:DCM eluent. 107 mg (55% yield) of purplish/blue solid was obtained.

$^1$H NMR (400 MHz, Methylene Chloride-d2) δ 9.06 (d, J=4.2 Hz, 1H), 8.32 (d, J=1.7 Hz, 1H), 8.16-8.10 (m, 2H), 7.91 (d, J=8.5 Hz, 2H), 7.88-7.79 (m, 4H), 7.53-7.47 (m, 2H), 7.39 (d, J=4.1 Hz, 1H), 7.13-7.04 (m, 4H), 6.92-6.83 (m, 6H), 4.04-3.91 (m, 6H), 3.91-3.83 (m, 2H), 1.91 (p, J=6.6 Hz, 1H), 1.77 (dt, J=14.6, 6.6 Hz, 4H), 1.46 (p, J=7.1 Hz, 4H), 1.41-1.03 (m, 22H), 0.97-0.81 (m, 12H), 0.81-0.70 (m, 6H). C64H78N4O6S2[M+] Exact Mass=1132.6112, MS (MALDI)=1132.6071

Figure 3:
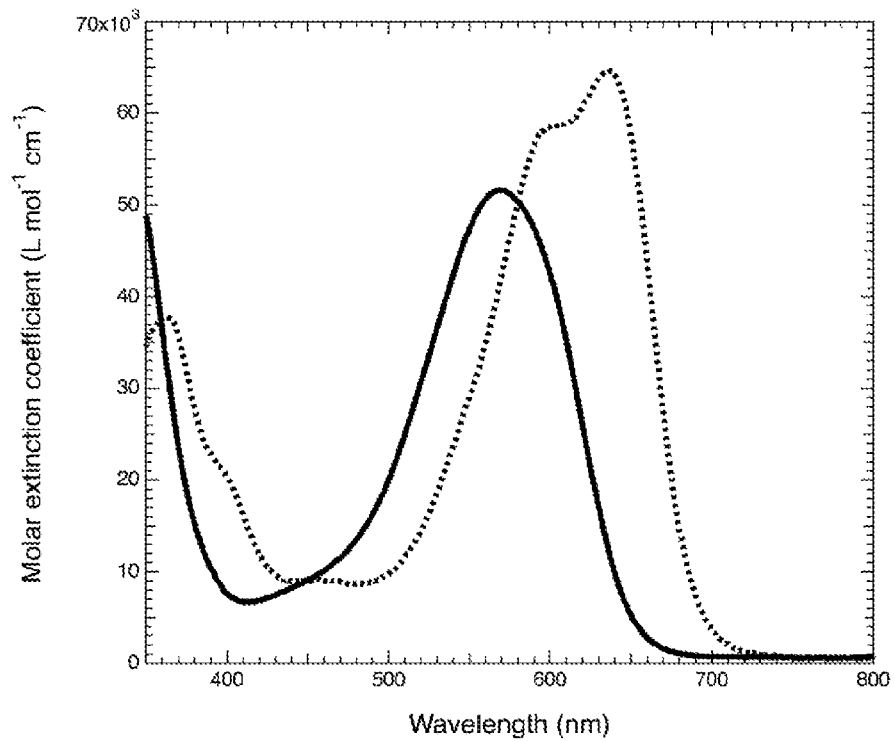
FIG. 3 shows UV-Vis absorption spectra of DPP03 (dotted line) and DPP07 (solid line) in THF.

The maximum absorbance of the sensitizer was observed at ~560 nm, which was ~80 nm blue-shifted compared to DPP03 (FIG. 3). The hypsochromic shift for DPP07 is explained by the increased dihedral twist at the DPP-Phenyl bond, the increased aromatic stabilization energy of the phenyl group, and the decreased electron donating strength of phenyl compared to thiophene.

Electrochemical features were characterized with cyclic voltammetry measurements in a 0.1 M DMF solution of tetra-n-butylammonium hexafluorophosphate. Platinum counter and reference electrodes were used with a glassy carbon working electrode. The ground-state oxidation potential (E(S$^+$/S)) was determined to be 0.29 V vs. Fc+/Fc, corresponding to 0.98 V vs. the normal hydrogen electrode (NHE) (using E$_0$(Fc+/Fc)=0.69 V vs. NHE). The reduction potential (Ered) was determined to be −0.87 vs. NHE. Given the HOMO-LUMO gap (E(0,0)) taken from the onset of the absorbance, ~1.90 eV, the corresponding excited state oxidation potentials (E(S$^+$/S*)) is calculated to be −0.92 V vs. NHE.

Synthesis of Compound of Formula (71)
Corresponding to Co-Sensitizer NT35

Figure 13:
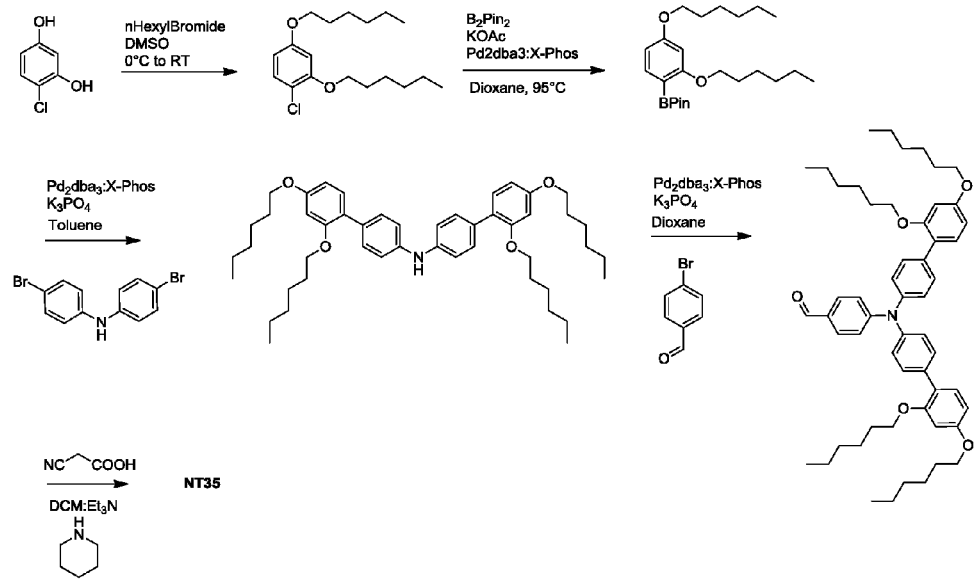
FIG. 13 shows the general scheme for the synthesis of compound of formula (71) referred also as NT35.

The general scheme for the synthesis of NT35 is shown in FIG. 13.

Bishexyloxy-4-chloro-resorcinol

In a 100 mL single-neck round-bottom flask, 10.00 grams of 4-chlororesorcinol (69.18 mmol) and 9.7 grams of potassium hydroxide (172.87 mmol) were dissolved in 70 mL of DMSO. This solution was cooled to 0° C. 34.26 grams of n-Hexylbromide (207.55 mmol) was then added via syringe. After stirring for 30 minutes at 0° C., the reaction was removed from the ice-bath and allowed to warm to RT overnight. The reaction was extracted with hexanes and washed with plenty of water. Silica gel chromatography with 100% hexanes was performed until the product started to elute, and then the eluent was increased in polarity to 20:80 DCM:Hexanes until all the product was eluted. 20 grams (93% yield) of a pure clear oil was obtained.

$^1$H NMR (400 MHz, Methylene Chloride-d2) δ 7.21 (d, J=8.7 Hz, 1H), 6.52 (d, J=2.8 Hz, 1H), 6.42 (dd, J=8.7, 2.7 Hz, 1H), 3.99 (t, J=6.6 Hz, 2H), 3.92 (t, J=6.6 Hz, 2H), 1.90-1.69 (m, 4H), 1.51-1.42 (m, 4H), 1.41-1.28 (m, 8H), 0.99-0.86 (m, 6H). $^{13}$C NMR (100 MHz, Methylene Chloride-d2) δ 159.06, 155.20, 129.87, 113.92, 105.76, 101.26, 69.02, 68.32, 31.60, 31.54, 29.21, 29.04, 25.68, 25.62, 22.63, 22.61, 13.82, 13.81

2-(2,4-bis(hexyloxy)phenyl)-4,4,5,5-tetramethyl-1,3,2-dioxaborolane

In a 100 mL single-neck round-bottom flask, 8.56 grams of bishexyloxy-4-chloro-resorcinol (27.36 mmol), 10.42 grams of Bis(pinacolato)diboron (41.03 mmol), and 8.06 grams potassium acetate (82.12 mmol) were dissolved in 60 mL of dioxane. This solution was degassed for 20 minutes with a stream of N2, after which time 10 mg of Pd2dba3 and 20 mg of X-Phos were added simultaneously, in one batch. The reaction was then brought to 95° C. for 10 hours. The reaction was then cooled to RT, and plugged through a thin pad of MgSO$_4$ with DCM. The crude product was purified with gradient silica gel chromatography: 100% hexanes to 20:80 Hex:DCM. 6.23 grams (70% yield) of a pure clear oil was obtained.

$^1$H NMR (400 MHz, Methylene Chloride-d2) δ 7.54 (d, J=8.2 Hz, 1H), 6.46 (dd, J=8.2, 2.2 Hz, 1H), 6.40 (d, J=2.2 Hz, 1H), 3.96 (dt, J=14.4, 6.4 Hz, 4H), 1.85-1.72 (m, 4H), 1.61-1.42 (m, 4H), 1.41-1.34 (m, 8H), 1.32 (s, 12H), 0.99-0.86 (m, 6H). $^{13}$C NMR (100 MHz, Methylene Chloride-d2) δ 165.58, 163.11, 137.71, 129.65, 105.10, 99.20, 83.17, 82.81, 68.20, 67.88, 31.66, 31.58, 29.32, 29.20, 25.68, 25.67, 24.83, 24.64, 22.71, 22.60, 13.88, 13.80.

Bis(2',4'-bis(hexyloxy)-[1,1'-biphenyl]-4-yl)amine

In a 25 mL single-neck round-bottom flask, 1.5 grams of bis(4-bromophenyl)amine (4.59 mmol), 3.99 grams of 2-(2,4-bis(hexyloxy)phenyl)-4,4,5,5-tetramethyl-1,3,2-dioxaborolane (9.86 mmol), and 2.92 grams potassium acetate (13.76 mmol) were dissolved in 10 mL of toluene, 0.2 mL tAmylOH, and 0.1 mL water. This solution was degassed for 20 minutes with a stream of N2, after which time 10 mg of Pd2dba3 and 20 mg of X-Phos were added simultaneously, in one batch. The reaction was then brought to 80° C. for 10 hours. The reaction was then cooled to RT, and plugged through a thin pad of MgSO4 with DCM. The crude product was purified with silica gel chromatography: 10:90 Et$_2$O: Hex. 2.26 grams (68% yield) of a pure clear oil, which solidifies in time to a grey wax, was obtained.

$^1$H NMR (400 MHz, Methylene Chloride-d2) δ 7.44 (d, J=8.3 Hz, 4H), 7.22 (d, J=8.2 Hz, 2H), 7.12 (d, J=8.3 Hz, 4H), 6.54 (d, J=7.5 Hz, 4H), 5.88 (s, 1H), 3.98 (dt, J=9.7, 6.6 Hz, 8H), 1.77 (tt, J=14.7, 6.8 Hz, 8H), 1.47 (qd, J=13.4, 11.7, 6.9 Hz, 8H), 1.35 (dh, J=14.4, 3.7 Hz, 16H), 0.92 (dt, J=10.5, 6.7 Hz, 12H). $^{13}$C NMR (100 MHz, Methylene Chloride-d2) δ 159.48, 156.94, 141.53, 131.08, 130.61, 130.26, 123.01, 116.95, 105.33, 100.17, 68.33, 68.12, 31.65. 31.51, 29.33, 29.15, 25.81, 25.76, 22.66, 22.62, 13.85, 13.84

4-(bis(2',4'-bis(hexyloxy)-[1,1'-biphenyl]-4-yl)amino)benzaldehyde

In a 25 mL single-neck round-bottom flask, 0.269 gram of 4-bromobenzaldehyde (1.45 mmol), 10.42 grams of Bis(2',4'-bis(hexyloxy)-[1,1'-biphenyl]-4-yl)amine (1.38 mmol), and 0.587 gram tribasic potassium phosphate (2.76 mmol) were dissolved in 6 mL of dioxane. This solution was degassed for 20 minutes with a stream of N2, after which time 10 mg of Pd2dba3 and 20 mg of X-Phos were added simultaneously, in one batch. The reaction was then brought to 75° C. for 10 hours. The reaction was then cooled to RT, and plugged through a thin pad of MgSO$_4$ with DCM. The crude product was purified with gradient silica gel chromatography: a gradient from 100% hexanes to 100% DCM. 1.05 grams (83% yield) of a pure yellow oil was obtained.

$^1$H NMR (400 MHz, Methylene Chloride-d2) δ 9.82 (s, 1H), 7.75-7.67 (m, 2H), 7.60-7.53 (m, 4H), 7.33-7.19 (m, 6H), 7.15-7.10 (m, 2H), 6.62-6.51 (m, 4H), 4.01 (td, J=6.5, 4.4 Hz, 8H), 1.87-1.70 (m, 8H), 1.53-1.26 (m, 24H), 1.02-0.80 (m, 12). 13C NMR (10 MHz, Methylene Chloride-d2) δ 190.03, 159.92, 156.97, 153.36, 144.15, 135.47, 131.01, 130.81, 130.57, 128.94, 125.65, 122.24, 119.05, 105.42, 100.10, 68.36, 68.12, 31.59, 31.43, 29.26, 29.05, 25.74, 25.70, 22.62, 22.56, 13.80, 13.78.

Preparation of Dye Solar Cells Comprising a Compound of the Invention, the Compound of Formula (72) also Referred as DPP07, Only, and With Co-Sensitizer NT 35 or D35

The TiO$_2$ transparent electrodes composed of ~20 nm anatase on fluorine doped thin oxide (FTO) conducting glass were controlled to get a desired thickness by the number of screen printing passes. A 4~5 µm thick light-scattering layer consisting of 400 nm sized TiO$_2$ particles was printed on the top of the transparent layer to increase light path length by scattering. Platinized FTO glass was used as the counter electrode, as disclosed in Yum, J. H.; Jang, S. R.; Humphry-Baker, R.; Gratzel, M.; Cid, J. J.; Tones, T.; Nazeeruddin, M. K. Langmuir 2008, 24, 5636).

The TiO$_2$ film was stained with an organic dye (compound of formula (72), DPP07) by immersing it into a 0.025 mM solution of DPP07 with 2.5 mM 3α,7α-dihydroxy-5β-cholic acid (chenodeoxycholic acid) in 4-tert-butanol/acetonitrile mixture (1:1 v/v). The film was co-adsorbed with the co-sensitizer by immersing it into a solution containing DPP07 and co-sensitizer.

Devices were fabricated with TiO$_2$ thickness of ~7.5+5 (20 nm and 400 nm particles) µm, with electrolyte composition 0.6M DMII, 0.05M LiI, 0.03M I$_2$, 0.25M TBP, 0.05M GuSCN in Acetonitrile:Valeronitrile (85:15). All performance data are measured after ~24 hrs. 2.5 mM of CDCA is contained in the dye solution of DPP07, DPP07 with co-dye NT35 or with co-dye D35.

For photovoltaic measurements of the DSCs, the irradiation source was a 450 W xenon light source (Osram XBO 450, Germany) with a filter (Schott 113), whose power was regulated to the AM 1.5 G solar standard by using a reference Si photodiode equipped with a colour matched filter (KG-3, Schott) in order to reduce the mismatch in the region of 350-750 nm between the simulated light and AM 1.5 G to less than 4%. The measurement of incident photon-to-current conversion efficiency (IPCE) was plotted as a function of excitation wavelength by using the incident light from a 300 W xenon lamp (ILC Technology, USA), which was focused through a Gemini-180 double monochromator (Jobin Yvon Ltd.).

Figure 4:
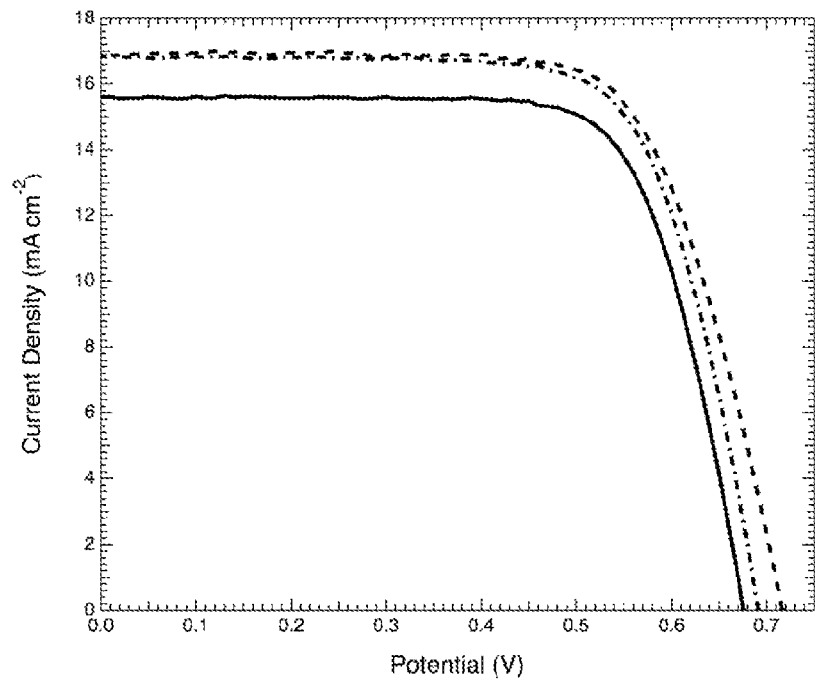
FIG. 4 shows photovoltaic characteristics of DSCs comprising DPP07 corresponding to the compound of the invention of formula (72) as a dye or sensitizer under 1 sun (100 mW cm$^{-2}$). Solid line corresponds to DSC comprising the single dye DPP07. Dash-dotted line corresponds to DSC comprising DPP07 with co-sensitizer NT35 corresponding to compound of formula (71). Dashed line corresponds to DSC comprising DPP07 with co-dye or co-sensitizer D35 (CAS number 1197992-37-2).
Figure 5:
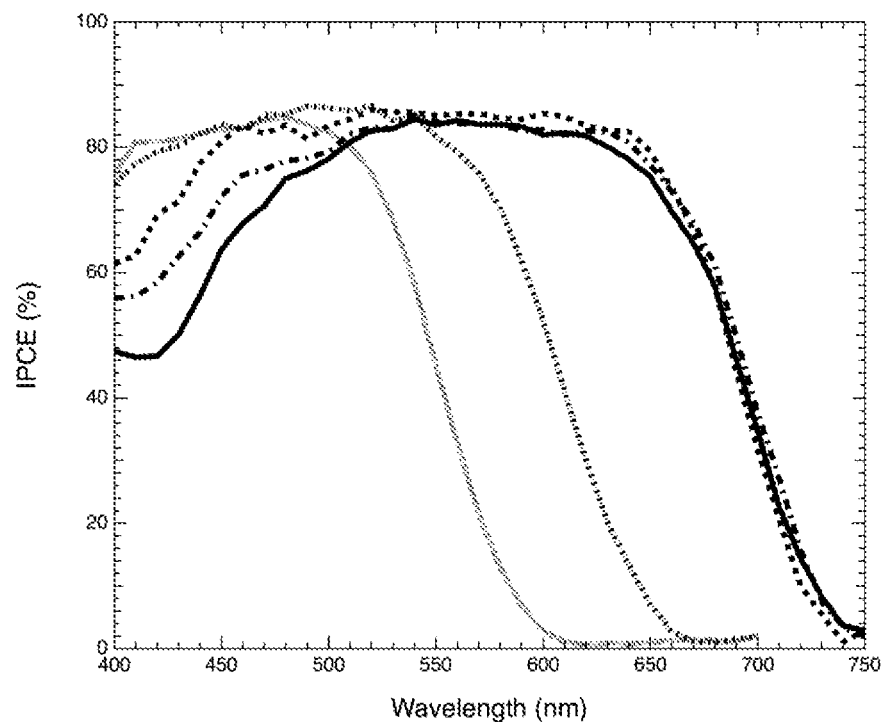
FIG. 5 shows IPCEs of DSCs comprising DPP07 as single dye device (solid black line), as dye with co-sensitizer NT35 (dash-dotted black line), and as dye with D35 (dotted black line). IPCE of a solar cell comprising NT35 without DPP07 is indicated by grey hatched line. IPCE of a solar cell comprising D35 without DPP07 is indicated by hatch-dotted line.

The results presented in Table 1 and FIG. 4 show that the DPP07 sensitized solar cells generated a PCE of ~7.7% and exhibited over 80% incident photon-to-electron conversion efficiency (IPCE) from 500 to 640 nm (FIG. 5).

TABLE 1

Performance of DSC devices comprising DPP07 sensitizer only or with co-sensitizer or co-dye NT35 or D35.

| Dye | Co-dye | J$_{sc}$ (mA/cm$^2$) | V$_{oc}$ (V) | FF | PCE (%) |
|---|---|---|---|---|---|
| DPP07 | | 15.6 | 0.68 | 0.73 | 7.67 |
| DPP07 | NT35 | 16.9 | 0.69 | 0.71 | 8.31 |
| DPP07 | D35 | 17.0 | 0.72 | 0.70 | 8.60 |
| NT35 | | 8.70 | 0.79 | 0.74 | 5.05 |
| D35 | | 12.2 | 0.76 | 0.71 | 6.56 |

In the solution of DPP07 dye, 2.5 mM of CDCA is contained.

Compared to 5.03%, the performance with DPP03 (FIG. 6), it is apparent that the DPP07-based solar cells outperform the DPP03 sensitized solar cell (see IV curves comparison in FIG. 6). Despite the decreased spectral breadth of DPP07 compared to DPP03, the asymmetric nature of DPP07 yielded increased IPCE and ultimately higher performance: DPP03 sensitized solar cells exhibited an IPCE extending to a longer wavelengths, close to 800 nm, but fewer photons were converted to photocurrent. The reason for the higher performance in DPP07 sensitized solar cell is mainly a result of linear current generation with light intensity. FIG. 6 shows the current dynamics as function of light intensity, which displays the individual photocurrents normalized to 1 sun J$_{sc}$.

The photocurrent from the DPP07 sensitized solar cell shows exceptional linearity, achieving a plateau at intensities between 0.01 and 1 sun, compared to the DPP03 solar cell which fails to plateau. It is noted that the presence of CDCA improved the current linearity for both sensitizers. This linearity is likely ascribed to less aggregation for DPP07, as the asymmetric DPP bridge/core could impede π-π interactions between the sensitizers. Further work is underway concerning this aggregation, because it follows a reverse light intensity dependence.

Figure 7:
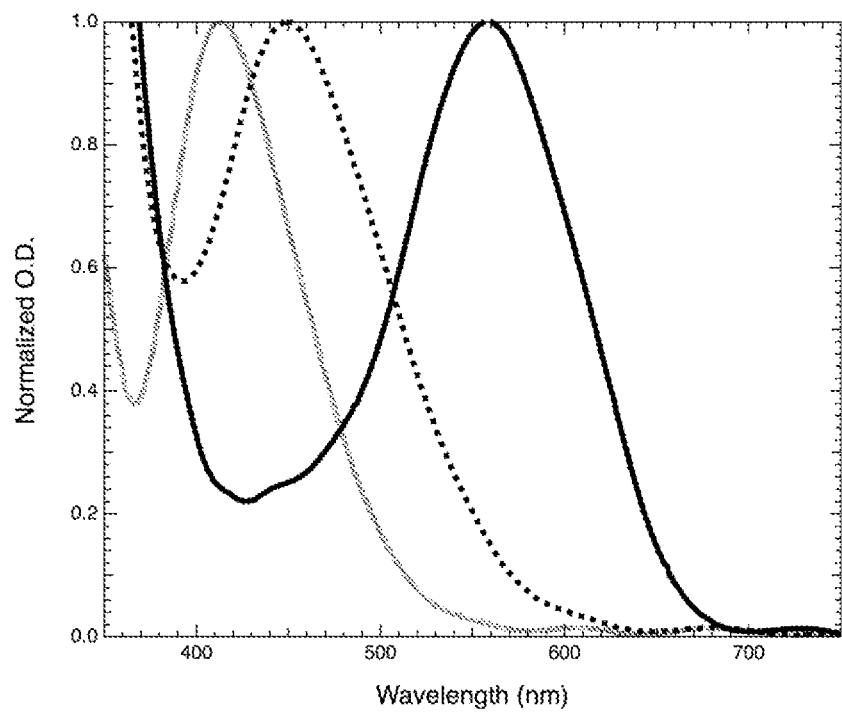
FIG. 7 shows normalized UV-Vis absorption spectra of NT35 (hatched line), D35 (dotted line) and DPP07 (solid line) on 2 μm thick TiO$_2$ film.

To realize the full potential of this relatively low-bandgap sensitizer, a wide-bandgap co-sensitizer was utilized to eke out more current from the high energy photons, as well as to aid in surface coverage leading to improved $V_{oc}$. The PCE is improved to over 8.30% for photovoltaic devices utilizing the new co-sensitizer NT35 as well as with D35. NT35 has its maximum absorbance at ~415 nm on the TiO$_2$ surface, which is ~35 nm blue shifted when compared to D35 (FIG. 7). Despite the ostensibly greater spectral complementarity of NT35 with DPP07, the highest PCE was achieved for DPP07 in combination with D35, due to improved $V_{oc}$ and $J_{sc}$. The wide-bandgap sensitizers substantially increased the high-energy visible light absorption from 400-550 nm, broadening the IPCE spectra of the co-sensitized photovoltaic devices when compared to the DPP07 single-sensitizer devices. The IPCEs of co-sensitized devices maintained high efficiencies even at low energy wavelengths and they (particularly DPP07/D35) show nearly-ideal panchromatic shapes from 400-750 nm.

Figure 8:
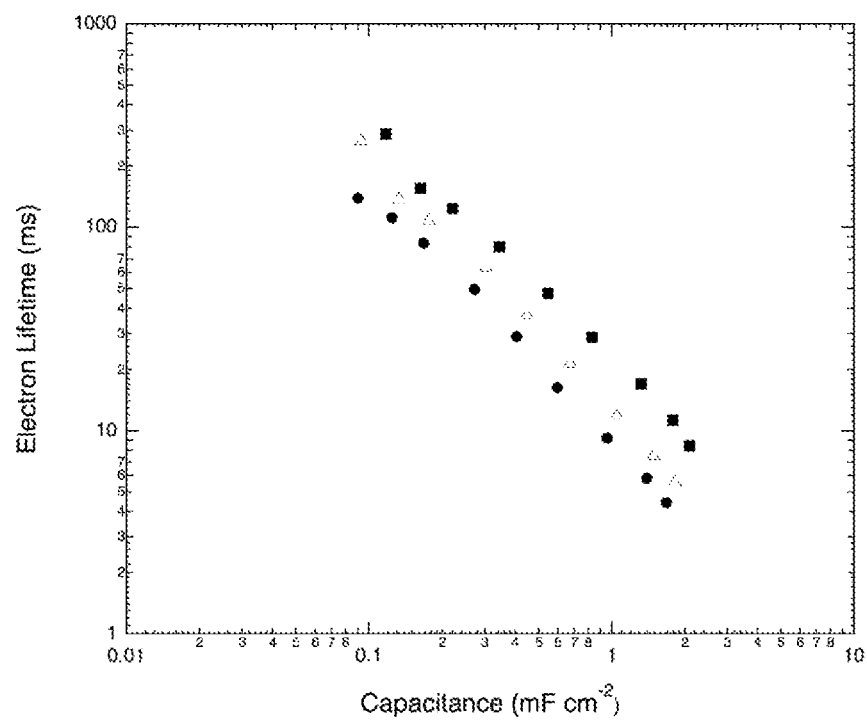
FIG. 8 shows electron lifetime of solar cells comprising DPP07 (closed circles) only with CDCA, or DPP07 with NT35 (white triangles) in presence of CDCA, or DPP07 with D35 (closed squares in presence of CDCA.
Figure 9:
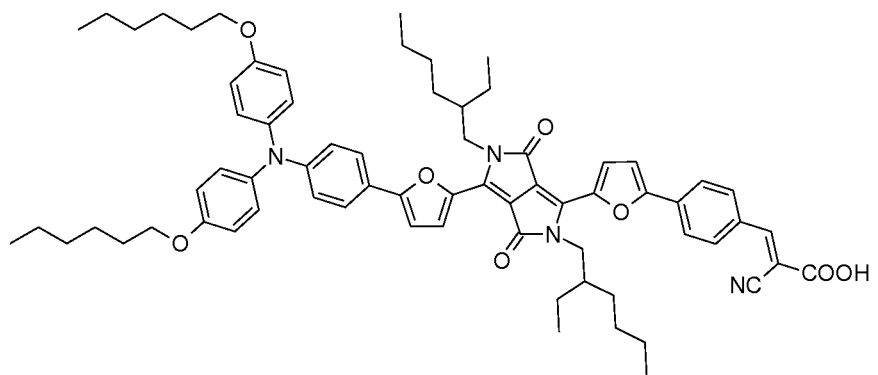
FIG. 9 shows a compound of formula (I), named or referred to DPP09, wherein Ar$_1$ and Ar$_2$ are identical aromatic aryl groups.
Figure 10:
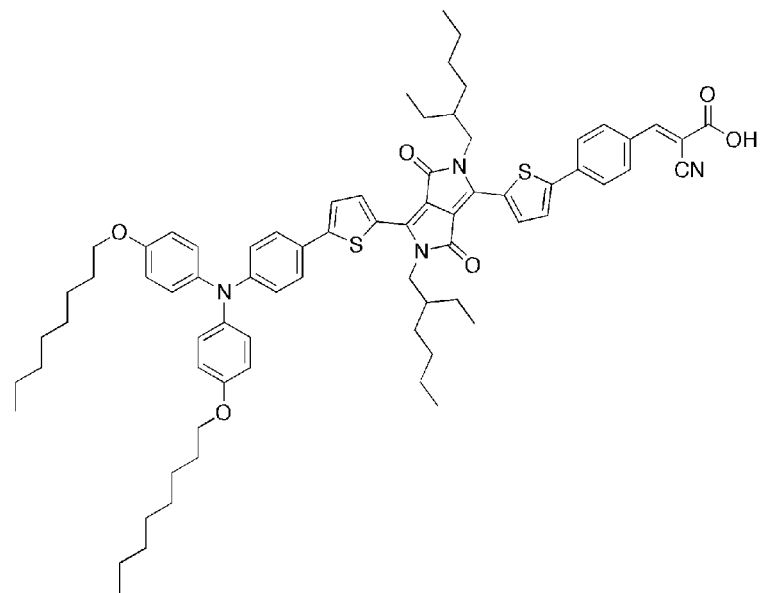
FIG. 10 shows a compound of formula (I), named or referred to DPP03, wherein Ar$_1$ and Ar$_2$ are identical aromatic aryl groups.
Figure 11:
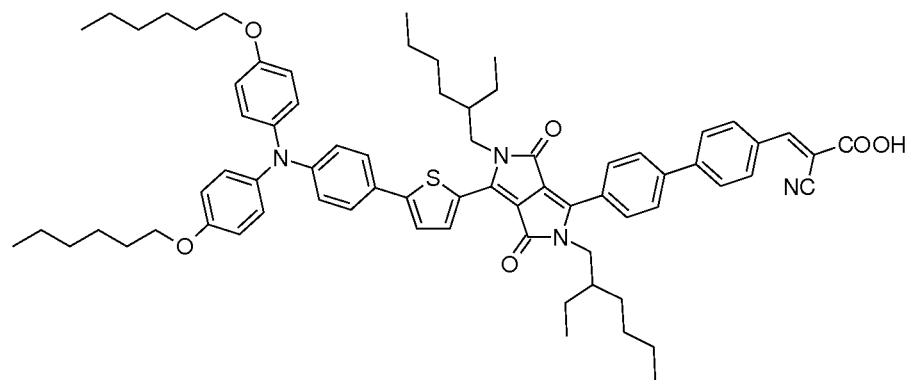
FIG. 11 shows the compound of formula (72) corresponding to the compound of formula (I) named or referred to DPP07, wherein Ar$_1$ and Ar$_2$ are different aromatic aryl groups.

Interestingly, the $V_{oc}$s of co-sensitized cells, particularly DPP07/D35 were improved. The increase is likely due to an increase in electron lifetime in presence of the wide bandgap sensitizer (FIG. 8). The increased lifetime is plausibly ascribed to either a functional group, dihexyloxybiphenyl at the donor ligand or passivation by wide-bandgap dyes acting as co-adsorbent20. Ultimately, a peak DPP07/D35 co-sensitized solar cell achieved 8.6% power conversion efficiency, improved from 7.7% obtained by DPP07 single-sensitizer solar cell, due to an increase in both $V_{oc}$ and $J_{sc}$.

A remarkable IPCE exceeding 80% across the visible light region was achieved with this asymmetric core, leading to a maximum power conversion efficiency of 7.7% for the single dye DPP07. This improvement over DPP03, sensitizer based on a symmetric DPP core comes as a result of increased photocurrent, despite a hypsochromic shift in the spectral absorbance. The asymmetric Th-DPP-Ph-based sensitizer for DSC applications reveals a balanced approach to DPP design, maximizing spectral response and IPCE. This asymmetric approach is expected to yield higher performance sensitizers with the use of stronger donating groups to maximize light absorption. The use of a wide-bandgap co-sensitizer to eke out greater current density from the high-energy region of the solar spectrum yielded an ultimate PCE of 8.6% at AM 1.5.

Example 2

Synthesis of Compounds of Formulae (77) Referred as DPP13, (75) Referred as DPP14, (88) Referred as DPP15 and (74) Referred as DPP17

3-(4-bromophenyl)-2,5-bis(2-ethylhexyl)-6-(thiophen-2-yl)pyrrolo[3,4-c]pyrrole-1,4(2H,5H)-dione (Th-DPP_EtHex-Ph-Br) was synthesized as above mentioned.

Th-DPP EtHex-Ph-Furaldehyde

In a 50 mL single-neck round-bottom flask, 1.00 grams of Th-DPP_EtHex-Ph-Br (1.67 mmol), 0.28 grams of 5-Formylfuran-2-boronic acid (2.00 mmol), and 1.15 grams of potassium carbonate (8.35 mmol) were dissolved in 4 mL of toluene and 2 mL MeOH. This solution was degassed for 20 minutes with a stream of N$_2$, after which time 10 mg of Pd(dppf)Cl$_2$ was added. The reaction was then brought to 70° C. for 1 hour, and then diluted with DCM and plugged through a thin pad of MgSO$_4$ with DCM. Volatile organics were removed and the crude compound loaded onto a medium column loaded with 200 mL of silica. A gradient eluent of 1% EtOAc to 3% EtOAc in hexanes was used to purify the compound. 0.87 grams (85% yield) of a pure, deep-red solid was obtained.

$^1$H NMR (400 MHz, Methylene Chloride-d2) δ 9.70 (s, 1H), 8.93 (dd, J=3.9, 1.2 Hz, 1H), 7.99 (d, J=8.5 Hz, 2H), 7.92 (d, J=8.5 Hz, 2H), 7.74 (dd, J=5.1, 1.1 Hz, 1H), 7.39 (d, J=3.8 Hz, 1H), 7.35-7.30 (m, 1H), 7.03 (d, J=3.7 Hz, 1H), 4.04-3.94 (m, 2H), 3.94-3.80 (m, 2H), 1.84 (p, J=6.4 Hz, 1H), 1.51 (p, J=6.5 Hz, 1H), 1.45-1.03 (m, 16H), 0.93-0.84 (m, 6H), 0.84-0.70 (m, 6H). $^{13}$C NMR (100 MHz, Methylene Chloride-d2) δ 177.80, 162.68, 162.49, 158.58, 153.13, 145.81, 142.84, 136.13, 131.87, 131.28, 130.37, 130.18, 129.87, 128.88, 125.85, 110.85, 109.67, 108.54, 46.08, 45.61, 39.69, 39.68, 39.30, 39.28, 30.84, 30.83, 30.75, 30.73, 30.26, 28.95, 28.83, 24.25, 24.08, 23.61, 23.39, 14.35, 14.26, 10.77, 10.75.

Br-Th-DPP_EthHex-Ph-Furaldehyde

In a 50 mL single-neck round-bottom flask, 800 mg of Th-DPP_EtHex-Ph-Furaldehyde (1.31 mmol) was dissolved in 20 mL of chloroform, and 243 mg NBS (1.37 mmol) was added in one batch at room temperature. This reaction was stirred for 2 hour at which point the solution was loaded directly onto a short silica column and a gradient eluent of 1% EtOAc to 3% EtOAc in hexanes was used to purify the compound. 496 mg (55% yield) of purple solid was obtained.

$^1$H NMR (400 MHz, Methylene Chloride-d2) δ 9.70 (s, 1H), 8.69 (d, J=4.2 Hz, 1H), 8.04-7.96 (m, 2H), 7.96-7.89 (m, 2H), 7.39 (d, J=3.8 Hz, 1H), 7.31 (d, J=4.2 Hz, 1H), 7.03 (d, J=3.8 Hz, 1H), 4.00-3.82 (m, 4H), 1.89-1.78 (m, 1H), 1.53-1.47 (m, 1H), 1.43-1.03 (m, 16H), 0.94-0.83 (m, 6H), 0.83-0.67 (m, 6H). $^{13}$C NMR (100 MHz, Methylene Chloride-d2) δ 177.78, 162.40, 158.48, 153.14, 146.34, 141.37, 135.98, 131.97, 131.84, 131.37, 130.03, 129.86, 125.81, 119.71, 110.71, 109.68, 108.80, 46.08, 45.61, 39.69, 39.68, 39.30, 39.28, 30.84, 30.83, 30.75, 30.73, 30.26, 28.95, 28.83, 24.25, 24.08, 23.61, 23.39, 14.35, 14.26, 10.77, 10.75.

HexOTPA-Th-DPP_EthHex-Ph-Furaldehyde

In a 25 mL single-neck round-bottom flask, 400 mg of Br-Th-DPP_EthHex-Ph-Furaldehyde (0.58 mmol), 375 mg of N,N-bis[4-(hexyloxy)phenyl]-4-(4,4,5,5-tetramethyl-1,3,2-dioxaborolan-2-yl)-benzamine (0.66 mmol), and 368 mg of potassium phosphate tribasic (1.73 mmol) were dissolved in 12 mL of toluene, 1 mL tAmylOH, and 0.5 mL water. This solution was degassed for 20 minutes with a stream of N$_2$, after which time 10 mg of Pd$_2$dba$_3$ and 20 mg of X-Phos were added simultaneously, in one batch. The reaction was then brought to 80° C. for 6 hours, and then diluted with DCM and plugged through a thin pad of MgSO$_4$ with DCM. Volatile organics were removed and the crude compound loaded onto a medium column of approx. 200 mL of silica. A gradient eluent of 100% DCM to 3% EtOAc in DCM was used to purify the compound. 495 mg (81% yield) of a pure purple/blue solid was obtained.

$^1$H NMR (400 MHz, Methylene Chloride-d2) δ 9.69 (s, 1H), 9.09 (d, J=4.2 Hz, 1H), 8.03-7.87 (m, 4H), 7.70-7.66 (m, 1H), 7.51 (d, J=8.8 Hz, 2H), 7.45 (dd, J=5.0, 2.0 Hz, 1H), 7.11 (d, J=8.8 Hz, 4H), 7.01 (d, J=3.7 Hz, 1H), 6.96-6.84 (m, 6H), 4.08-3.92 (m, 6H), 3.92-3.81 (m, 2H), 2.01-1.85 (m, 1H), 1.85-1.72 (m, 4H), 1.72-1.64 (m, 1H), 1.55-1.44 (m, 4H), 1.44-1.03 (m, 24H), 1.02-0.84 (m, 12H), 0.84-0.71 (m, 6H). $^{13}$C NMR (100 MHz, Methylene Chloride-d2) δ 177.18, 162.28, 161.69, 158.09, 156.25, 152.48, 151.57, 149.81, 147.72, 146.31, 143.70, 142.83, 142.55, 139.63, 138.03, 132.59, 132.56, 131.53, 131.47, 130.41, 130.37, 129.80, 129.24, 128.91, 128.31, 127.65, 127.24, 126.85, 126.76, 126.15, 125.45, 125.21, 124.04, 122.69, 120.25, 119.05, 115.32, 110.47, 108.97, 107.33, 68.29, 45.55, 45.03, 39.20, 38.70, 34.88, 34.73, 34.12, 31.59, 31.02, 30.87, 30.50, 30.49, 30.24, 29.62, 29.50, 29.27, 28.49, 28.24, 27.62, 27.51, 27.35, 27.26, 26.44, 26.43, 25.70, 25.47, 23.80, 23.66, 23.59, 23.08, 22.81, 22.61, 22.60, 13.83, 13.81, 13.69, 10.28, 10.18.

DPP13,
HexOTPA-Th-DPP_EthHex-Ph-FuranylCAA

In a 25 mL single-neck round-bottom flask, 200 mg of HexOTPA-Th-DPP_EthHex-Ph-Furaldehyde (0.18 mmol) and 200 mg cyanoacetic acid (2.35 mmol) was dissolved in 10 mL DCM, 5 mL triethylamine, and 0.2 mL piperidine. A spatula of MgSO$_4$ was added to this reaction and then heated to 40° C. overnight. In the morning, the reaction was diluted with DCM and extracted with a water and acetic acid solution, and then pure water. Crude product was rotovapped and then loaded onto a silica column and eluted with 2:3:95 acetic acid:methanol:DCM eluent. 119 mg (56% yield) of blue solid was obtained.

$^1$H NMR (600 MHz, Methylene Chloride-d2) δ 8.11-8.05 (m, 5H), 8.03 (s, 1H), 7.56-7.52 (m, 2H), 7.49 (dd, J=4.3, 1.5 Hz, 1H), 7.44 (d, J=3.8 Hz, 1H), 7.27 (d, J=3.7 Hz, 1H), 7.09-7.03 (m, 4H), 6.92-6.84 (m, 6H), 4.08-3.92 (m, 8H), 1.96 (p, J=6.5 Hz, 1H), 1.80-1.75 (m, 4H), 1.55 (q, J=6.2 Hz, 1H), 1.53-1.46 (m, 4H), 1.44-1.33 (m, 14H), 1.33-1.24 (m, 4H), 1.15 (t, J=3.2 Hz, 6H), 0.96-0.88 (m, 8H), 0.87 (t, J=6.8 Hz, 4H), 0.83-0.77 (m, 3H), 0.74 (t, J=7.4 Hz, 3H). $^{13}$C NMR (100 MHz, Methylene Chloride-d2) δ 177.18, 162.28, 161.69, 158.09, 156.25, 152.48, 151.57, 149.81, 147.72, 146.31, 143.70, 142.83, 142.55, 139.63, 138.03, 132.59, 132.56, 131.53, 131.47, 130.41, 130.37, 129.80, 129.24, 128.91, 128.31, 127.65, 127.24, 126.85, 126.76, 126.15, 125.45, 125.21, 124.04, 122.69, 120.25, 119.05, 115.32, 110.47, 108.97, 107.33, 68.29, 45.55, 45.03, 39.20, 38.70, 34.88, 34.73, 34.12, 31.59, 31.02, 30.87, 30.50, 30.49, 30.24, 29.62, 29.50, 29.27, 28.49, 28.24, 27.62, 27.51, 27.35, 27.26, 26.44, 26.43, 25.70, 25.47, 23.80, 23.66, 23.59, 23.08, 22.81, 22.61, 22.60, 13.83, 13.81, 13.69, 10.28, 10.18. $C_{70}H_{82}N_4O_7S[M^+]$ Exact Mass=1122.5904, MS (MALDI)=1122.5890

7-bromo-4-(p-tolyl)-1,2,3,3a,4,8b-hexahydrocyclopenta [b]indole (TolIndoline-Br) was synthesized as previously reported in J. Mater. Chem. (2012), 22, 10771-10778.

7-(4,4,5,5-tetramethyl-1,3,2-dioxaborolan-2-yl)-4-(p-tolyl)-1,2,3,3a,4,8b-hexahydrocyclopenta[b]indole (TolIndoline-BPin)

In a 25 mL single-neck round-bottom flask, 1.20 grams of TolIndoline-Br (3.66 mmol), 1.39 grams of B$_2$Pin$_2$ (5.59 mmol), and 1.09 grams of potassium acetate (11.1 mmol) were dissolved in 10 mL of dioxane. This solution was degassed for 20 minutes with a stream of N$_2$, after which time 25 mg of Pd$_2$dba$_3$ and 50 mg of X-Phos were added simultaneously, in one batch. The reaction was then brought to 80° C. overnight, and then diluted with DCM and plugged through a thin pad of MgSO$_4$ with DCM. Volatile organics were removed and the crude compound loaded onto silica gel column. Purification was performed with a 50/50 DCM/Hexanes eluent. 1.15 grams (83% yield) of a pale yellow oil (store in the freezer) were obtained.

$^1$H NMR (400 MHz, Methylene Chloride-d2) δ 7.50 (s, 1H), 7.44 (dd, J=8.0, 1.2 Hz, 1H), 7.24-7.16 (m, 4H), 6.83 (d, J=8.0 Hz, 1H), 4.82 (ddd, J=8.7, 6.2, 2.2 Hz, 1H), 3.83 (td, J=8.8, 2.7 Hz, 1H), 2.35 (s, 3H), 2.13-1.62 (m, 6H), 1.33 (s, 12H). $^{13}$C NMR (100 MHz, Methylene Chloride-d2) δ 150.71, 139.91, 134.82, 134.18, 131.86, 130.82, 129.64, 120.50, 106.37, 83.10, 68.97, 45.13, 35.14, 33.57, 26.90, 24.70, 24.57, 24.30, 22.64, 20.47, 13.87.

TolIndoline-Th-DPP_EthHex-Ph-Furaldehyde

The reaction and purification were performed in the same manner as for the synthesis of HexOTPA-Th-DPP_EthHex-Ph-Furaldehyde, with the coupling partner TolIndoline-BPin. 196 mg (79% yield) of a blue solid.

$^1$H NMR (400 MHz, Methylene Chloride-d2) δ 9.69 (s, 1H), 9.10 (dd, J=4.2, 1.6 Hz, 1H), 7.97 (d, J=8.6 Hz, 2H), 7.94-7.89 (d, J=8.5 Hz, 2H), 7.47 (s, 1H), 7.42 (d, J=8.3, 1H), 7.38 (dd, J=4.0, 2.7 Hz, 2H), 7.25-7.19 (m, 4H), 7.01 (d, J=3.7 Hz, 1H), 6.88 (d, J=8.4 Hz, 1H), 4.95-4.84 (m, 1H), 4.13-3.95 (m, 2H), 3.94-3.81 (m, 5H), 2.36 (s, 3H), 2.18-1.48 (m, 6H), 1.43-1.05 (m, 18H), 0.97-0.69 (m, 12H). $^{13}$C NMR (100 MHz, Methylene Chloride-d2) δ 177.16, 162.35, 161.63, 158.13, 152.78, 152.45, 149.27, 143.18, 142.74, 139.46, 138.26, 136.12, 132.34, 130.25, 129.89, 129.78, 129.22, 125.98, 125.96, 125.19, 122.90, 122.50, 121.89, 120.59, 120.58, 110.49, 108.92, 107.16, 107.01, 69.38, 45.53, 45.14, 45.00, 39.24, 39.22, 38.69, 35.20, 33.47, 33.46, 30.25, 28.64, 28.25, 26.89, 24.31, 23.65, 23.58, 23.14, 23.12, 22.82, 20.52, 13.90, 13.88, 13.70, 10.28, 10.24, 10.19.

DPP14,
TolIndoline-Th-DPP_EthHex-Ph-FuranylCAA

The reaction and purification were performed in the same manner as for the synthesis of DPP13. 50 mg (65% yield) of a blue/green solid.

$^1$H NMR (600 MHz, Methylene Chloride-d2) δ 9.14 (dd, J=4.2, 1.6 Hz, 1H), 8.07 (s, 1H), 8.04 (d, J=8.5 Hz, 2H), 7.96 (d, J=8.5 Hz, 2H), 7.50 (s, 1H), 7.45 (dd, J=8.3, 2.0 Hz, 1H), 7.41 (d, J=4.1 Hz, 1H), 7.33 (d, J=3.8 Hz, 1H), 7.28-7.20 (m, 4H), 7.09 (d, J=3.7 Hz, 1H), 6.91 (d, J=8.3 Hz, 1H), 4.91 (tt, J=6.3, 1.9 Hz, 1H), 4.05 (qd, J=15.1, 7.6 Hz, 2H), 3.92 (td, J=11.1, 10.3, 6.7 Hz, 4H), 3.10 (q, J=7.3 Hz, 1H), 2.38 (s, 3H), 2.14 (dtd, J=12.8, 9.7, 6.4 Hz, 1H), 2.03-1.88 (m, 2H), 1.84 (ddd, J=16.9, 12.7, 6.3 Hz, 1H), 1.72 (ddq, J=13.1, 6.7, 3.4 Hz, 1H), 1.58 (tq, J=10.9, 5.9, 5.5 Hz, 1H), 1.50-1.29 (m, 10H), 1.29-1.08 (m, 8H), 0.94 (dqd, J=15.7, 7.6, 3.5 Hz, 6H), 0.83 (t, J=6.6 Hz, 3H), 0.77 (t, J=7.4 Hz, 3H). $^{13}$C NMR (150 MHz, Methylene Chloride-d2) δ 165.36, 162.37, 161.72, 157.74, 152.71, 149.29, 148.91, 143.50, 142.64, 139.51, 138.20, 136.90, 136.15, 132.35, 130.34, 129.81, 129.60, 129.34, 126.05, 126.00, 125.04, 122.54, 121.93, 120.62, 117.12, 110.49, 109.98, 107.20, 107.14, 69.40, 45.57, 45.52, 45.17, 45.10, 39.28, 38.67, 35.21, 33.49, 30.26, 29.70, 28.69, 28.29, 24.33, 23.67, 23.16, 23.14, 22.87, 20.54, 13.92, 13.74, 10.20, 8.37. $C_{58}H_{62}N_4O_5S[M^+]$ Exact Mass=926.4441, MS (MALDI)=926.4418

4'-bromo-2,4-bis(hexyloxy)-1,1'-biphenyl (BP)

In a 50 mL 1-neck round-bottom flas, 5.18 grams of 4'-bromo-[1,1'-biphenyl]-2,4-diol (obtained from Pi Pharm) (19.53 mmol) was dissolved in 30 mL DMSO, to which 2.74 grams powdered potassium hydroxide (48.85 mmol) was added while stirring. The diol and base were allowed to react for 5-10 minutes, turning the suspension greenish in color. This suspension was cooled in an ice-bath for 2-3 minutes, before adding 9.67 grams (58.59 mmol) of n-hexylbromide slowly by syringe. After complete addition, and stiffing in the ice-bath for 5-10 minutes, the reaction was removed from the ice-bath and allowed to warm up to room temperature over several hours. The reaction was checked for completeness by TLC and then extracted with methylene chloride and several water washes to remove DMSO. The crude product was concentrated by rotoevaporator at reduced pressure, and then purified by silica gel column chromatography: pure hexanes to 50/50 DCM/hexanes. 8.05 grams (95% yield) of a pure clear oil were obtained.

$^1$H NMR (400 MHz, Methylene Chloride-d2) δ 7.52 (d, J=8.5 Hz, 2H), 7.44 (d, J=8.6 Hz, 2H), 7.22 (d, J=8.8 Hz, 1H), 6.59-6.54 (m, 2H), 3.99 (dt, J=13.4, 6.5 Hz, 4H), 1.88-1.68 (m, 4H), 1.58-1.25 (m, 12H), 1.01-0.87 (m, 6H). $^{13}$C NMR (100 MHz, Methylene Chloride-d2) δ 160.18, 156.87, 137.63, 131.12, 130.80, 130.79, 121.78, 120.00, 105.40, 100.07, 68.36, 68.13, 31.62, 31.45, 29.27, 29.05, 25.77, 25.72, 22.65, 22.59, 13.85, 13.79.

4-(2',4'-bis(hexyloxy)-[1,1'-biphenyl]-4-yl)-7-bromo-1,2,3,3a,4,8b-hexahydrocyclopenta[b]indole (BPIndoline)

In a 25 mL single-neck round-bottom flask, 1.31 grams of 4'-bromo-2,4-bis(hexyloxy)-1,1'-biphenyl (3.02 mmol), 0.450 grams of 1,2,3,3a,4,8b-hexahydrocyclopenta[b]indole (2.83 mmol), and 0.375 grams of sodium t-butoxide (3.90 mmol) were dissolved in 15 mL of toluene. This solution was degassed for 20 minutes with a stream of N$_2$, after which time 30 mg of Bis(tri-tert-butylphosphine)palladium (0) was added in one batch. The reaction was then brought to 80° C. overnight, and then diluted with DCM and plugged through a thin pad of MgSO$_4$ with DCM. Volatile organics were removed and the crude compound loaded onto silica gel column. Purification was performed with a 2% EtOAc in Hexanes eluent. 1.41 grams (91% yield) of a pale yellow, viscous oil (store in the freezer) were obtained.

$^1$H NMR (400 MHz, Methylene Chloride-d2) δ 7.53 (d, J=8.1 Hz, 2H), 7.33 (d, J=8.3 Hz, 2H), 7.27 (d, J=8.0 Hz, 1H), 7.16 (d, J=7.1 Hz, 1H), 7.08 (q, J=3.9, 2.6 Hz, 2H), 6.80-6.71 (m, 1H), 6.57 (d, J=8.4 Hz, 1H), 4.88-4.77 (m, 1H), 4.01 (q, J=6.5 Hz, 4H), 3.84 (td, J=8.8, 2.8 Hz, 1H), 2.09 (td, J=12.6, 7.8 Hz, 2H), 2.04-1.64 (m, 6H), 1.53 (ddd, J=27.1, 11.4, 5.0 Hz, 6H), 1.46-1.26 (m, 8H), 1.06-0.83 (m, 6H). $^{13}$C NMR (100 MHz, Methylene Chloride-d2) δ 159.50, 156.94, 147.21, 141.60, 135.17, 131.17, 130.61, 129.96, 126.97, 124.61, 122.92, 118.56, 118.08, 108.12, 105.34, 100.14, 68.66, 68.34, 68.11, 45.52, 34.85, 34.07, 31.63, 31.59, 31.51, 29.31, 29.15, 25.81, 25.74, 24.44, 22.65, 22.61, 13.89, 13.83, 13.80.

4-(2',4'-bis(hexyloxy)-[1,1'-biphenyl]-4-yl)-7-bromo-1,2,3,3a,4,8b-hexahydrocyclopenta[b]indole (BPIndoline-Br)

In a 50 mL single-neck round-bottom flask, 1.4 grams of BPIndoline (2.7 mmol) were dissolved in 22 mL acetone and cooled to 0° C. 0.492 grams of NBS (2.8 mmol) were then added in one portion, and the reaction was let warm to room temperature over 1 hour. At this time, the reaction was poured into hexanes and washed with 10% aqueous NaOH solution. After removal of the volatile organics, the crude product was purified by silica gel chromatography with 10% DCM in hexanes eluent. 1.60 grams of pure, pale yellow, viscous oil were obtained (98% yield).

$^1$H NMR (400 MHz, Methylene Chloride-d2) δ 7.52 (d, J=8.7 Hz, 2H), 7.33 (d, J=8.3 Hz, 2H), 7.25-7.21 (m, 2H), 7.14 (dd, J=8.5, 2.2 Hz, 1H), 6.91 (d, J=8.5 Hz, 1H), 6.56 (d, J=7.2 Hz, 2H), 4.84 (ddd, J=8.9, 6.3, 2.5 Hz, 1H), 4.00 (q, J=6.7 Hz, 4H), 3.89 (td, J=8.8, 2.8 Hz, 1H), 2.08 (td, J=12.6, 7.8 Hz, 2H), 2.01-1.61 (m, 6H), 1.59-1.43 (m, 6H), 1.43-1.25 (m, 8H), 1.02-0.82 (m, 6H). $^{13}$C NMR (100 MHz, Methylene Chloride-d2) δ 159.58, 156.93, 146.62, 140.96, 137.68, 131.89, 130.62, 130.04, 129.54, 127.49, 122.73, 118.52, 109.27, 109.13, 105.36, 100.13, 69.06, 68.34, 68.12, 45.31, 34.83, 33.88, 31.60, 31.57, 31.47, 29.28, 29.11, 26.90, 25.78, 25.71, 24.37, 22.64, 22.62, 22.58, 13.86, 13.80, 13.78.

4-(2',4'-bis(hexyloxy)-[1,1'-biphenyl]-4-yl)-7-(4,4,5,5-tetramethyl-1,3,2-dioxaborolan-2-yl)-1,2,3,3a,4,8b-hexahydrocyclopenta[b]indole (BPIndoline-BPin)

The product was synthesized in the same manner as for the synthesis of TolIndoline-BPin. Purification by silica gel chromatography with 50:50 Hexanes:DCM to 30:70 Hexanes:DCM gradient eluent. 1.46 grams (83% yield) of a pure, pale yellow, viscous oil (store in the freezer) were obtained.

$^1$H NMR (400 MHz, Methylene Chloride-d2) δ 7.58 (s, 1H), 7.56 (d, J=8.0 Hz, 1H), 7.52 (d, J=8.6 Hz, 2H), 7.30 (d, J=8.6 Hz, 2H), 7.28-7.25 (m, 1H), 7.01 (d, J=8.0 Hz, 1H), 6.55 (dd, J=5.9, 2.5 Hz, 2H), 4.84 (ddd, J=8.8, 6.3, 2.2 Hz, 1H), 3.98 (dt, J=12.5, 6.5 Hz, 2H), 3.84 (td, J=8.8, 2.8 Hz, 1H), 2.10-1.91 (m, 6H), 1.89-1.71 (m, 10H), 1.70-1.57 (m, 2H), 1.56-1.23 (m, 16H), 1.02-0.82 (m, 6H). $^{13}$C NMR (100 MHz, CDCl$_3$) δ 159.45, 156.94, 150.29, 140.75, 135.04, 134.28, 131.01, 130.79, 130.08, 123.08, 119.26, 118.31, 107.28, 105.25, 100.39, 83.22, 68.93, 68.37, 68.10, 45.16, 34.92, 33.81, 31.62, 31.43, 29.32, 29.07, 26.91, 25.77, 25.76, 24.94, 24.76, 24.57, 24.41, 22.63, 22.57, 14.06, 14.01.

BPIndoline-Th-DPP_EthHex-Ph-Furaldehyde

The reaction and purification were performed in the same manner as for the synthesis of HexOTPA-Th-DPP_EthHex-Ph-Furaldehyde, with the coupling partner BPIndoline-BPin. 200 mg (62% yield) of a blue solid.

$^1$H NMR (400 MHz, Methylene Chloride-d2) δ 9.69 (s, 1H), 9.12 (dd, J=4.1, 0.9 Hz, 1H), 8.01-7.96 (m, 2H), 7.93 (d, J=8.6 Hz, 2H), 7.59-7.54 (m, 2H), 7.51 (t, J=1.4 Hz, 1H), 7.47 (dd, J=8.3, 2.0 Hz, 1H), 7.41 (d, J=4.2 Hz, 1H), 7.39 (d, J=3.7 Hz, 1H), 7.37-7.32 (m, 2H), 7.29-7.25 (m, 1H), 7.05 (d, J=8.1 Hz, 1H), 7.02 (d, J=3.7 Hz, 1H), 6.60-6.55 (m, 2H), 4.95 (t, J=7.4 Hz, 1H), 4.10 (q, J=7.2 Hz, 2H), 4.01 (td, J=6.5, 4.7 Hz, 6H), 3.97-3.83 (m, 3H), 2.22-2.06 (m, 2H), 2.00-1.87 (m, 2H), 1.85-1.70 (m, 6H), 1.55-1.50 (m, 6H), 1.50-1.31 (m, 14H), 1.31-1.05 (m, 8H), 0.93 (tdd, J=7.2, 6.0, 2.9 Hz, 12H), 0.78 (dt, J=20.7, 6.7 Hz, 6H). $^{13}$C NMR (100 MHz, Methylene Chloride-d2) δ 177.19, 162.37, 161.67, 159.67, 158.13, 156.95, 152.67, 152.47, 148.74, 143.27, 142.74, 140.28, 140.26, 138.24, 136.39, 132.55, 130.66, 130.30, 130.12, 129.90, 129.22, 128.11, 126.09, 125.95, 125.22, 125.19, 123.27, 122.60, 122.53, 122.02, 119.29, 119.28, 110.52, 108.95, 107.76, 107.07, 105.38, 100.11, 69.23, 68.35, 68.12, 60.21, 45.56, 45.18, 45.04, 38.71, 35.08, 33.65, 31.60, 31.48, 30.24, 29.28, 29.11, 28.63, 28.25, 25.79, 25.71, 25.45, 24.37, 23.66, 23.61, 23.58, 23.13, 23.11, 22.82, 22.62, 22.60, 20.76, 13.97, 13.89, 13.87, 13.81, 13.80, 13.69, 10.28, 10.24, 10.19.

DPP15, BPIndoline-Th-DPP_EthHex-Ph-FuranylCAA

The reaction and purification were performed in the same manner as for the synthesis of DPP13. 161 mg (76% yield) of a blue/green solid.

$^1$H NMR (600 MHz, Methylene Chloride-d2) δ 9.14 (d, J=4.1 Hz, 1H), 8.08 (s, 1H), 8.05 (d, J=8.3 Hz, 2H), 7.96 (d, J=8.2 Hz, 2H), 7.58 (d, J=8.5 Hz, 2H), 7.53 (s, 1H), 7.49 (dd, J=8.4, 2.0 Hz, 1H), 7.43 (d, J=4.2 Hz, 1H), 7.40-7.34 (m, 3H), 7.29 (d, J=8.3 Hz, 1H), 7.10 (d, J=3.7 Hz, 1H), 7.07 (d, J=8.3 Hz, 1H), 6.59 (d, J=9.7 Hz, 2H), 5.00-4.94 (m, 1H), 4.10-4.00 (m, 8H), 3.94 (dq, J=13.0, 7.1, 6.0 Hz, 3H), 2.17 (tdd, J=12.0, 9.7, 6.5 Hz, 1H), 2.05-1.95 (m, 3H), 1.93 (ddd, J=13.3, 8.6, 5.5 Hz, 1H), 1.82 (ddt, J=19.6, 14.9, 6.6 Hz, 4H), 1.75 (ddd, J=8.9, 6.0, 2.8 Hz, 1H), 1.59 (dq, J=11.5, 5.5 Hz, 2H), 1.55-1.46 (m, 4H), 1.46-1.30 (m, 12H), 1.24 (dt, J=13.5, 7.6 Hz, 2H), 1.18 (h, J=6.5, 5.9 Hz, 8H), 0.99-0.91 (m, 12H), 0.83 (t, J=6.3 Hz, 3H), 0.78 (t, J=7.4 Hz, 3H). $^{13}$C NMR (150 MHz, Methylene Chloride-d2) δ 163.50, 161.48, 159.69, 156.97, 152.92, 148.84, 148.34, 146.21, 141.94, 140.26, 138.24, 136.44, 132.61, 130.68, 130.25, 130.15, 129.85, 129.63, 126.03, 125.95, 125.44, 123.23, 122.62, 122.58, 122.13, 119.35, 119.34, 115.74, 110.44, 109.95, 107.79, 107.17, 105.39, 100.13, 97.83, 69.26, 68.37, 68.15, 45.88, 45.20, 44.92, 39.21, 38.72, 35.12, 33.66, 31.63, 31.50, 30.27, 29.30, 29.14, 28.59, 28.28, 25.81, 25.73, 24.40, 23.65, 23.16, 23.14, 22.84, 22.65, 22.64, 22.62, 13.92, 13.91, 13.83, 13.72, 10.26, 10.23, 10.16. $C_{75}H_{88}N_4O_7S[M^+]$ Exact Mass=1188.6374, MS (MALDI)=1188.6367

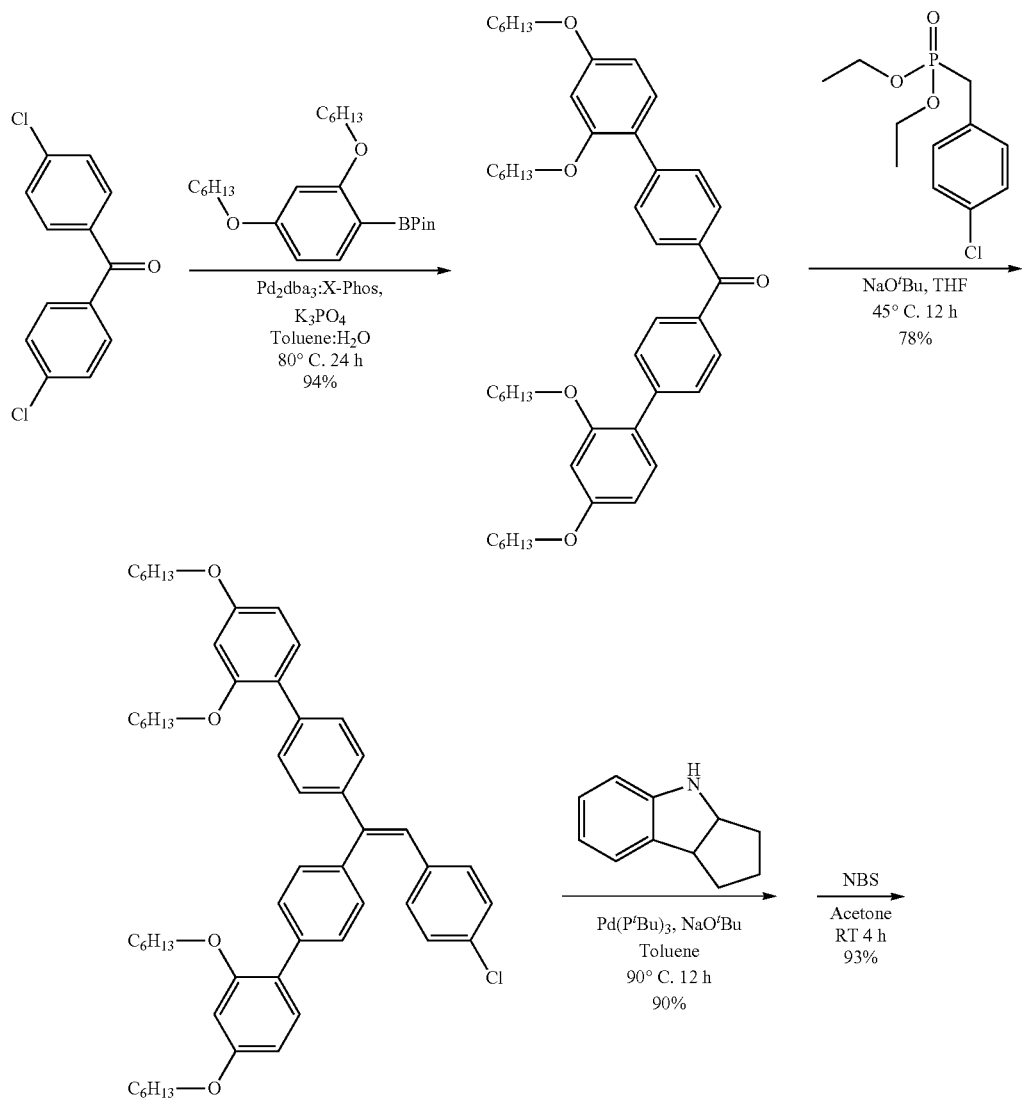

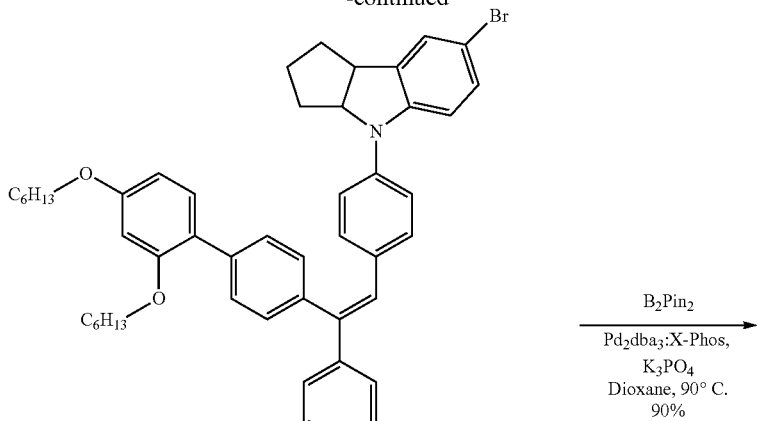

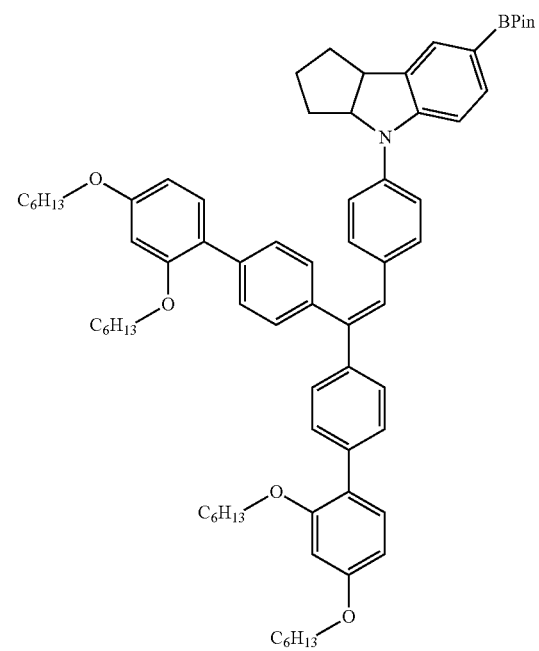

Bis(2',4'-bis(hexyloxy)-[1,1'-biphenyl]-4-yl)methanone

A Suzuki coupling between 2-(2,4-bis(hexyloxy)phenyl)-4,4,5,5-tetramethyl-1,3,2-dioxaborolane and bis(4-chlorophenyl)methanone was performed in analogous fashion as described for HexOTPA-Th-DPP_EthHex-Ph-Furaldehyde. 1.22 grams (94% yield) of a pure clear oil.

$^1$H NMR (400 MHz, Methylene Chloride-d2) δ 7.88 (d, J=8.3 Hz, 4H), 7.71 (d, J=8.3 Hz, 4H), 7.34 (d, J=9.0 Hz, 2H), 6.61 (dq, J=4.7, 2.4 Hz, 4H), 4.03 (q, J=6.4 Hz, 8H), 1.87-1.71 (m, 8H), 1.58-1.44 (m, 4H), 1.44-1.18 (m, 16H), 1.04-0.85 (m, 12H). $^{13}$C NMR (100 MHz, Methylene Chloride-d2) δ 195.71, 160.52, 157.17, 142.86, 135.47, 131.14, 129.61, 129.11, 121.94, 105.54, 100.08, 68.43, 68.17, 31.59, 31.42, 29.24, 29.03, 25.76, 25.70, 25.68, 24.63, 22.62, 22.56, 13.81, 13.78.

4',4'''-(2-(4-chlorophenyl)ethene-1,1-diyl)bis(2,4-bis(hexyloxy)-1,1'-biphenyl)

In a 50 mL single-neck round-bottom flask, 1.9 grams of bis(2',4'-bis(hexyloxy)-[1,1'-biphenyl]-4-yl)methanone (2.58 mmol) and 0.465 gram of tertiary butoxide (3.87 mmol) were dissolved in 45 mL dry THF under N$_2$ atm. To the reaction mixture 1.02 grams of diethyl 4-chlorobenzylphosphonate (3.87 mmol) was added dropwise and heated to 45° C. and stirred until the complete formation of product which is monitored by TLC (approx. 12 hours). After the completion of the reaction, the reaction mixture was diluted with dichloromethane and washed with water. The organic layer was dried over MgSO$_4$ and concentrated. The crude product was purified by silica gel chromatography with 1:4 DCM:hexanes eluent. 1.70 grams (78% yield) of pure, clear oil were obtained.

$^1$H NMR (400 MHz, Chloroform-d) δ 7.55-7.48 (m, 4H), 7.43-7.37 (m, 2H), 7.32 (dd, J=8.9, 2.2 Hz, 1H), 7.29-7.25 (m, 1H), 7.25-7.20 (m, 2H), 7.14-7.08 (m, 2H), 7.06-6.99 (m, 2H), 6.96 (s, 1H), 6.60-6.53 (m, 4H), 4.04-3.93 (m, 8H), 1.87-1.70 (m, 8H), 1.49 (tdd, J=10.9, 6.3, 3.0 Hz, 4H), 1.45-1.33 (m, 10H), 1.33-1.22 (m, 6H), 0.97-0.82 (m, 12H). $^{13}$C NMR (100 MHz, Methylene Chloride-d2) 160.08, 160.07, 157.18, 157.15, 143.36, 141.01, 138.22, 138.06, 137.88, 136.42, 132.08, 131.03, 130.93, 129.83, 129.81, 129.30, 128.09, 127.16, 126.16, 122.83, 122.71, 105.48, 105.44, 100.30, 100.23, 68.43, 68.37, 68.15, 31.77, 31.60, 31.55, 29.44, 29.43, 29.27, 29.22, 25.88, 22.78, 22.71, 14.01, 13.97, 13.95.

4-(4-(2,2-bis(2',4'-bis(hexyloxy)-[1,1'-biphenyl]-4-yl)vinyl)phenyl)-1,2,3,3a,4,8b-hexahydrocyclopenta[b]indole (BigIndoline)

The amination reaction between 1,2,3,3a,4,8b-hexahydrocyclopenta[b]indole and 4',4'''-(2-(4-chlorophenyl)ethene-1,1-diyl)bis(2,4-bis(hexyloxy)-1,1'-biphenyl) was performed in an analogous fashion to what was reported above for the synthesis of 4-(2',4'-bis(hexyloxy)-[1,1'-biphenyl]-4-yl)-7-bromo-1,2,3,3a,4,8b-hexahydrocyclopenta[b]indole (BPIndoline). 0.54 grams (90% yield) of a pale, viscous, yellow oil (store in the freezer) were obtained.

$^1$H NMR (400 MHz, Methylene Chloride-d2) δ 7.63-7.59 (m, 2H), 7.53-7.48 (m, 2H), 7.41-7.38 (m, 2H), 7.38-7.34 (m, 1H), 7.33-7.29 (m, 2H), 7.29-7.25 (m, 1H), 7.10 (s, 5H), 7.03 (t, J=2.1 Hz, 3H), 6.74 (dt, J=7.3, 4.1 Hz, 1H), 6.65-6.51 (m, 4H), 4.75 (ddd, J=8.8, 5.6, 3.3 Hz, 1H), 4.07-3.96 (m, 8H), 3.84 (td, J=8.8, 2.8 Hz, 1H), 2.05 (dddd, J=12.5, 10.2, 8.4, 6.4 Hz, 1H), 1.88 (dt, J=9.3, 5.5 Hz, 2H), 1.79 (ttd, J=14.5, 6.9, 3.0 Hz, 8H), 1.66 (ddd, J=16.0, 7.8, 4.6 Hz, 1H), 1.54-1.23 (m, 16H), 0.99-0.87 (m, 9H), 0.88-0.81 (m, 3H). $^{13}$C NMR (100 MHz, Methylene Chloride-d2) δ 159.90, 159.87, 157.07, 157.04, 146.43, 141.96, 141.60, 139.84, 138.69, 137.52, 137.40, 135.31, 130.96, 130.87, 130.31, 129.90, 129.74, 129.72, 129.09, 127.24, 126.92, 126.72, 124.59, 122.85, 122.73, 119.00, 117.18, 108.73, 105.44, 105.37, 100.20, 100.09, 68.43, 68.38, 68.34, 68.12, 45.42, 34.61, 34.12, 31.61, 31.60, 31.45, 31.36, 29.28, 29.26, 29.07, 25.72, 25.70, 24.35, 22.62, 22.56, 22.54, 13.80, 13.78, 13.74.

4-(4-(2,2-bis(2',4'-bis(hexyloxy)-[1,1'-biphenyl]-4-yl)vinyl)phenyl)-7-bromo-1,2,3,3a,4,8b-hexahydrocyclopenta[b]indole (Br-BigIndoline)

The bromination was performed in an analogous fashion as to what was reported above for the synthesis of 4-(2',4'-bis(hexyloxy)-[1,1'-biphenyl]-4-yl)-7-bromo-1,2,3,3a,4,8b-hexahydrocyclopenta[b]indole (BPIndoline-Br). 200 mg (93% yield) of a pale, viscous, yellow oil (store in the freezer) were obtained.

$^1$H NMR (400 MHz, Methylene Chloride-d2) δ 7.63-7.57 (m, 2H), 7.52-7.48 (m, 2H), 7.41-7.37 (m, 2H), 7.36-7.34 (m, 1H), 7.32-7.28 (m, 2H), 7.28-7.25 (m, 1H), 7.19 (dd, J=2.2, 1.1 Hz, 1H), 7.13-7.01 (m, 6H), 6.88 (d, J=8.5 Hz, 1H), 6.62-6.53 (m, 4H), 4.76-4.68 (m, 1H), 4.06-3.95 (m, 8H), 3.81 (td, J=8.8, 2.7 Hz, 1H), 2.04 (dddd, J=12.6, 10.1, 8.5, 6.4 Hz, 1H), 1.82 (dtdd, J=24.0, 14.7, 7.1, 5.4 Hz, 10H), 1.65 (ddd, J=11.9, 9.8, 6.2 Hz, 1H), 1.54-1.24 (m, 16H), 0.97-0.87 (m, 9H), 0.87-0.80 (m, 3H). $^{13}$C NMR (100 MHz, Methylene Chloride-d2) δ 159.92, 159.89, 157.07, 157.04, 145.86, 141.49, 141.31, 140.29, 138.57, 137.82, 137.58, 137.50, 130.94, 130.87, 130.62, 130.36, 129.71, 129.52, 129.10, 127.50, 127.06, 126.74, 122.81, 122.70, 117.62, 109.79, 109.73, 105.46, 105.38, 100.21, 100.09, 68.81, 68.38, 68.33, 68.13, 45.24, 34.60, 33.94, 31.60, 31.59, 31.44, 31.36, 29.27, 29.26, 29.07, 25.72, 25.71, 25.69, 24.31, 22.61, 22.55, 22.53, 13.79, 13.77, 13.77, 13.73.

4-(4-(2,2-bis(2',4'-bis(hexyloxy)-[1,1'-biphenyl]-4-yl)vinyl)phenyl)-7-(4,4,5,5-tetramethyl-1,3,2-dioxaborolan-2-yl)-1,2,3,3a,4,8b-hexahydrocyclopenta[b] indole (BPin-BigIndoline) Ipso substitution of the bromide to BPin was performed in an analogous fashion to what was reported above for the synthesis of 7-(4,4,5,5-tetramethyl-1,3,2-dioxaborolan-2-yl)-4-(p-tolyl)-1,2,3,3a,4,8b-hexahydrocyclopenta[b]indole (TolIndoline-BPin). 180 mg (90% yield) of a pale, viscous, yellow oil (store in the freezer) were obtained.

$^1$H NMR (400 MHz, Methylene Chloride-d2) δ 7.61 (d, J=8.2 Hz, 2H), 7.53-7.48 (m, 3H), 7.45 (d, J=7.8 Hz, 1H), 7.39 (d, J=8.4 Hz, 2H), 7.35 (d, J=9.1 Hz, 1H), 7.31 (d, J=8.2 Hz, 2H), 7.27 (d, J=9.0 Hz, 2H), 7.11 (s, 4H), 7.03 (s, 1H), 6.97 (d, J=8.0 Hz, 1H), 6.63-6.54 (m, 4H), 4.75 (ddd, J=8.8, 5.6, 3.3 Hz, 1H), 4.05-3.96 (m, 8H), 3.82 (td, J=8.7, 2.6 Hz, 1H), 2.05 (dddd, J=12.6, 10.4, 8.5, 6.3 Hz, 1H), 1.93-1.71 (m, 10H), 1.71-1.59 (m, 1H), 1.48-1.23 (m, 28H), 0.98-0.88 (m, 9H), 0.88-0.80 (m, 3H). $^{13}$C NMR (100 MHz, Methylene Chloride-d2) δ 159.89, 157.07, 141.53, 141.14, 140.31, 138.58, 137.59, 137.49, 134.67, 130.96, 130.87, 130.79, 130.31, 129.72, 129.10, 127.12, 126.76, 122.84, 122.72, 118.25, 107.56, 105.46, 105.38, 100.22, 100.10, 83.18, 68.58, 68.38, 68.12, 45.09, 34.79, 33.84, 31.60, 31.45, 31.36, 29.67, 29.27, 29.07, 25.70, 24.69, 24.56, 24.30, 22.62, 22.56, 22.53, 13.79, 13.74.

BigIndoline-Th-DPP_EthHex-Ph-Furaldehyde

The reaction and purification were performed in the same manner as for the synthesis of HexOTPA-Th-DPP_EthHex-Ph-Furaldehyde, with the coupling partner BPin-BigIndoline. 220 mg (68% yield) of a blue/green solid.

$^1$H NMR (400 MHz, Methylene Chloride-d2) δ 9.69 (s, 1H), 9.10 (d, J=4.1 Hz, 1H), 7.99 (d, J=8.5 Hz, 2H), 7.92 (d, J=8.5 Hz, 2H), 7.62 (d, J=8.2 Hz, 2H), 7.52 (d, J=8.4 Hz, 2H), 7.48 (s, 1H), 7.46-7.38 (m, 5H), 7.36 (d, J=9.1 Hz, 1H), 7.32 (d, J=8.2 Hz, 2H), 7.27 (d, J=9.0 Hz, 2H), 7.14 (s, 4H), 7.07-7.01 (m, 3H), 6.63-6.55 (m, 4H), 4.83 (ddd, J=8.8, 5.6, 3.3 Hz, 1H), 4.06-3.96 (m, 12H), 3.95-3.84 (m, 3H), 2.18-2.05 (m, 1H), 2.00-1.79 (m, 4H), 1.79-1.73 (m, 8H), 1.73-1.65 (m, 1H), 1.57-1.06 (m, 16H), 1.01-0.71 (m, 24H).

$^{13}$C NMR (101 MHz, CD2C12) δ 177.19, 162.36, 161.68, 159.93, 159.90, 158.12, 157.07, 157.04, 152.46, 147.95, 143.36, 142.69, 141.43, 140.66, 138.51, 138.17, 137.64, 137.59, 136.53, 131.28, 130.95, 130.88, 130.41, 130.33, 129.88, 129.74, 129.71, 129.22, 129.12, 126.97, 126.78, 126.22, 125.86, 125.22, 123.68, 122.79, 122.68, 122.49, 122.15, 118.43, 110.51, 108.96, 108.37, 107.13, 105.46, 105.38, 100.20, 100.09, 68.99, 68.38, 68.33, 68.13, 45.55, 45.13, 39.23, 38.71, 34.86, 33.75, 31.60, 31.45, 31.37, 30.26, 29.67, 29.27, 29.08, 28.61, 28.25, 25.72, 25.70, 24.33, 23.66, 23.59, 23.10, 22.81, 22.62, 22.56, 22.54, 13.87, 13.80, 13.74, 13.69, 10.28, 10.24, 10.18.

DPP17, BigIndoline-Th-DPP EthHex-Ph-FuranylCAA

The reaction and purification were performed in the same manner as for the synthesis of DPP13. 150 mg (83% yield) of a blue/green solid.

$^1$H NMR (600 MHz, Methylene Chloride-d2) δ 9.12 (d, J=4.2 Hz, 1H), 8.08 (s, 1H), 8.06 (d, J=8.2 Hz, 2H), 7.96 (d, J=8.2 Hz, 2H), 7.63 (d, J=7.9 Hz, 2H), 7.53 (d, J=8.1 Hz, 2H), 7.50 (s, 1H), 7.46 (d, J=8.4 Hz, 1H), 7.45-7.40 (m, 3H), 7.38 (d, J=9.1 Hz, 1H), 7.36 (d, J=3.1 Hz, 1H), 7.33 (d, J=8.0 Hz, 2H), 7.29 (d, J=8.4 Hz, 1H), 7.20-7.11 (m, 4H), 7.11 (d, J=3.7 Hz, 1H), 7.07 (s, 1H), 7.05 (d, J=8.4 Hz, 1H), 6.66-6.50 (m, 4H), 4.85 (t, J=7.6 Hz, 1H), 4.10-4.00 (m, 12H), 3.98-3.89 (m, 3H), 2.13 (p, J=9.0, 7.9 Hz, 1H), 2.02-1.87 (m, 4H), 1.89-1.78 (m, 8H), 1.76-1.66 (m, 1H), 1.63-1.09 (m, 16H), 1.00-0.88 (m, 15H), 0.84 (dt, J=17.5, 6.7 Hz, 6H), 0.77 (t, J=7.4 Hz, 3H). $^{13}$C NMR (150 MHz, Methylene Chloride-d2) δ 163.26, 161.52, 159.96, 159.92, 158.39, 157.09, 157.06, 152.64, 148.34, 148.03, 142.04, 141.46, 140.68, 138.53, 138.17, 137.66, 137.60, 136.58, 131.32, 130.97, 130.90, 130.43, 130.19, 129.90, 129.76, 129.73, 129.57, 129.14, 126.99, 126.81, 126.13, 125.92, 125.43, 123.66, 122.79, 122.68, 122.53, 122.24, 118.48, 115.75, 110.45, 110.08, 108.39, 107.22, 105.46, 105.38, 100.20, 100.09, 97.55, 69.02, 68.39, 68.34, 68.14, 45.81, 45.14, 44.95, 39.21, 38.71, 34.88, 33.75, 31.62, 31.47, 31.39, 30.25, 29.28, 29.09, 28.58, 28.27, 25.74, 25.72, 24.35, 23.65, 23.53, 23.12, 22.83, 22.64, 22.58, 22.56, 13.89, 13.82, 13.80, 13.77, 13.71, 10.23, 10.15. $C_{107}H_{126}N_4O_9S[M^+]$ Exact Mass=1642.9246, MS (MALDI)=1643.9327

All reagents from commercial sources were used without further purification, unless otherwise noted. All reactions were performed under dry $N_2$, unless otherwise noted. All dry reactions were performed with glassware that was flamed under high-vacuum and backfilled with $N_2$. All extracts were dried over powdered $MgSO_4$ and solvents removed by rotary evaporation under reduced pressure. Flash chromatography was performed using Silicycle Ultra-Pure SilicaFlash P60, 40-63 μm (230-400 mesh). $^1$H and $^{13}$C NMR spectra were recorded on a Bruker Avance-400 (400 MHz), Bruker AvanceIII-400 (400 MHz), Bruker DPX-400 (400 MHz), or Bruker DRX-600 spectrometer and are reported in ppm using solvent as an internal standard: Methylene Chloride-$d_2$ at 5.32 ppm and 54.00 ppm for $^1$H and $^{13}$C, respectively; THF-$d_8$ at 3.58 ppm and 67.57 ppm for $^1$H and $^{13}$C, respectively.

Preparation of Dye Solar Cells (DSC) Comprising a Compound of the Invention Selected From Compound of Formula (72) Referred as DPP07, Compound of Formula (77) Referred as DPP13, Compound of Formula (75) Referred as DPP14, Compound of Formula (88) Referred as DPP15, and Compound of Formula (74) Referred as DPP17

DSCs were prepared as previously described. In brief, the $TiO_2$ transparent electrodes composed of ~20 nm anatase resulting in ~30 nm pore on fluorine doped thin oxide (FTO, 4 mm thickness, 10 ohms/sq, Nippon Sheet Glass, Japan) conducting glass were controlled to get a desired thickness, e.g. ~3.5 μm. A 4~5 μm scattering layer (400 nm, CCIC, HPW-400) was printed on the top of the transparent layer to increase light path length by scattering. The $TiO_2$ electrodes were immersed into a 0.025 mM solution of a dye of the invention with 1.25 mM (DPP07, DPP13) or 2.5 mM (DPP14, DPP15, DPP17) of 3α,7α-dihydroxy-5β-cholic acid (chenodeoxycholic acid) in 4-tert-butanol/acetonitrile mixture (1:1 v/v) and kept for 15 h at room temperature. Two electrolyte were applied: EL_I (iodine based electrolyte contains 0.6 M 1,3-dimethylimidazolium iodide, 0.03 M $I_2$, 0.05 M LiI, 0.05 M guanidinium thiocyanate, and 0.25 M 4-tert-butylpyridine in 15/85 (v/v) mixture of valeronitrile and acetonitrile) and EL_Co (cobalt tris-bpy based electrolyte contains 0.22 M Co(II), 0.05 M Co(III), 0.1 M $LiClO_4$, and 0.2 M 4-tert-butylpyridine in acetonitrile). As for the counter electrode, a platinized counter electrode and carbonaceous catalyst FTO (TEC 15 ohms/sq, Pilkington) were used for EL_I and EL_Co electrolyte system, respectively. The carbonaceous typed catalyst has been in general known to perform better than Pt owing to the low charge transfer resistance particularly for the cobalt redox system, as disclosed in Kavan, L., Yum, J.-H. & Gratzel, M. Nano Letters 2011, 11, 5501. The dye-adsorbed $TiO_2$ electrode and the counter electrode were assembled into a sealed sandwich type cell with a gap of a hot-melt ionomer film, Surlyn (25 μm, Du-Pont).

DSC Characterization:

A 450 W xenon light source (Oriel, USA) was used to characterize the solar cells. The spectral output of the lamp was matched in the region of 350-750 nm with the aid of a Schott K113 Tempax sunlight filter (Prazisions Glas & Optik GmbH, Germany) so as to reduce the mismatch between the simulated and true solar spectra to less than 4%. The current-voltage characteristics of the cell under these conditions were obtained by applying external potential bias to the cell and measuring the generated photocurrent with a Keithley model 2400 digital source meter (Keithley, U.S.A.). For IPCE measurement, a modulated light intensity data acquisition system was used to control the Incident Photon-to-Current conversion Efficiency (IPCE) measurement. The modulation frequency was about 1 Hz. Light from a 300 W Xenon lamp (ILC Technology, U.S.A.) was focused through a computer controlled Gemini-180 double monochromator (Jobin Yvon Ltd., UK) onto the photovoltaic cell under test. A white light bias was used to bring the total light intensity on the device under test closer to operating conditions. The devices were masked with a black metal aperture to attain an illuminated active area of 0.2 $cm^2$.

The optical and electrochemical properties of the compounds of the invention: of formula (77) referred as DPP13, of formula (75) referred as DPP14, of formula (88) referred as DPP15 and of formula (74) referred as DPP17 are summarized in Table 2 below.

TABLE 2

Optical and electrochemical properties of compounds of the invention

| Dye | ε ($M^{-1}$ $cm^{-1}$) [$Abs_{max}$ (nm)][a] | $E_{(s+/s)}$ (V)[b] | $E_{(s-/s)}$ (V)[b] | $E_g^{opt}$ (eV)[c] | $E_{(S+/S^*)}$ (V)[d] |
|---|---|---|---|---|---|
| DPP13 | 30,300 (377)/55,700 (587) | 0.99 | −0.98 | 1.85 | −0.86 |
| DPP14 | 31,200 (380)/57,100 (596) | 0.94 | −0.98 | 1.81 | −0.87 |
| DPP15 | 38,800 (374)/62,400 (600) | 0.94 | −0.96 | 1.80 | −0.86 |
| DPP17 | 67,000 (393)/69,000 (602) | 0.98 | −0.99 | 1.80 | −0.82 |

[a]Absorbances of the dyes with ~2 × $10^{-5}$M concentration in THF solution.
[b]The ground-state oxidation potential of the dyes was measured under the following conditions: electrolyte, 0.1M tetra-n-butylammonium hexafluorophosphate in dimethylformamide; electrode, Platinum counter and reference electrodes were used with a glassy carbon working electrode. Potentials measured vs. $Fc^+/Fc$ were converted to NHE by addition of +0.69 V.
[c]Optical transition energy, estimated from the onset of the absorption.
[d]Excited-state oxidation potential energies vs. NHE estimated from the ground-state oxidation potential ($E_{OX}$), by substracting the bandgap ($E_g^{opt}$).

Figure 14:
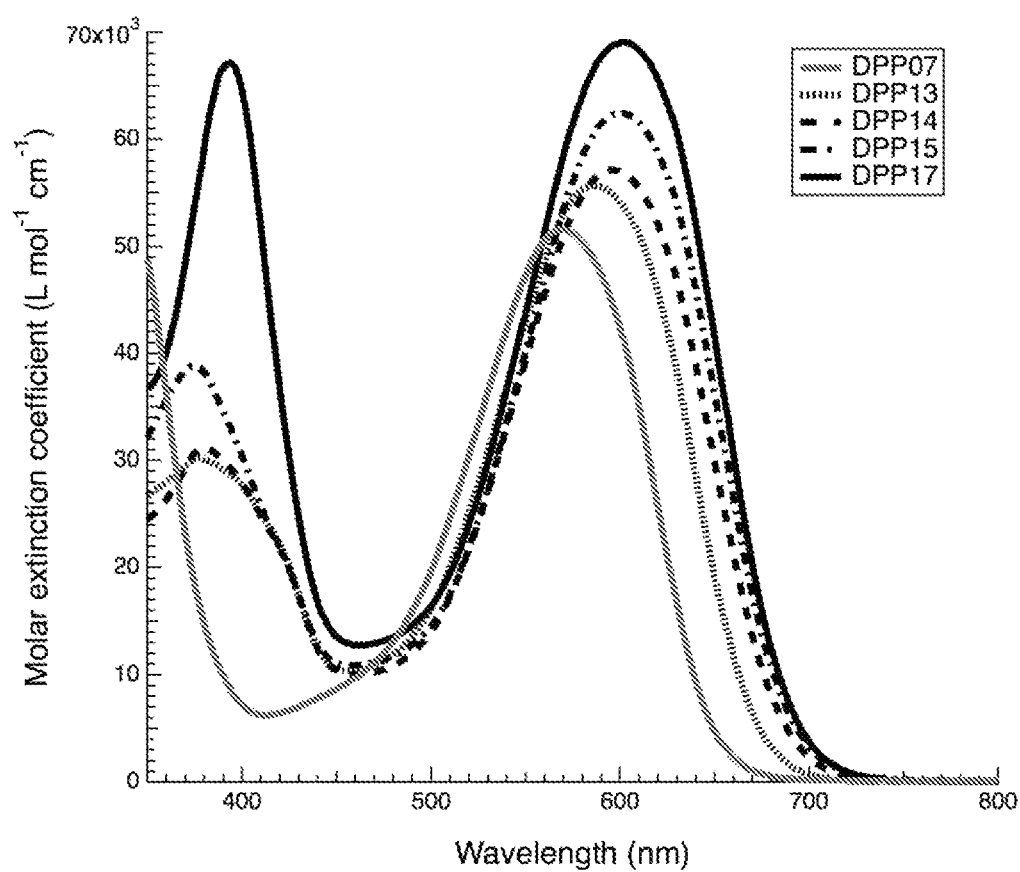
FIG. 14 shows UV-Vis spectra of DPP07 (grey solid line), DPP13 (dotted line), DPP14 (dash dotted line), DPP15 (dashed line), and DPP17 (solid line).

Replacing the anchoring phenyl ring of DPP07 with the furan ring of DPP13 provides a ~20 nm red-shift in the charge-transfer (CT) light absorption band in combination with increased intensity of the CT band compared to the higher energy band. Additionally, a bathochromic shift of the higher energy band is observed as shown in FIG. 14. By employing strongly electron donating indoline groups in DPP14, DPP15, and DPP17 a further ~10 nm red-shift in the low-energy excitation compared to DPP13 was observed. It is worth noting that the slightly extended conjugation of the indoline donor on DPP17 drives the high-energy absorption into the visible region, ~15 nm red-shifted compared to DPP14 and DPP15, and dramatically increases the molar extinction coefficient in this region up to ~65,000 $M^{-1}$ $cm^{-1}$. This red-shifted high-energy absorption peak increases the light harvesting efficiency overall, leading to enhanced photocurrent. Importantly, all these DPP sensitizers absorb 400 nm light, while exhibiting relatively less absorption in the 450-500 nm range, manifesting the observed blue colour.

The compounds of the invention, DPP07, DPP13, DPP14, DPP15, and DPP17, were tested in DSCs with both the $I_3^-/I^-$ based electrolyte (coded EL_I) and the cobalt tris-bipyridyl complex $[Co(bpy)_3]^{3+/2+}$ based electrolyte (coded EL_Co).

TABLE 3

Comparison of photovoltaic characteristics of DSCs sensitized by DPP07, DPP13, DPP14, DPP15, and DPP17 comprising either iodine based electrolyte (EL I) or cobalt tris-bipyridine based electrolyte (EL Co).

| Dye | Redox | $J_{sc}$ (mA cm$^{-2}$) | $V_{oc}$ (mV) | FF | PCE (%) |
|---|---|---|---|---|---|
| DPP07 | EL_I | 15.6 | 680 | 0.73 | 7.67 |
|  | EL_Co | 15.1 | 766 | 0.76 | 8.79 |
| DPP13 | EL_I | 16.2 | 705 | 0.67 | 7.60 |
|  | EL_Co | 15.6 | 743 | 0.78 | 8.97 |
| DPP14 | EL_I | 16.6 | 680 | 0.68 | 7.73 |
|  | EL_Co | 15.2 | 716 | 0.76 | 8.23 |
| DPP15 | EL_I | 16.9 | 684 | 0.65 | 7.44 |
|  | EL_Co | 17.6 | 745 | 0.75 | 9.81 |
| DPP17 | EL_I | 16.3 | 700 | 0.63 | 7.13 |
|  | EL_Co | 17.9 | 761 | 0.74 | 10.1 |

TABLE 4

Photovoltaic characteristics of DSCs comprising cobalt tris-bipyridine based electrolyte (EL Co) and sensitized by DPP13, DPP14, DPP15, and DPP17 as function of the light intensity.

| Dye | $I_O$ (Sun) | $J_{sc}$ (mA cm$^{-2}$) | $V_{oc}$ (mV) | FF | PCE (%) |
|---|---|---|---|---|---|
| DPP07 | 1 | 15.1 | 766 | 0.76 | 8.79 |
|  | 0.51 | 7.87 | 749 | 0.79 | 9.10 |
|  | 0.095 | 1.47 | 698 | 0.81 | 8.76 |
| DPP13 | 1 | 15.6 | 743 | 0.78 | 8.97 |
|  | 0.51 | 8.02 | 725 | 0.80 | 9.08 |
|  | 0.095 | 1.49 | 677 | 0.81 | 8.60 |
| DPP14 | 1 | 15.2 | 716 | 0.76 | 8.23 |
|  | 0.51 | 7.80 | 695 | 0.78 | 8.34 |
|  | 0.095 | 1.42 | 639 | 0.79 | 7.51 |
| DPP15 | 1 | 17.6 | 745 | 0.75 | 9.81 |
|  | 0.51 | 9.01 | 729 | 0.78 | 10.1 |
|  | 0.095 | 1.68 | 679 | 0.79 | 9.52 |
| DPP17 | 1 | 17.9 | 761 | 0.74 | 10.1 |
|  | 0.51 | 9.22 | 746 | 0.77 | 10.4 |
|  | 0.095 | 1.74 | 702 | 0.79 | 10.2 |

Figure 15D:
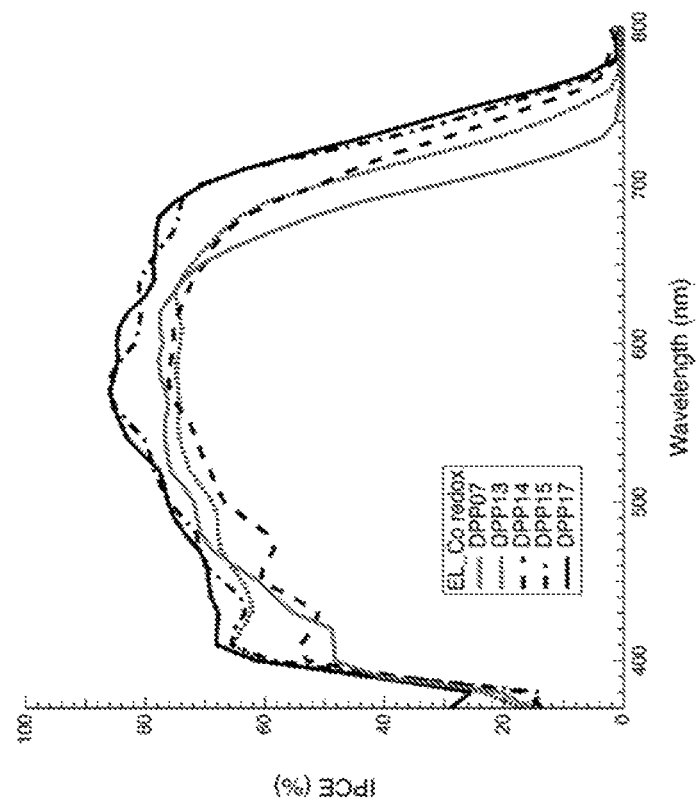
FIG. 15 shows photovoltaic performance of DPP dye-sensitized solar cells with EL_I electrolyte (iodine based electrolyte) (FIGS. 15a and b) and EL_Co electrolyte (cobalt based electrolyte) (FIGS. 15c and d): DPP07 (grey solid lines), DPP13 (dotted lines), DPP14 (dash dotted lines), DPP15 (dashed lines), and DPP17 (solid lines)
Figure 15C:
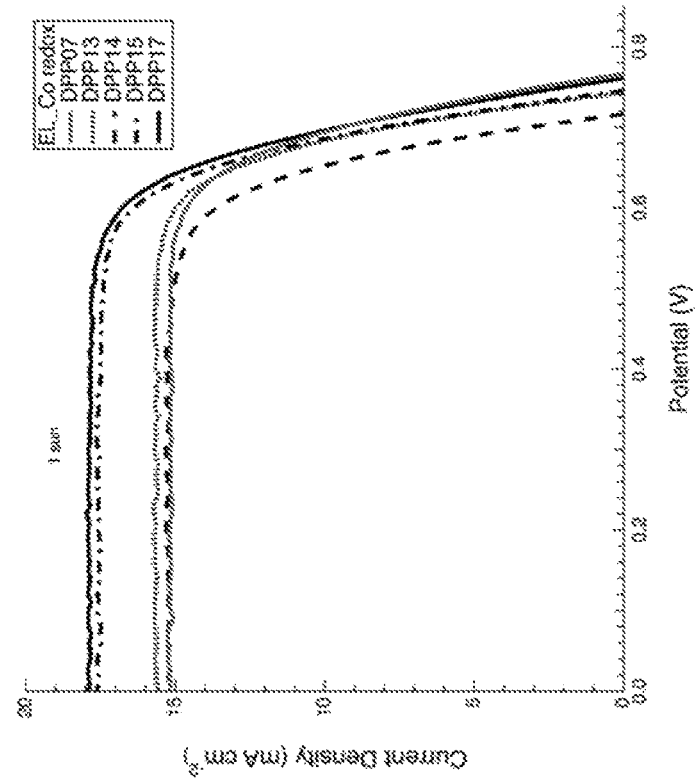

The devices employing $[Co(bpy)_3]^{3+/2+}$ electrolyte outperformed $I_3^-/I^-$ based electrolyte devices, as higher open circuit voltage ($V_{oc}$) and fill factor (FF) provided significant performance enhancement (Tables 3 and 4). The devices employing EL_I generated short circuit current densities of 16-17 mA cm$^{-1}$ and overall PCEs greater than 7% (see output characteristics in Tables 3 and 4). The enhanced absorption properties of DPP13 compared to the benchmark sensitizer DPP07 were reflected in the incident photon-to-electron conversion efficiency (IPCE), leading to the higher current and confirming the utility of the furanylcyanoacrylic acid anchor (see FIG. 15). The IPCEs of DPP14 and 15 exceeded 60% over most of visible light region from 400 to 700 nm, with a maximum of ~80% at around 570 nm—the lowest values being between 400-500 nm. DPP17 exhibited better performance in this region, while maintaining a vivid blue colour. Overall, the best PCE for the EL_I was obtained with DPP14 at 7.73%. The DPP17 achieved over 10% PCE, followed by DPP15 (9.81%), DPP13 (8.97%), DPP07 (8.69%), and DPP14 (8.23%). Enhanced photocurrent led to a higher PCE for DPP13 compared to DPP07, despite of a small loss in $V_{oc}$. Implementing the smallest indoline-based donor in DPP14 yielded a PCE of 8.23%, which was mainly due to a loss in the $V_{oc}$ compared to DPP07 and DPP13.

All IPCEs of DPP dyes exceeded 60% over most of the visible light region from 400 to 700 nm, with a maximum of over 70% at around 570 nm, DPP17 exhibited the best performance over the whole visible light region with a maximum of 86% also at 570 nm. DPP17 is the highest performing blue coloured dye, to the best of our knowledge, and the aesthetic advantages of a blue sensitizer are much more attractive with such strong performance. Notably, DPP17 achieved over 9% PCE on only ~3.2 μm thick transparent $TiO_2$ films, allowing for the development of blue, semi-transparent solar cells for building Integration Photovoltaic applications.

The invention claimed is:

1. A compound of formula (I)

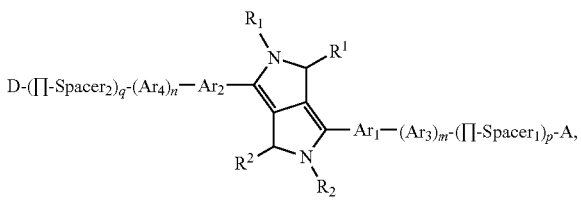

(I)

wherein:

m, n, p and q are independently selected from an integer from 0 to 3;

$R_1$ and $R_2$ are substituents of N atoms of the pyrrolopyrrole moiety and being independently selected from H, C1-C35 alkyl, C4-C35 aryl, C1-C35 arylalkyl, C4-C35 heteroaryl, wherein heteroatoms are selected from O, S or N;

$R^1$ and $R^2$ are substituents of the pyrrole rings and being independently selected from H, OH, S, =O (keto group), C1-C35 alkyl, C1-C35 thioalkyl, C1-C35 alkoxy, C4-C35 aryl, C1-C35 arylalkyl, C4-C35 heteroaryl, wherein heteroatoms are selected from O, S or N;

$Ar_1$ and $Ar_2$ are different from each other and $Ar_1$ and $Ar_2$ are aromatic aryl groups independently selected from a moiety according to any one of formula (1) to (18):

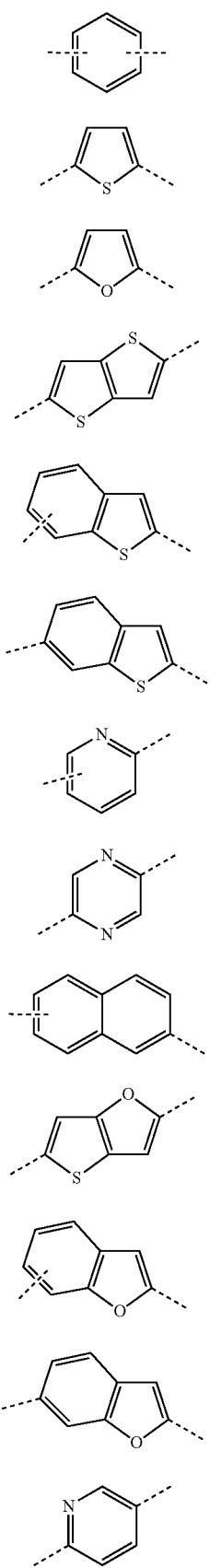
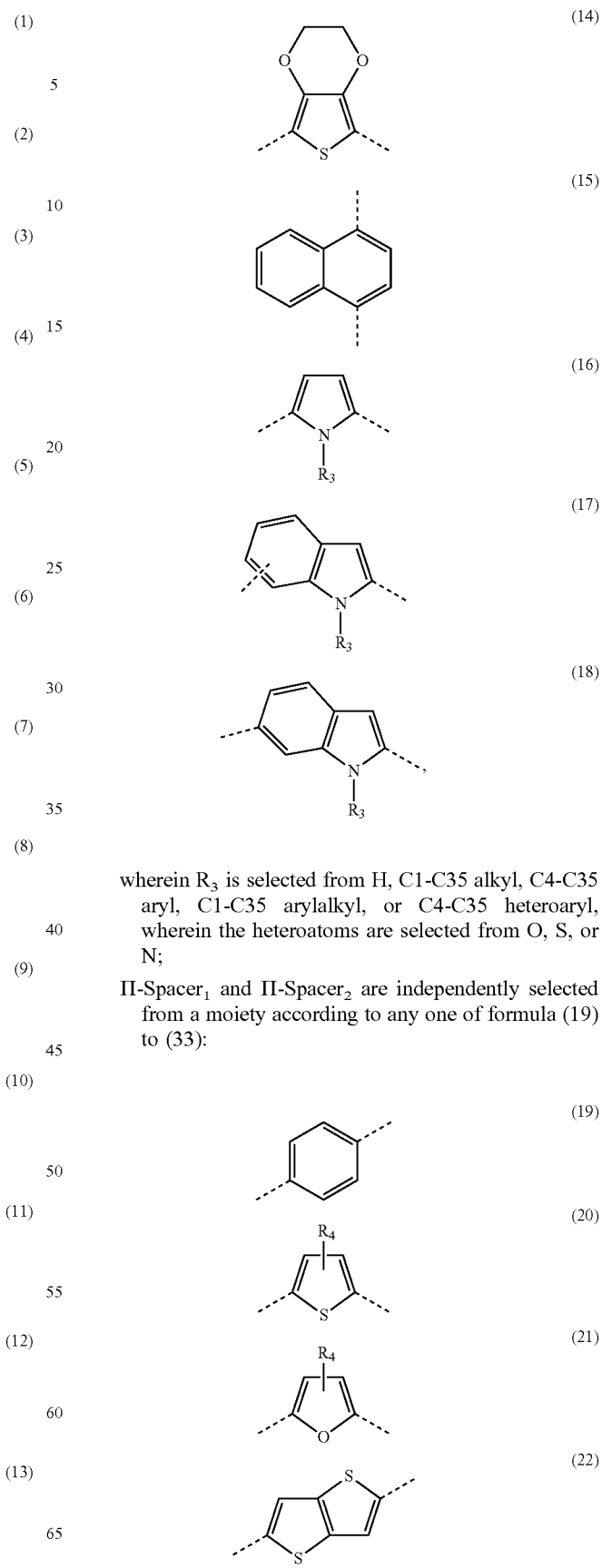
wherein $R_3$ is selected from H, C1-C35 alkyl, C4-C35 aryl, C1-C35 arylalkyl, or C4-C35 heteroaryl, wherein the heteroatoms are selected from O, S, or N;
Π-Spacer$_1$ and Π-Spacer$_2$ are independently selected from a moiety according to any one of formula (19) to (33):

-continued
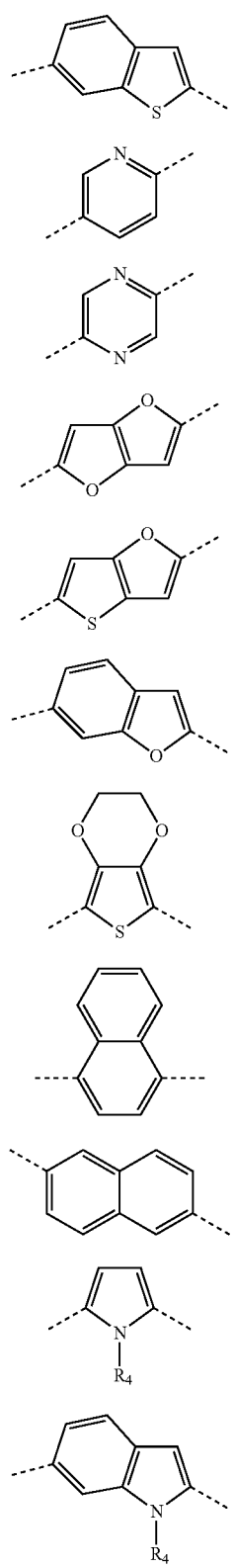
wherein R₄ is selected from H, C1-C35 alkyl, C1-C35 alkoxy, C1-C35 thioalkyl, C4-C35 aryl, C1-C35 arylalkyl or C4-C35 heteroaryl, wherein heteroatoms are selected from O, S, or N;
A is a substituent comprising an anchoring group "Anch" and an acceptor group and being selected from a moiety according to any one of formula (78) to (87):
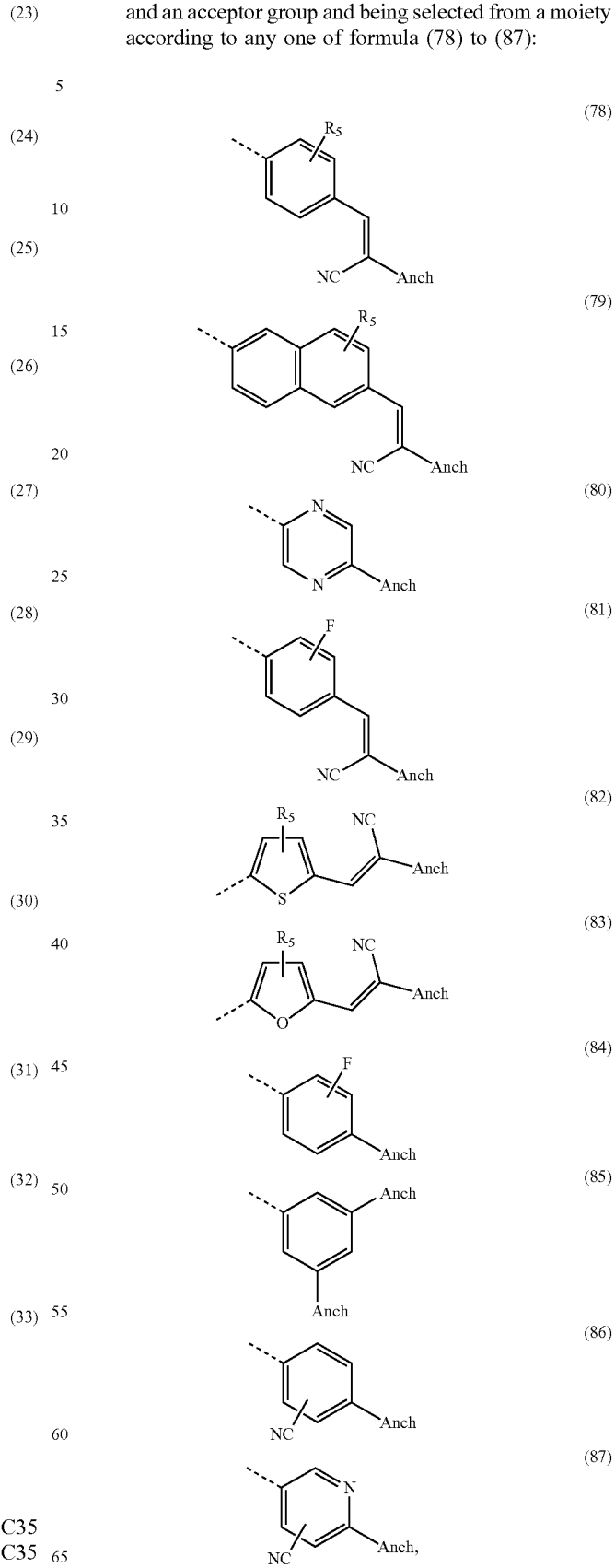

wherein $R_5$ is selected from H, C1-C35 alkyl, C1-C35 alkoxy, C1-C35 thioalkyl, C4-C35 aryl, C1-C35 arylalkyl or C4-C35 heteroaryl, wherein heteroatoms are selected from O, S, or N and Anch is an anchoring group independently selected from —COOH, $PO_3H_2$, —$PO_4H_2$, —$P(R_8)O_2H$, —$SO_3H_2$, —$SO_4H_2$, —CONHOH$^-$, 1,2-hydroxybenzene, 1-hydroxy-2-carboxybenzene, acetylacetonate, deprotonated forms of the aforementioned, organic and/or inorganic salts of said deprotonated forms, wherein $R_8$ is a hydrocarbon comprising from 1 to 50 carbons and 0-25 heteroatoms selected from O, N, or S, said hydrocarbon being covalently bound to the P atom of said phosphinic acid group by a carbon atom;

D is a donor group selected from a moiety according to any one of formula (44) to (55):

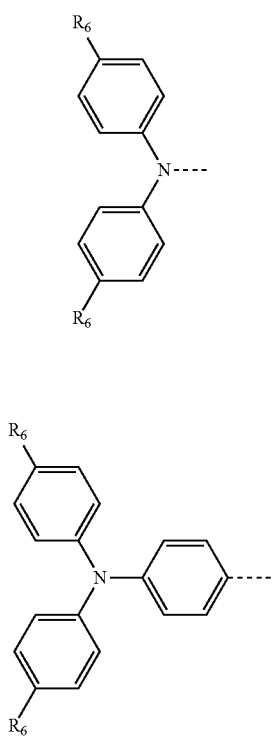

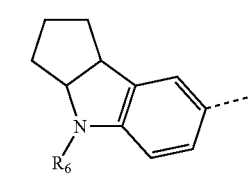

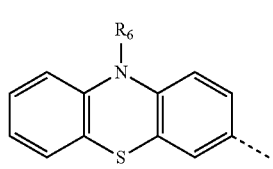

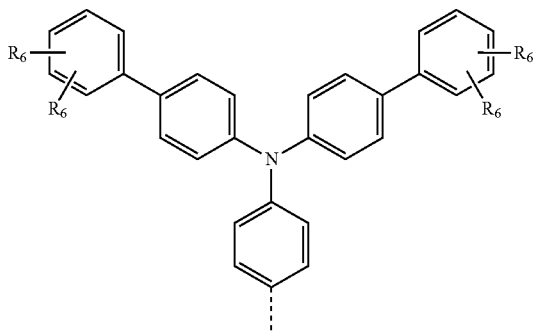

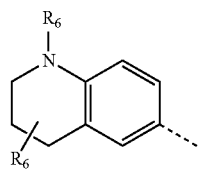

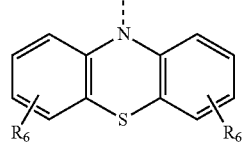

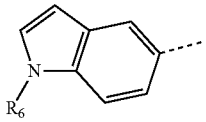

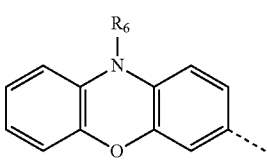

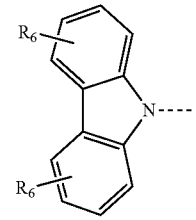

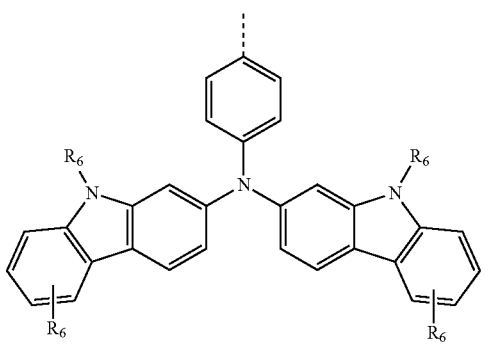

(55)

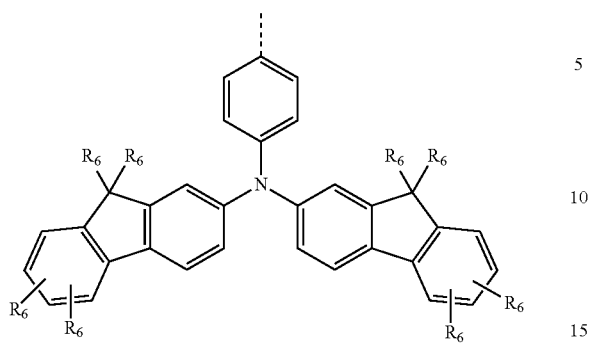

wherein R₆ is selected from H, C1-C35 alkyl, C1-C35 alkoxy, C1-C35 thioalkyl, C4-C35 aryl, C1-C60 arylalkyl or C4-C35 heteroaryl, wherein heteroatoms are selected from O, S, or N and wherein aryl is optionally substituted by C4-C35 arylalkyl or by C4-C35 arylalkoxy groups or by C4-C35 alkenylaryl or by C4-C35 alkenylarylalkoxy groups;

Ar₃ and Ar₄ are aromatic aryl groups independently selected from a moiety according to any one of formula (56) to (70):

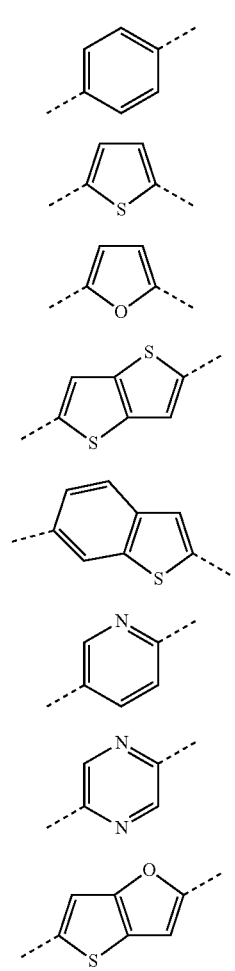

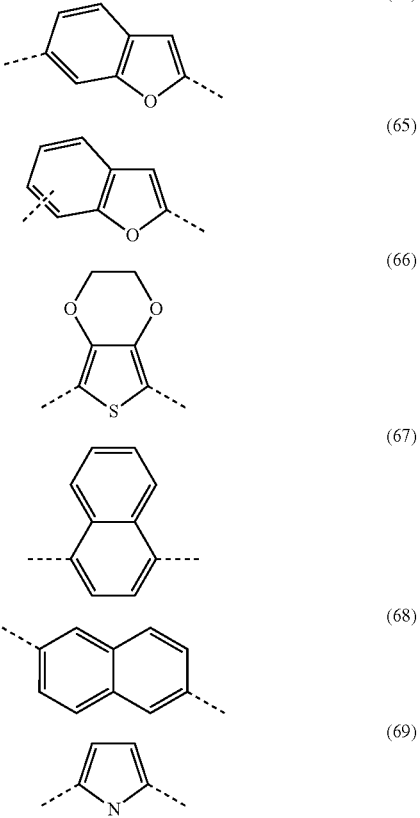

wherein R₇ is selected from H, C1-C35 alkyl, C4-C35 aryl, C1-C35 arylalkyl, or C4-C35 heteroaryl, wherein the heteroatoms are selected from O, S, or N;

and wherein said C1-C35 alkyl, C1-C35 alkoxy, C1-C35 thioalkyl, C4-C35 aryl, C1-C35 arylalkyl or C4-C35 heteroaryl may be further substituted or unsubstituted by a C1-C11 hydrocarbon comprising 0 to 15 heteroatoms selected from O, N, S or halogen.

2. The compound according to claim 1, wherein m and n are 0.

3. The compound according to claim 1, wherein p and q are 0 or 1.

4. The compound according to claim 1, wherein m and n are 0 and wherein p and q are 0 or 1.

5. The compound according to claim 1, wherein p is 0 and q is 1.

6. The compound according to claim 1, wherein m and n are 0; p is 0 and q is 1.

7. The compound according to claim 1, wherein p is 1 and q is 0.

8. The compound according to claim 1, wherein m and n are 0; p is 1 and q is 0.

9. The compound according to claim 1, wherein the alkyl chain of groups of C1-C35 alkyl and C1-C35 arylalkyl of R₁ and $R_2$ substituents of N atoms of the pyrrolopyrrole moiety are branched C1-C35 alkyl chain.

10. The compound according to claim 1, wherein A is selected from a moiety according to any one of formula (78), (80), (82), (83) or (84).

11. The compound according to claim 1, wherein D is selected from a moiety according to any one of formula (45), (46), (48) and (54).

12. The compound according to claim 1, wherein $R^1$ and $R^2$ being substituents of the pyrrole rings are selected from =O (keto group), S, C1-C35 alkoxy, or C1-C35 thioalkyl.

13. The compound according to claim 1, wherein $Ar_1$ and $Ar_2$ are independently selected from a moiety according to any one of formula (1), (2), (3), (7) and (13).

14. The compound according to claim 1, wherein $Ar_1$ is a moiety of formula (1), (7) or (13) and $Ar_2$ is a moiety of formula (2) or (3).

15. An electrochemical or optoelectronic device comprising a dye being a compound of formula (I) according to claim 1.

16. The device according to claim 15, wherein said device is selected from an electrochemical device, a photo-electrochemical device, an optoelectronic device, a light emitting device, an electrochromic or photo-electrochromic device, an electrochemical sensor, a biosensor, an electrochemical display and an electrochemical capacitor, or a dye sensitized solar cell.

17. The device according to claim 16 being a dye sensitized solar cell, wherein the dye is co-adsorbed with chenodeoxycholic acid.

* * * * *

UNITED STATES PATENT AND TRADEMARK OFFICE
CERTIFICATE OF CORRECTION

PATENT NO. : 9,697,956 B2
APPLICATION NO. : 14/425239
DATED : July 4, 2017
INVENTOR(S) : Thomas Wesley Holcombe et al.

Page 1 of 1

It is certified that error appears in the above-identified patent and that said Letters Patent is hereby corrected as shown below:

In the Specification

Column 1
- Line 60: "... donor-it-bridge-acceptor ..." to be replaced with "... donor-π-bridge-acceptor ..."

Column 16
- Line 29: "... An$_4$, ..." to be replace with "... Ar$_4$, ..."

Column 36
- Line 7: "... Gratzel, M.; ..." to be replaced with "... Grätzel, M.; ..."
- Line 7: "... Tones, T.; ..." to be replaced with "... Torres, T.; ..."
- Line 26: "... 1.5 G ..." to be replaced with "... 1.5G ..."
- Line 30: "... 1.5 G ..." to be replaced with "... 1.5G ..."

Column 41
- Line 11: "... and stiffing in ..." to be replaced with "... and stirring in ..."

Column 45
- 1st line after figures: "... Bis ..." to be replaced with "... bis ..."

Signed and Sealed this
Tenth Day of October, 2017

Joseph Matal
*Performing the Functions and Duties of the*
*Under Secretary of Commerce for Intellectual Property and*
*Director of the United States Patent and Trademark Office*